US008420884B2

(12) United States Patent  
Charest

(10) Patent No.: US 8,420,884 B2  
(45) Date of Patent: Apr. 16, 2013

(54) MODELS OF MALIGNANT BRAIN CANCER, AND THERAPEUTIC SIRNAS AGAINST ONCOGENIC SIGNALING PATHWAYS, AND METHODS AND KITS FOR USES THEREFOR

(75) Inventor: Alain Charest, Boston, MA (US)

(73) Assignee: Tufts Medical Center Inc., Boston, MA (US)

( * ) Notice: Subject to any disclaimer, the term of this patent is extended or adjusted under 35 U.S.C. 154(b) by 34 days.

(21) Appl. No.: 12/580,690

(22) Filed: Oct. 16, 2009

(65) Prior Publication Data

US 2010/0100974 A1 Apr. 22, 2010

Related U.S. Application Data

(60) Provisional application No. 61/196,422, filed on Oct. 16, 2008.

(51) Int. Cl.
   - *G01N 33/00* (2006.01)
   - *A01K 67/027* (2006.01)
   - *A01K 67/00* (2006.01)
   - *C12N 15/00* (2006.01)
   - *C12N 15/86* (2006.01)

(52) U.S. Cl.
   USPC ............... 800/3; 800/10; 800/18; 435/320.1; 435/456; 435/463

(58) Field of Classification Search ............... 800/3, 10, 800/18; 435/320.1, 456, 463
   See application file for complete search history.

(56) References Cited

U.S. PATENT DOCUMENTS

2008/0242742 A1* 10/2008 Depinho et al.

OTHER PUBLICATIONS

Mercier et al., 1997, "The modification of milk protein composition through transgenesis: progress and problems," In: Transgenic Animals: Generation and use, Ed. Houdebine LM, Harwood Academic Publishers, The Netherlands pp. 473-482.*
Goldman et al., 2004, Med Sci Monit, vol. 10, No. 11, RA274-285.*
Houdebine, L-M., 2002, Journal of Biotechnology, vol. 98, p. 145-160.*
Sigmund, C., Jun. 2000, Arterioscler. Thromb. Vasc. Biol., p. 1425-1429.*
Rescher et al., 2004, Journal of Cell Science, vol. 117, p. 2631-2639.*
Mogil et al., 1999, Pain, vol. 80, pp. 67-82.*
Schalkwyk et al., 2007, Genes, Brain and Behavior, vol. 6, p. 299-303.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002 Virology, vol. 304, p. 135-145.*
Chattopadhyay et al., 2004, Virus Research, vol. 99, p. 139-145.*
Fisher et al., 2001, Genes & Development, vol. 15, p. 3249-3262.*
Meuwissen et al., 2001, Oncogene, vol. 20, p. 6551-6558.*

Holland et al., 1998, Genes & Development, vol. 12, p. 3675-3685.*
Ballif et al. 2004 Mol Cell Prot 3: 1093-1101.
Bartel et al. 2004 Cell 116: 281-297.
Bartel et al. 2004 Nature 396-400.
Batzer et al. 1994 Mol Cell Biol 14: 5192-5201.
Beard et al. 2006 Genesis 44: 23-28.
Beausoleil et al. 2004 Pro Natl Acad Sci 101: 12130-12135.
Biscardi et al. 1999 J Biol Chem 274: 8335-8343.
Bollerot et al. 2006 Develop Dynam 235: 105-114.
Cantin et al. 2006 J Proteome Res 5: 127-134.
Cantley et al. 2002 Science 296: 1655-1657.
Carpenter et al. 1993 J Biol Chem 268: 9478-9483.
Chakravarti et al. 2007 Cum Oncol Rep 9: 71-79.
Chakravarti et al. 2005 Int J Radiat Oncol 62: 318-327.
Chang et al. 2005 Investig New Drugs 23: 357-361.
Charest et al. 2006 Cancer Res 66: 7473-7481.
Chattopadhyay et al. 1999 J Biol Chem 274: 26091-26097.
Chien et al. 2005 Gene Ther 12: 321-328.
Choi et al. 2007 Advan Enzyme Regul 47: 104-116.
Chumbalkar et al. 2005 Proteomics 5: 1167-1177.
Collins et al. 2005 J Biol Chem 280: 5972-5982.
Contag et al. 2002 Annu Rev Biomed Eng 4: 235-260.
Dasgupta et al. 2005 Cancer Res 65: 2755-2760.
De Jonge et al. 2006 Gene Ther 13: 400-411.
De Sepulveda et al. 1999 Embo J 18: 904-915.
Demuth et al. 2004 J Neuro-Oncol 70: 217-228.
Duxbury et al. 2004 Ann Surg 240: 667-676.
Engelman et al. 2007 Science 316: 1039-1043.
Fabbri et al. 2007 Expert Opin Biol Ther 7: 1009-1019.
Faivre et al. 2006 Nature 5: 671-688.
Fantl et al. 1992 Cell 69: 413-423.
Franceschi et al. 2007 Br J Cancer 96: 1047-1051.
Franke et al. 2003 Oncogene 22: 8983-8998.
Frias et al. 2006 Cuff Biol 16: 1865-1870.
Fujii et al. 2006 Int J Oncol 29: 541-548.
Galanis et al. 2005 J Clin Oncol 23: 5294-5304.
Gilbert et al. 2007 Curr Oncol Reports 9: 49-54.
Gilmore et al. 2006 Curr Drug Deliv 3: 147-155.
Guissouma et al. 2006 Neurosci Lett 406: 240-243.
Goplen et al. 2006 Cancer Res 66: 9895-9902.
Groszer et al. 2006 Science 294: 2186-2189.
Gruhler et al. 2005 Mol Cell Proteomics 4: 310-327.
Grzelinski et al. 2006 Hum Gene Ther 17: 751-766.
Guan et al 2008 Adv Biochem Engin/Biotechnol 110: 1-24.

(Continued)

*Primary Examiner* — Shin-Lin Chen
(74) *Attorney, Agent, or Firm* — Lawson & Weitzen, LLP; Sonia K. Guterman; Sanjeev K. Mahanta

(57) ABSTRACT

Methods for screening compounds to treat an oncological disorder regulated through a tumor-inducing pathway are provided. The compounds are administered to non-human animal subjects having a disease model, so that the subjects display pathology symptoms that correspond to the oncological disorder in humans. The subjects carry a regulatable transgene expression, of which is associated with tumor formation, and further carry regulatable genes for suppression of tumor formation. The disease-pathology symptoms are induced using a site-specific recombination system to induce expression of the transgene associated with tumor formation and negatively regulate or eliminate the genes for suppression of the tumor formation. The methods further involve analyzing tumor formation in subjects administered the compound and comparing appearance and amount of tumors in the subjects administered the compound with control subjects not administered the compound. Also included are a vector for engineering a disease model and a kit for its use.

14 Claims, 27 Drawing Sheets

OTHER PUBLICATIONS

Guertin et al. 2007 Cancer Cell 9-22.
Halder et al. 2006 Clin Cancer Res 12: 4916-4924.
Hall et al. 2006 Neurosurg Focus 20: E23 (1-6).
Hallberg et al. 1994 J Biol Chem 269: 3913-3916.
Harmer et al. 1999 J Biol Chem 274: 12183-12191.
Hay et al. 2004 Gene Develop 18: 1926-1945.
Heimberger et al. 2005 Clin Cancer Res 11: 1462-1466.
Hennet et al. 1995 Proc Natl Acad Sci 92: 12070-12074.
Hobbs et al. 2003 J Magnet Resonan Imag 18: 530-536.
Holland et al. 1998 Genes Develop 12: 3644-3649.
Howard et al. 2006 Mol Ther 14: 476-484.
Huang et al. 2007 Cell Cycle 6: 2750-2754.
Huang et al. 2007 Pro Natl Acad Sci 104: 12867-12872.
Iwadate et al. 2004 Cancer Res 64: 2496-2501.
Iwadate et al. 2005 Int J Oncol 26: 993-998.
Jackson et al. 2001 Genes Develop 15: 3243-3248.
Kang et al. 2008 J Nucl Med 49: 164S-179S.
Kashishian et al. 1992 Embo J 11: 1373-1382.
Kassner et al. 2008 Combinator Chem High Through Screen 11: 175-184.
Kato et al. 2007 Cancer Res 67: 8544-8553.
Kazlauskas et al. 1992 Mol Cell Biol 12: 2534-2544.
Kuan et al. 2001 Endocr Rel Cancer 8: 83-96.
Kuhn et al. 2007 High Energ Phys 178: 149-176.
Kumar et al. 2007 Nature 448: 39-45.
Kumar et al. 2007 PLoS Computat Biol 3: e4 (1-14).
Lassman et al. 2005 Cancer Ther 11: 7841-7850.
Lassman et al. 2006 N Engl J Med 354: 525.
Leng et al. 2005 Cancer Gene Ther 12: 682-690.
Lesche et al. 2002 Genesis 32: 148-149.
Liaw et al. 1998 Am J Physiol Lung Cell Mol Physiol 274: L665-L672.
Lowenstein et al. 1992 Cell 70: 431-442.
Luhn et al. 2007 Proteins 67: 479-489.
Lyons et al. 2003 Cancer Res 63: 7042-4046.
Mathupala et al. 2007 DNA Cell Biol 26: 301-310.
Mavrakis et al. 2008 Gene Develop 22: 2178-2188.
McClellan et al. 1999 Exper Cell Res 246: 471-479.
McLendon et al. 2008 Nature 455: 1061-1068.
McManus et al. 2002 RNA 8: 842-850.
Miyazaki et al. 1989 Gene 79: 269-277.
Moser et al. 2006 J Proteome Res 5: 98-104.
Neshat et al. 2001 Pro Natl Acad Sci 98: 10314-10319.
Newton et al. 2004 Expert Rev Anticancer Ther 4: 105-128.
Nicholson et al. 2002 Cellul Signal 14: 381-395.
Nogawa et al. 2005 J Clin Investig 115: 978-985.
Novina et al. 2004 Nature 430: 161-164.
Ocker et al. 2005 Gut 54: 1298-1308.
Odreman et al. 2005 J Proteome Res 4: 698-708.
Ohtani et al. 2004 J Med Invest 51: 146-153.
Omuro et al. 2007 Mol Cancer Ther 6: 1909-1919.
Paddison et al. 2008 Curr Topic Microbiol Immunol 320: 1-13.
Pal et al. 2005 Int J Oncol 26: 1087-1091.
Parsons et al. 2008 Science 321: 1807-1812.
Pawson et al. 2007 Curr Opin Cell Biol 19: 112-116.
Pedersen et al. 2001 Ann Oncol 12: 745-760.
Pille et al. 2006 Hum Cell Ther 17: 1019-1026.
Podsypanina et al. 2001 Proc Natl Acad Sci 98: 10320-10325.
Quan et al. 2005 Int J Radiat Biol Phys 63: 695-703.
Raghavan et al. 2006 Neurosurg Focus 20: E12 (1-13).
Ram et al. 1996 Cell Growth Differentat 7: 551-561.
Ramnarain et al. 2006 Cancer Res 66: 867-874.
Rao et al. 2005 Neoplasia 7: 921-929.
Reardon et al. 2006 Clin Cancer Res 12: 860-868.
Rikova et at 2007 Cell 131: 1190-1203.
Rousseaux et al. 2008 Reproduct BioMed 16: 492-503.
Safran et al. 2003 Mol Imag 297-302.
Saito et al. 2001 J Mol Cell Cardiol 33: 3-7.
Saito et al. 2001 Mol Cell Biol 21: 6387-6394.
Sakaguchi et al. 1998 Mol Endocrinol 12: 536-543.
Sampson et al. 2006 Neurosurg Focus 20: E14 (1-4).
Santel et al. 2006 Gene Ther 13: 1222-1234.
Santel et al. 2006 Gene Ther 13: 1360-1370.
Sarkaria et al. 2006 Clin Cancer Res 12: 2264-2271.
Sarkaria et al. 2007 Mol Cancer Ther 6: 1167-1174.
Schlaepfer et al. 1999 Progress Biophys Mol Biol 71: 435-478.
Schwartz et al. 2005 Cancer Res 65: 7674-7681.
Sebastian et al. 2006 Biochim Biophys Acta 1766: 120-139.
Serrano et al. 1996 Cell 85: 27-37.
Sharpless et al. 2004 Experiment Gerontol 39: 1751-1759.
Sharpless et al. 2004 J Clin Investig 113: 160-168.
Sharpless et al. 2005 Nature 436: 636-637.
Shin et al. 2006 Proc Natl Acad Sci 103: 13759-13764.
Song et al. 2005 Nat Biotechnol 23: 709-717.
Stommel et al. 2007 Science 318: 287-290.
Stupp et al. 2005 N Engl J Med 352: 987-996.
Sun et al. 2006 Biotechniques 41: 59-63.
Svensson et al. 2008 Mol Ther 16: 1995-2001.
Takei et al. 2004 Cancer Res 64: 3365-3370.
Tice et al. 1999 Proc Natl Acad Sci 96: 1415-1420.
Trinidad et al. 2006 Mol Cell Proteomics 5: 914-622.
Tyner et al. 2008 Blood 111: 2238-2245.
Urban-Klein et al. 2005 Gene Therapy 12: 461-466.
Ushio et al. 2003 Frontiers Biosci 8: e281-e288.
Vandergrift et al. 2006 Neurosurg Focus 20: E13 (1-8).
Voelzke et al. 2008 Curr Treat Opt Oncol 9: 23-31.
Weinstein et al. 2008 Cancer Res 68: 3077-3080.
White et al. 2008 Curr Opin Biotechnol 19: 404-409.
Wolters et al. 2008 Cell Death Differentat 15: 809-819.
Woolfenden et al. 2009 Genesis 47: 659-666.
Xiao et al. 2005 Cancer Res 65: 5172-5180.
Xu et al. 2007 Chin Med J 120: 996-999.
Yano et al. 2004 Clin Cancer Res 10: 7721-7726.
Zhou et al. 2006 Neuroscience 401: 59-64.
Zhu et al. 2009 Proc Natl Acad Sci 106: 2712-2716.
Zimmermann et al. 2006 Nature 441: 111-114.

* cited by examiner

3374 /STAT3 AS0 /4 mg/ml 0.5ul/hr /TUMOR BEARING MOUSE /7

MODELS OF MALIGNANT BRAIN CANCER, AND THERAPEUTIC SIRNAS AGAINST ONCOGENIC SIGNALING PATHWAYS, AND METHODS AND KITS FOR USES THEREFOR

RELATED APPLICATION

This application claims the benefit of U.S. provisional application 61/196,422 filed Oct. 16, 2008 in the U.S. Patent and Trademark Office, which is hereby incorporated herein by reference in its entirety.

GOVERNMENT SUPPORT

This work was supported in part by a grant from the National institutes of Health (U54 CA119349). The government has certain rights in the invention.

TECHNICAL FIELD

The invention relates to an animal model of malignant brain cancer and methods for screening to obtain therapeutic agents, and methods of treating subjects having malignant brain cancer.

BACKGROUND

Glioblastoma multiforme (GBM) is the most common and lethal primary malignant cancer of the central nervous system found in adults with an incidence of about 2-3 per 100,0000, and claim the lives of over 80% of patients within a year of diagnosis. Despite multimodal therapies, the median survival of GBM patients is about 1 year. The deadly nature of GBM resides in its explosive growth characteristic, extreme invasive behavior and intrinsic resistance to current therapies. Surgical resection and radiotherapy have been the mainstay of treatment until recently, as superiority of chemotherapy has unequivocally been shown in a randomized trial (Stupp, R. et al. 2005 N Engl J Med 352:987-996). Despite efforts to develop novel treatments, little improvement in overall survival or progression-free survival has been achieved in the past five decades, reflecting an unmet need in the treatment of this cancer (Kleihues, P. et al. 2000 IARC Press, Lyon, France).

SUMMARY OF THE EMBODIMENTS

An embodiment of the invention provided herein is a method for screening at least one compound to determine ability of the compound to treat an oncological disorder regulated through a tumor-inducing pathway, the method including:

administering the compound to non-human animal subjects having a disease model, such that the subjects display pathology symptoms that correspond to the oncological disorder in a human, and such that the subjects further carry a regulatable transgene such that expression of the transgene is associated with tumor formation, and further carry regulatable genes for suppression of tumor formation, such that the disease pathology symptoms are induced using a site-specific recombination system to induce expression of the transgene associated with tumor formation and negatively regulate or eliminate the genes for suppression of tumor formation;

analyzing tumors appearing in subjects administered the compound; and comparing appearance and amount of tumors in the subjects administered the compound and in the control subjects not administered the compound, such that a decrease in tumors in subjects administered the compound compared to control subjects is an indication that the compound treats the oncological disorder.

In a related embodiment, the method includes as the transgene of the tumor-inducing pathway, an EGF receptor (EGFR). For example, the transgene associated with tumor formation encodes an EGFR mutation vIII ($EGFR^{vIII}$).

An alternative embodiment includes a plurality of transgenes associated with tumor formation, such as transgenes encode each of $EGFR^{vIII}$ and wild type EGFR ($EGFR^{WT}$).

An embodiment of the method further includes, as the regulatable genes for suppression of tumor formation, those encoding INK4a-ARF and PTEN mutations.

In a related embodiment, the site-specific recombination system is selected from at least one of the group of: cre-lox, r-rs, gin-gix and flp-frt. For example, the site-specific recombination system is cre-lox In general, the oncological disorder is selected from at least one of the group: glioblastoma multiforme (GBM), renal cell carcinoma, pancreatic cancer, colorectal cancer, lung cancer, prostate cancer and breast cancer.

Accordingly, in an embodiment of the method, the tumor formation transgene encodes $EGFR^{vIII}$ under control of a cytomegalovirus (CMV) promoter immediate early enhancer and a chicken β-actin promoter sequence (pCAGGS), such that the promoter is conditionally repressed by the presence of a foxed stop cassette, the $EGFR^{vIII}$ encoding region is flanked at 3' and 5' ends by collagen1α1 genomic sequences, and the $EGFR^{vIII}$ transgene is expressed in cells contacted with Cre recombinase.

The method in one embodiment involves performing stereotactic intracranial injections of adenovirus transducing Cre recombinase (Ad-CMVCre) such that cre-lox function over-produces $EGFR^{vIII}$ and down regulates INK4a-ARF and PTEN.

In a related embodiment, comparing appearance and amount of tumors in subjects includes bioimaging and analyzing tumor growth non-invasively. For example, non-invasive bioimaging includes observing amount of a bioluminescent marker under control of a strong ubiquitous promoter, such that the promoter is conditionally repressed by presence of the foxed stop cassette, and the marker is expressed in cells contacted with Cre recombinase such that cells produce tumors and express the marker. In a related embodiment, comparing appearance and amount of tumors is performed in living animals without sacrificing the animals.

In various embodiments, comparing amount of tumors further includes observing at least one of: extent of cellularity; presence of pleomorphic nuclei; presence of a fibrillary background; robust membrane expression; presence of astrocytic markers GFAP and/or S100 β; extent of proliferating cells by presence of mitoses; extent of areas of necrosis; presence of perineuronal satellitosis; and presence of tumor cells that have migrated distal to the main tumor mass.

In general, the animal is a rodent, and the method is not limited to any particular animal group, and other animals such as rabbits, dogs, sheep, horses, or primates may be used. For convenience and practicability, the animal is a rodent selected from the group of: mouse, rat, hamster, and guinea pig.

Also provided herein is a transgenic animal made according to any of the above methods, as is a cell from the transgenic animal, including a primary cell culture and an established cell culture In one embodiment, the method further includes, after comparing, analyzing an amount of mTORC protein in tumors in animals administered the compound and in controls not administered the compound, such that analyzing includes determining at least one of; expression of mTORC per total protein; activation of mTORC activity; extent and pattern of mTORC phosphorylation; and relative usage of mTORC1 and mTORC2.

Also provided herein is a method of reducing expression of EGFR$^{vIII}$, the method including administering a vector carrying an shRNA targeting EGFR$^{vIII}$ mRNA. For example, the vector is a pSLIK lentiviral backbone. In general, obtaining the shRNA targeting EGFR$^{vIII}$ mRNA includes analyzing cDNA sequences of the EGFR$^{vIII}$ mRNA with pSICOLIGO-MAKER software to determine best scoring 21 nucleotide sequences that mediate RNA interference.

Also provided herein is a vector for engineering a glioblastoma multiforme (GBM) animal model, such that the vector includes a transgene encoding an epidermal growth factor receptor variant vlll (EGFRvIII), the transgene being operatively linked to a strong ubiquitous promoter composed of the cytomegalovirus (CMV) promoter immediate early enhancer and chicken β-actin promoter sequences (pCAGGS) flanked at 3' and 5' ends with collagen1α1 genomic sequences, and the promoter is conditionally repressed by the presence of a foxed stop cassette.

Also provided herein is a kit for engineering an animal model for glioblastoma multiforme (GBM), the kit including a vector according to the above, and a container and instructions for use.

Another embodiment of the invention provided herein is a method for screening at least one compound to determine ability of the compound to treat an oncological disorder regulated through a tumor-inducing pathway, the method including:

administering the compound to a non-human animal subjects having a disease model, in which the subjects display pathology symptoms that correspond to the oncological disorder in a human, the subjects further carry a regulatable wild type transgene of human origin expression which is associated with tumor formation, and regulatable genes for suppression of tumor formation, and the disease pathology symptoms are induced using a site-specific recombination to induce expression of the transgene associated with tumor formation and negatively regulate or eliminate the genes for suppression of tumor formation;

analyzing tumors appearing in subjects administered the compound; and comparing appearance and amount of tumors in the subjects administered the compound with that in control subjects not administered the compound, such that a decrease in tumors in subjects administered the compound compared to control subjects is an indication that the compound treats the oncological disorder.

A related embodiment of the method includes a plurality of the transgenes of the tumor-inducing pathway associated with tumor formation, such as transgenes encoding a wild type EGFR receptor (EGFR$^{WT}$) and an additional transgene. For example, the additional transgene encodes a TFGα.

In a related method the genes for suppression of tumor formation encode INK4a-ARF and PTEN mutations. Further, the site-specific recombination system is selected from at least one of the group of: cre-lox, r-rs, gin-gix and flp-frt. The oncological disorder is selected from at least one of the group: glioblastoma multiforme (GBM), renal cell carcinoma, pancreatic cancer, colorectal cancer, lung cancer, prostate cancer and breast cancer.

A related embodiment of the method further includes regulating the tumor formation transgene with a cytomegalovirus (CMV) promoter immediate early enhancer and a chicken β-actin promoter sequence (pCAGGS), wherein the promoter is conditionally repressed by the presence of a foxed stop cassette, and wherein the transgene is flanked at 3' and 5' ends by collagen1α1 genomic sequences wherein the transgene is expressed in cells contacted with Cre recombinase. For example the site specific recombination system is cre-lox.

A related embodiment of the method further includes performing stereotactic intracranial injection of adenovirus transducing Cre recombinase (Ad-CMVCre), such that cre-lox function overproduces EGFR$^{WT}$ and down regulates PTEN.

In general comparing appearance and amount of tumors in subjects further comprises bioimaging to monitor tumor growth non-invasively. Non-invasive bioimaging includes observing an amount of expression of a bioluminescent marker under control of a strong ubiquitous promoter, wherein the promoter is conditionally repressed by presence of a floxed stop cassette, such that the marker is expressed in cells contacted with Cre recombinase, such that the cells produce tumors and express the marker. Thus, comparing appearance and amount of tumors is performed in living animals without sacrificing the animals.

The methods herein can further include, for comparing amount of tumors, observing at least one of: extent of cellularity; presence of pleomorphic nuclei; presence of a fibrillary background; extent of membrane expression; presence of astrocytic markers GFAP and/or S100 β; extent of proliferating cells by presence of mitoses; extent of areas of necrosis; presence of perineuronal satellitosis; and presence of tumor cells migrated distal to main tumor mass.

In general, the animal is a rodent selected from the group of: mouse, rat, hamster and guinea pig. A related embodiment provided herein is a transgenic animal according to the methods herein, and a cell from a transgenic animal.

The method can further involve, after comparing, analyzing an amount of mTORC protein in tumors in subjects administered the compound and in the control subjects not administered the compound, such that analyzing involves determining at least one of: expression of mTORC per total protein; activation of mTORC activity; extent and pattern of mTORC phosphorylation; and relative usage of mTORC1 and mTORC2.

Also provided is a vector for engineering a glioblastoma multiforme (GBM) animal model system comprising a transgene encoding a wild type epidermal growth factor receptor (EGFR$^{wt}$) such that the EGFR$^{WT}$ is operatively linked to a cytomegalovirus (CMV) promoter immediate early enhancer and a chicken β-actin promoter sequence (pCAGGS), such that the promoter is conditionally repressed by the presence of a foxed stop cassette, and the EGFR is flanked at 3' and 5' ends by collagen1α1 genomic sequences. Also provided is a kit including this vector, container and instructions for use.

Also provided herein is a method for treating a subject for glioblastoma multiforme (GBM), the method including administering to the subject a composition for modulating expression or activity of a variant form of epidermal growth factor receptor (EGFR). In an embodiment of the method, modulating is down regulating, and the method further includes observing a change in a phosphorylation pattern of at least one member of a proto-oncogene pathway. For example, the pathway includes at least one protein from the group of Ras, phospholipase C-γ (PLC γ), MAPK, INK, PDK1, AKT, PTEN, MDM2, p21/p27, Bad, ASK-1, FKHR, IkB, caspase-9, SGK3, FoxO, TSC2, mTOR and the like for example as shown in Tables 1 and 2. In general without being limited by any specific mechanism of action, the EGFR variant is EGFRvlll, and it is anticipated that other equivalent variants of EGFR will be observed that similarly are mutated and are associated with GBM, and these variants too are within the scope of the invention.

Examples of the composition include an shRNA or an siRNA that has a nucleotide sequence of the EGFR variant. For example, the shRNA is expressed from a viral vector, such as a pSLIK lentivirus, and shRNA that is inducible by a tetracycline, for example, doxycline.

Yet another embodiment of the invention provided herein is a method of formulating a medicament for treatment of glioblastoma multiforme (GBM), the method including preparing a composition with an shRNA or an siRNA having a nucleotide sequence of an epidermal growth factor receptor (EGFR) variant. In an embodiment of the method the composition further includes an additional drug, for example, the drug is an agent selected from the group of: a cancer chemotherapeutic, a cytokine, an antibiotic, an antifungal and an analgesic. In additional embodiments, the method includes formulating the shRNA or an siRNA in a unit dose. In additional embodiments, the method includes formulating the composition with a pharmaceutically acceptable buffer.

Also provided herein is a composition for treatment of glioblastoma multiforme (GBM), including an shRNA or an siRNA with a nucleotide sequence of an EGFR variant.

BRIEF DESCRIPTION OF DRAWINGS

FIG. 1 panel A shows RTK/RAS/PI3K pathways.

FIG. 1 panel B shows p53 pathways.

FIG. 1 panel C shows RB cell cycle pathways.

FIG. 2 panel A is a drawing of a schematic representation of the Col1α1 locus Flp-in system in C2 ES cells. A promoter and ATG-less hygromycin resistance cassette were inserted in the 3' region of the collagen 1α1 gene. Transient transfection of a targeting plasmid with a Flpe recombinase plasmid in C2 ES cells resulted in restoration of a functional hygromycin resistance cassette and the introduction of a CAGGS-loxS-TOPlox-EGFR segment. Exons are shown as light gray boxes and 3' UTR as a open box. P, PstI; S, SpeI; X, XhoI. The figure is not drawn to scale.

FIG. 2 panel B is a photograph of a Southern blot analysis of hygromycin-resistant flp-in clones for EGFR wild type and EGFR$^{vIII}$ alleles using a 3' internal probe (indicated).

FIG. 3 panel A is a drawing showing a schematic representation of activation of conditional EGFR transgenes. A strong ubiquitous promoter (CAGGS) was positioned upstream of a transcriptional stop cassette (STOP) which is flanked by two loxP sites (dark gray triangles), followed by either wild type (WT) or mutated (vIII) human EGFR cDNAs and a polyA signal sequence (rectangle). The expression of EGFR was conditional to removal of the stop cassette, which is mediated by presence of an adenovirus expressing Cre recombinase.

FIG. 3 panel B is a Kaplan-Meier graph showing survival analysis of Ad-Cre-injected conditional EGFR cohorts of mice with the indicated genotypes. EGFR$^{WT/WT}$ (n=6; -x-), EGFR$^{vIII/vIII}$ (n=5; solid circles). The EGFR$^{WT/WT}$ (n=33; solid diamonds), EGFR$^{vIII/vIII}$ (n=4; triangles), and EGFR$^{WT/vIII}$ (n=8; squares), each in an InkΔ2/3$^{-/-}$ and PTEN$^{-/-}$ background. The data show survival of controls EGFR$^{WT/WT}$ and death of animals carrying vIII during the two week trial course.

FIG. 4 panel A shows tumors set on a fibrillary background contained pleimorphic nuclei (white arrow) and mitoses (black arrow).

FIG. 4 panel B shows tumors demonstrating marked pseudo pallisading necrosis.

FIG. 4 panel C shows tumor cells that had a tendency to accumulate around neurons, a common feature known as perineuronal satellitosis, and the highly infiltrative nature of EGFR tumor cells.

FIG. 4 panel D shows tumor cells (black arrow heads) that had infiltrated white matter tracts such as the corpus callosum (CC) and the perivascular space (white arrow head).

FIG. 4 panel E shows tumor cells that had migrated within the subarachnoid space.

FIG. 4 panel F shows IHC stain for human EGFR demonstrating that tumor cells had infiltrated normal brain. Scale bars 15 μM (A), 30 μM (C, E, F), 62.5 μM (B, D).

FIG. 6 panel A is set of longitudinal serial MR images showing mice of the indicated genotypes on an InkΔ2/3$^{-/-}$; PTEN$^{-/-}$ background imaged by MRI over a period of time. Gad-enhanced T1 weighted images of EGFR$^{WT/WT}$ were taken at time points i=37, ii=120 and iii=145 days post Ad-Cre injection. Images of EGFR$^{WT/vIII}$ were taken at time points i=37, ii=44 and iii=48 days post Ad-Cre injection. Images of EGFR$^{vIII/+}$ were taken at time points i=43, ii=50 and iii=53 days post Ad-Cre injection.

FIG. 6 panel B is a line graph showing quantitative measurement of tumor volumes from MRI imaging as a function of time. For each mouse, tumor area from serial 1 mm sections were multiplied by the slice thickness and then added to obtain a final volume.

FIG. 6 panel C is a set of photomicrographs of H&E-stained coronal sections of tumors shown in panel A from each of: EGFR$^{WT/vIII}$; InkΔ2/3$^{-/-}$; PTEN$^{-/-}$, and, EGFR$^{vIII/+}$; InkΔ2/3$^{-/-}$; PTEN$^{-/-}$.

FIG. 7 panel A is a photograph of Western blot analysis of representative ex vivo GBM tumor cells from the animal model herein expressing each of EGFR$^{WT}$, EGFR$^{WT/vIII}$ receptors EGFR$^{vIII}$ receptors each in an InkΔ2/3$^{-/-}$;PTEN$^{-/-}$ background. Cells were serum starved for 24 hours and stimulated with 50 ng/mL EGF for 5 min. Immunoblots of the indicated total cell lysates were probed with phosphotyrosine residue-specific anti EGFR antibodies.

FIG. 7 panel B is a drawing showing a achematic representation of the 12 known pTyr residues located in EGFR (grey circles) and their interacting signaling counterparts. Phosphorylated sites inn EGFR$^{WT}$ and EGFR$^{vIII}$ in GBM tumor cells are marked with arrows. Note that while the amino acid sequences surrounding the pTyr sites are the same, the numbering in EGFR$^{vIII}$ is different than in EGFR$^{WT}$ due to deletion of amino acid residues 6-273.

FIG. 13 panel A shows low resolution CGH data for all 19 chromosomes for each of EGFR$^{WT}$, EGFR$^{WT/vIII}$ and EGFR$^{vIII}$ tumor cells. Two arrows on the left side of the panel for EGFR$^{WT/WT}$ and an arrow for EGFR$^{WT/vIII}$ indicate examples of observed amplicons and two arrows on the right side of a panel indicate examples of observed focal deletions.

FIG. 13 panel B shows boxes with data for higher resolution of focal amplification on chromosomes 1 and 5 with genes indicated.

FIG. 13 panel C shows amounts of FAKTS/URLC9 gene overexpression in human GBM samples compared to normal brain tissue (Oncomine, Rhodes, D. R. et al. 2004 Neoplasia 6:1-6).

FIG. 14 panel A is a thematic representation of the pSLIK lentiviral backbone.

FIG. 14 panel B is a photograph and bar graph showing expression of a shRNA specific for EGFR$^{vIII}$, the expression observed following intracranial injection into nude mice and tumor development monitored by bioluminescence imaging (BLI) and quantitated. EGFR GBM cells were infected with a firefly luciferase lentivirus and a pSLIK virus expressing a shRNA against EGFRvIII by intracranial injection in nude mice and tumor development was monitored by BLI and was quantitated. Shown are BLI values observed each of 71 and 81 days post implantation. At 71 days, mice each of 1 and 3 were fed doxycycline (dox) in their drinking water. Tumor growth was arrested in dox-treated tumors but not in control mice (graph).

FIG. 14 panel C is photograph of a Western blot showing a comparison of doxycycline induced knowckdown of EGFR$^{vIII}$ proteins observed in each of parental cells (pre-implantation) and in cells mouse tumor (post implantation).

FIG. 14 panel D is a photograph showing EGFR immunofluorescence of tumors from mice treated with doxycycline (+dox) and control animals (−dox).

FIG. 15 panel A shows a mini gene having a strong ubiquitous promoter (CAGGS), activity of which is attenuated by the presence of a transcriptional and translational stop cassette flanked by two loxP sites positioned next to the human EGFR cDNA. This mini gene was inserted in the 3'UTR of the collagen 1α1 gene by homologous recombination in embryonic stem cells. Upon delivery of Cre recombinase, the stop cassette was excised, juxtaposing the CAGGS promoter to the EGFR cDNA, allowing for expression of the EGF receptor. A virus (lentivirus) capable of expressing tandemly Cre recombinase and the EGFR ligand TGFα was used in this system since expression of the EGFR$^{WT}$ alone was insufficient to trigger tumor formation.

FIG. 15 panel B shows an intracranial injection of the lentivirus in EGFR;InkΔ2/3$^{-/-}$; PTEN$^{2lox}$ mice.

FIG. 15 panel C shows the EGF receptor protein at the plasma membrane bound to TGFα ligand and activation through the receptor autophosphorylation tyrosine residues (indicated by arrows) and signaling pathways resulting from phosphorylated tyrosine residues.

FIG. 16 panel A is a schematic representation of the lentivirus genome and production of viruses. The elongation factor 1 alpha (EF1α) promoter drives transcription of a bicistronic mini gene carrying each of: human TGFα cDNA, an internal ribosomal entry site sequence and the iCre cDNA. Viruses were produced using standard procedures.

FIG. 16 panel B is photomicrograph showing pTYF-TGFα-IRES-iCre virus that was used to infect Cre reporter cells to obtain expression of Cre recombinase (gray cells, left panel) and expression of TGFα using an EGFR reporter cell line (anti phosphotyrosine western, right panel).

FIG. 17 panel A is a schematic representation of the two lentiviruses employed, pTYF-TGFα-IRES-iCre and the control pTYF-GFP-IRES-iCre.

FIG. 17 panel B is a Kaplan-Meier survival plot demonstrating that co-expression of EGFR WT and TGFα in the context either of loss of Ink/Arf, and/or PTEN loci resulted in formation of lethal tumors. No tumors originated from expression of EGFR WT and control protein (green fluorescent protein, GFP). Viruses shown in panel A were injected to animals, which were monitored as a function of time for glioblastoma tumor formation.

FIG. 19 panel A shows mouse primary cultures of astrocytes and GBM cell cultures (GBM-1 and -2) that were grown the presence of increasing concentrations of NXD30001 for 36 hours. Cells were counted and plotted as percent of untreated cells.

FIG. 19 panel B shows cells treated with 250 nM of NXD30001 as a function of time. Viable cells were counted and plotted as percent of untreated cells.

FIG. 19 panel C shows cells exposed to 250 nM of NXD30001 were fixed, stained and extent of apoptosis reported as percentage of apoptotic cells relative to total number of cells as function of time. All data points are reported as mean values of triplicates and error bars represent standard deviation (S.D.) * and ** indicate P<0.0001 t-test. Data show that NXD30001 preferentially kills GBM-1 and GBM-2 cells compared to astrocyte control cells.

FIG. 19 panel D shows the depletion of the indicated HSP90 client proteins in GBM-1 and GBM-2 cultures and primary mouse astrocytes treated with 250 nM of NXD30001 for 24 hours. Strain GBM-1 cells co-express wild type and vIII EGFR, and strain GBM-2 cells express EGFR vIII.

FIG. 20 panel A is a set of photographs showing an advanced single-view 3D optical imaging (IVIS) BLI output for a single mouse imaged 14, 21 and 26 days post tumor induction to determine the time of treatment initiation (more than $10^7$ p/sec/cm$^2$/sr; arrow). Mice were dosed twice weekly at 100 mg/kg in vehicle for over 100 days. Control mice were given vehicle only. Note that BL imaging during treatment was not performed because luciferase is a client protein of HSP90. Animals were then re-imaged 36 days post treatment.

FIG. 20 panel B is a Kaplan-Meier analysis of survival rate of conditional EGFR mice treated with NXD30001 and otherwise identical control non-treated control non-treated conditional EGFR. Cohorts of mice were injected with Ad-CMV-Cre and were monitored for tumor formation by BLI as a function of time. Treatments were initiated and proceeded for about 100 days. Treated mice showed increased survival.

FIG. 20 panel C shows H&E stained paraffin embedded brain sections of NXD30001-treated (i and ii) mice and vehicle-treated (iii and iv) mice. Photographs ii and iv are inserts that are taken at higher magnification than photographs i and iii.

FIG. 23 panel A shows data collected from seven brain tumor-bearing animals were that were monitored as a function of time for bioluminescence. Tarceva (150 µg/kg) thrice weekly treatment was initiated after bioluminescence output reached more than $8 \times 10^6$ p/sec/cm$^2$/sr. Animal number 2148, which was observed to have been essentially cured by treatment, and was sacrificed 80 days post tumor initiation FIG. 23 panel B shows photographs of brain tissues processed for histological analysis. H&E stained sections of a control untreated mouse (left), and mouse number 2148 treated with Tarceva for 9.3 weeks (right).

FIG. 24 panel A shows an H&E stained section of a GBM brain tumor bearing animal that has had an ASO against STAT3 injected through convection enhanced delivery.

FIG. 24 panel B shows photographs that are taken at higher magnification of paraffin embedded sections H&E stained (left) and immunohistochemical analysis (IHC) of the ASO (right) demonstrating penetration of the ASO in tumor cells.

FIG. 24 panel C shows normal brain of non tumor-bearing control animal that has been treated with an ASO against STAT3 injected through convection enhanced delivery. Insert, IHC against the ASO (right) demonstrating penetration of the ASO in normal brain cells.

FIG. 25 panel A shows data obtained for GBM brain tumor-bearing animals.

FIG. 25 panel B shows data for normal mice.

DETAILED DESCRIPTION OF EMBODIMENTS

In methods herein, two Cre/lox conditional transgenic animals were constructed using human cDNAs encoding either wild type EGFR or GBM-observed mutant vIII. The transgenes are silenced in the animals until exposed to Cre recombinase, which is delivered through an intracranial injection of a virus capable of expressing Cre enzyme. Activation of EGFR (either wild type or mutant vIII) in the context of loss of INK4a-ARF and PTEN protein function leads to the development of GBMs.

These tumors and cells derived thereof were used to analyze pathway activations and genetic aberrations with the goals of establishing treatment susceptibilities that can be exploited therapeutically.

To understand EGFR signaling in GBM in order to better predict efficacy of targeted therapeutics, three pre-clinical models of GBM were developed herein based on overexpression of EGFR$^{WT}$ alone, co-expression of EGFR$^{WT}$ and EGFR$^{vIII}$ and expression of EGFR$^{vIII}$ alone. These models reflect naturally occurrening human GBMs. Using these models, the ectopic expression of EGFR (both WT and vIII) in adult CNS tissues, in the context of p16Ink4a/p19ARF and PTEN inactivation, was shown to lead to formation of GBMs de novo. EGFR-mediated tumor formation was shown herein to be accompanied by the activation of canonical and unexpected signaling pathways. Data herein show that the animal model systems can provide data regarding contributors to gliomagenesis and therapeutic treatment resistance in GBMs.

Clinical and Molecular Features of Glioblastoma Multiforme

Figure 1A:
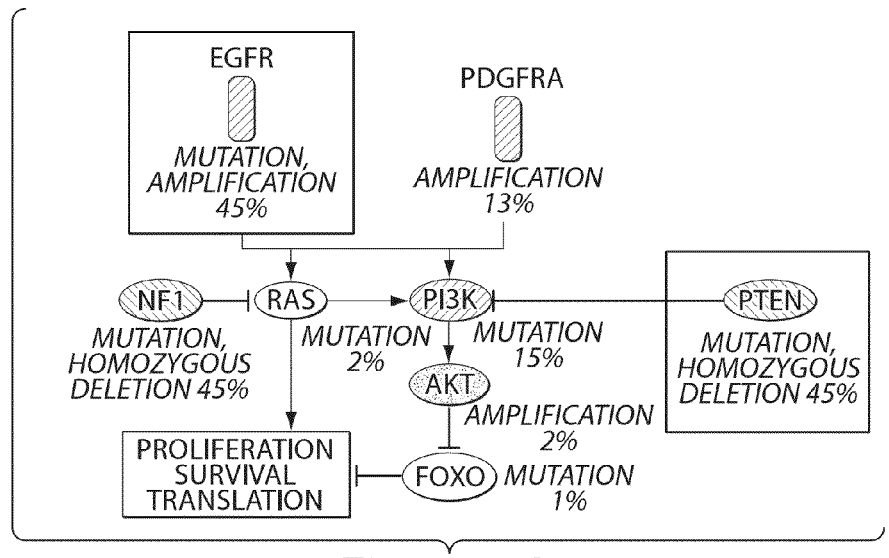
FIG. 1 is a drawing showing frequent genetic alterations found in GBMs in three signaling pathways. Proteins depicted in light gray ovals contain an activating genetic alteration (numerical alterations and methylation increased frequently are shown in deeper shades of gray). Proteins in dark grey ovals contain gene expression inactivating alterations (darker shades correspond to increased percent alteration). The genetic alterations engineered into the mouse model of GBM herein are shown in boxes.
Figure 1B:
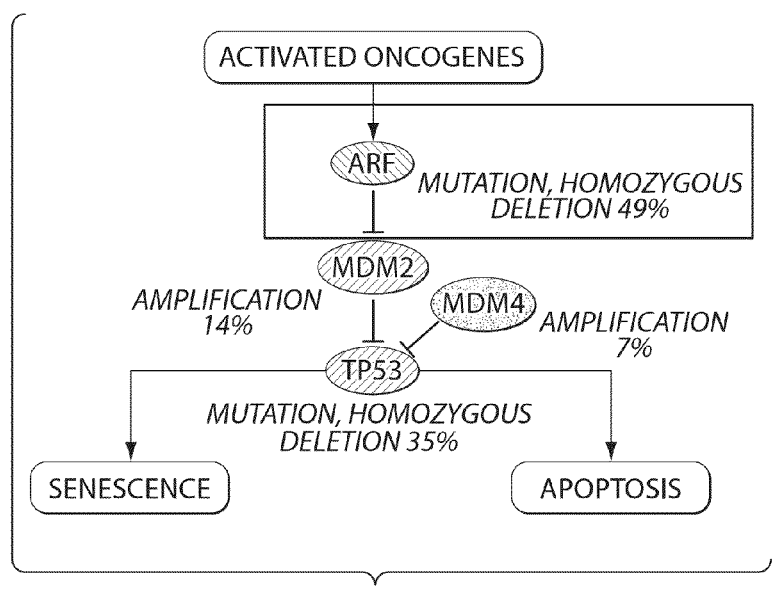
Figure 1C:
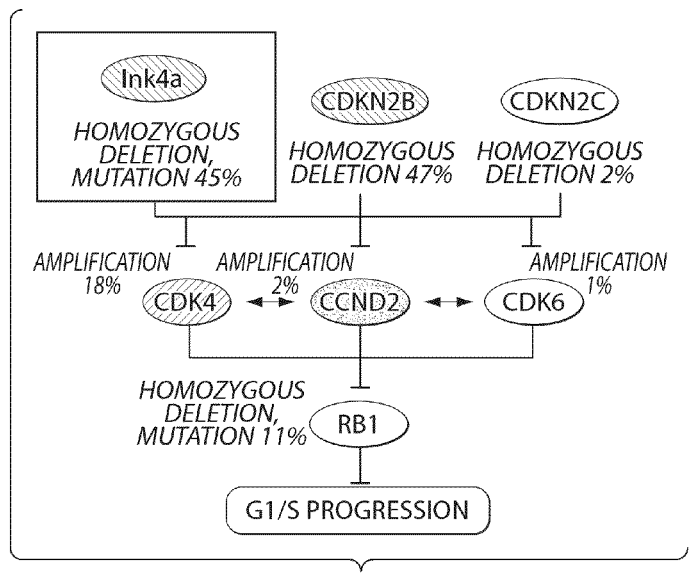

Genetically, GBMs are heterogeneous tumors with several signaling pathways differentially activated or silenced, and with converging and parallel complex interactions. The common form of glioblastoma are primary or de novo GBMs, tumors with no prior clinical manifestation at the time of diagnosis. There is a lack of knowledge in the molecular characteristics of the progression for this tumor. Large efforts, led by The Genome Atlas Consortium (TCGA) and the Ludwig Center for Cancer Genetica and Therapeutics, aimed at sequencing most of the GBM tumor genome identified copy number alterations, methylation patterns and gene expression profiling in over 100 GBM tumors. The data revealed a number of frequent genetic alterations in genes that are intrinsic to three significant signaling pathways. The TCGA study revealed that 88% of the receptor tyrosine kinase (RTK)/RAS/PI3K signaling is altered, 87% of the p53 signaling and 78% of the RB signaling pathways are altered in GBMs (FIG. 1; McLendon, R. et al. 2008 Nature 455:1061-1068). A common genetic aberration in GBMs is activation of receptor tyrosine kinases, of which, amplification and/or overexpression of EGFR is most common (Parsons, D. W. et al. 2008 Science 321:1807-1812; McLendon, R. et al. 2008 Nature 455:1061-1068; Nagane, M. et al. 2001 Cancer Lett 162 Suppl:S17-S21).

Concomitant with EGFR gene amplification is the occurrence of an intragenic in-frame deletion of exons 2 to 7 of the EGFR gene. This rearrangement product, known as EGFR$^{vIII}$, encodes a ligand-independent receptor, is constitutively activated and oncogenic (Kuan, C. T, et al. 2000 Brain Tumor Pathol 17:71-78; Kuan, C. T. et al. 2001 Endocr Relat Cancer 8:83-96; Pedersen, M. W. et al. 2001 Ann Oncol 12:745-760). Multiple inputs converge to nodal proteins during signal transmission (Voelzke, W. R. et al. 2008 Curr Treat Options Oncol 9:23-31; Huang, P. H. et al. 2007 Cell Cycle 6:2750-2754). A step towards identification of an efficient anti-cancer agent is by analyzing the activation status of signaling pathways members in a fully controllable system, that is a genetically engineered animal model.

EGFR Signaling

EGFR functions in cellular physiology mainly via its tyrosine kinase activity, and autophosphorylation and tyrosine phosphorylation of cellular substrate proteins is an early requisite step in transducing EGFR-mediated signals. EGFR protein includes twelve intracellular tyrosine phosphorylation sites. Phosphorylation of those residues results from an intermolecular reaction via a dimerization partner and, depending on the cellular context, through activation of intracellular tyrosine kinases such as Src and JAK-2, which directly phosphorylate the receptor on specific tyrosine residues (Yamauchi, T. et al. 1997 Nature 390:91-96; Biscardi, J. S. et al. 1999 J Biol Chem 274:8335-8343; Tice, D. A. et al. 1999 Proc Natl Acad Sci USA 96:1415-1420). Phosphorylated tyrosine residues provide specific docking sites for the SH2 or PTB domains of many intracellular signal transducer and adaptor proteins (Pawson, T. 2007 Curr Opin Cell Biol 19:112-116; Pawson, T. 2004 Cell 116:191-203). These phosphotyrosine dependent binding events lead to colocalization of these adaptors and signal transducer proteins with the receptor and result in assembly of multi-component signaling complexes.

Grb2, Shc and the Ras/MAPK Pathway

Genetic and biochemical data determined the signaling events that lead from the activation of EGFR to the activation of the proto-oncogene RAS and of the serine/threonine kinase MAPK. EGF-dependent Ras activation is mediated by the adaptor protein Grb2 (Lowenstein, E. J. et al. 1992 Cell 70:431-442), which is constitutively bound to the Ras GEF protein SOS. Normally localized to the cytosol, the Grb2:SOS complex interacts with activated (phosphorylated) EGFR via Grb2 SH2 domain interaction with EGFR Y1068 and Y1086 residues (Batzer, A. G. et al. 1994 Mol Cell Biol 14:5192-201). This interaction relocalizes the complex to the plasma membrane and facilitates interaction of membrane-associated Ras with SOS, resulting in Ras activation. Grb2 can also associate with EGFR indirectly by binding to EGFR-associated, tyrosine phosphorylated Shc proteins (Sasaoka, T. et al. 1994 J Biol Chem 269:32621-3265; Sakaguchi, K. et al. 1998 Mol Endocrinol 12:536-543). Through a series of intermediate kinases, including Raf-1 (Hallberg, B. et al 1994 J Biol Chem 269:3913-3916), activation of Ras leads to the phosphorylation, activation, and nuclear translocation of Erk-1 and Erk-2 where they can catalyze the phosphorylation of various nuclear transcription factors (Johnson, G. L. et al. 1994 Curr Opin Cell Biol 6:230-238) that are involved in the mitogenic control of growth factors (for reviews see Jun, T. et al. 1999 Sci STKE 1999:PE1; Liebmann, C. 2001 Cell Signal 13:777-785; Pouyssegur, J. et al. 2002 Biochem Pharmacol 64:755-763). Shc and Grb2 interact with numerous other signaling proteins (Fukazawa, T. et al. 1996 J Biol Chem 271:14554-14559; Meisner, H. et al. 1995 J Biol Chem 270: 25332-25335; Schlaepfer, D. D. et al. 1999 Prog Biophys Mol Biol 71:435-478; Xu, X. X. et al. 1998 Oncogene 16:1561-1569; De Sepulveda, P. et al. 1999 EMBO J 18:904-915; Harmer, S. L. et al. 1999 J Biol Chem 274:12183-12191; Pelicci, G. et al. 1995 Oncogene 11:899-907; Pomerance, M. et al. 1998 J Biol Chem 273:24301-24304; Xu, Y. et al. 1997 J Biol Chem 272:13463-13466).

Phospholipid Metabolism: PLCγ and the PI3K Survival Pathway

EGF stimulation of a cell has effects on cellular phospholipid metabolism. Enzymes involved in lipid metabolism that are directly activated by EGFR include phospholipase C-γ (PLCγ) and phosphatidylinositol-3-kinase (PI3K). PLCγ interacts directly with autophosphorylated EGFR at pY1173 and pY992 (Chattopadhyay, A. et al. 1999 J Biol Chem 274: 26091-26097) and is itself phosphorylated by EGFR kinase on pY771 and pY1254 (Wahl, M. I. et al. 1990 J Biol Chem 265:3944-3948; for a reviews of PLCγ see Kamat, A. et al. 1997 Cytokine Growth Factor Rev 8:109-117; Choi, J. H. et al. 2007 Adv Enzyme Regal 47:104-116). Once activated, PLCγ catalyzes the hydrolysis of PtdIns(4,5)-P2 to yield 1,2-diacylglycerol (DAG) and inositol 1,3,5-trisphosphate (IP3), which are second messenger molecules. Increases in levels of IP3 trigger calcium release from intracellular stores, which modulate a host of Ca2+-dependent enzymes. DAG is also a cofactor for activation of the serine/threonine kinase PKC. Through this PKC activation, EGFR can activate multiple signaling components, including the MAPK and JNK pathways (Marais, R. et al. 1998 Science 280:109-112; McClellan, M. et al. 1999 Exp Cell Res 246:471-479) and possibly the Na+/H+exchanger (Liaw, Y. S. et al. 1998 Am J Physiol 274:L665-672).

The phosphoinositide-3-kinases are mediators of a variety of cellular functions such as proliferation, survival, adhesion, and migration (Cantley, L. C. 2002 Science 296:1655-1657). PI3K catalyses the formation of PtdIns(3,4,5)-P3 (PIP3), a membrane requirement for activation of ser/thr kinases PDK1 and AKT (Nicholson, K. M. et al. 2002 Cell Signal 14:381-395) and a process antagonized by the action of the tumor suppressor gene PTEN. Activation of PI3K requires engagement of its p85 subunit SH2 domain (Carpenter, C. L. et al. 1993 J Biol Chem 268:9478-9483). The major binding partner of p85 is not the EGFR, but ErbB3 (Kim, H. H. et al. 1994 J Biol Chem 269:24747-24755; Ram, T. G. et al. 1996 Cell Growth Differ 7:551-561). Therefore, activation of PI3K observed in response to EGFR ligands is through the formation of EGFR/ErbB3 heterodimers. EGFR hetero-dimerization to other receptors tyrosine kinases may lead to PI3K activation in a similar fashion. Over activation of PI3K plays a key role in promoting growth and survival of cells from many tumor types (Franke, T. F. et al. 2003 Oncogene 22:8983-8998; Scheid, M. P. et al. 2001 Nat Rev Mol Cell Biol 2:760-768), including GBMs (Faivre, S. et al. 2006 Nat Rev Drug Discov 5:671-688; Newton, H. B. 2004 Expert Rev Anticancer Ther 4:105-128). Formation of pAKT promotes phosphorylation of many downstream effectors, including MDM2, p21/p27, Bad, ASK-1, FKHR, IkB, caspase-9, GSK3, FoxO, TSC2 and mTOR. mTOR plays a key role in the regulation of cellular catabolism, anabolism, proliferation, cell cycle control, autophagy, angiogenesis, and apoptosis.

mTOR activity in vitro is particularly high in cells with deficient PTEN function, including glioma cell lines (Newton, H. B. 2004 Expert Rev Anticancer Ther 4:105-128). In preclinical data in gliomas, PTEN-deficient tumors show enhanced sensitivity to mTOR inhibition, thus providing a rationale for clinical trials of mTOR inhibitors in GBMs (Neshat, M. S. et al. 2001 Proc Natl Acad Sci USA 98:10314-10319; Podsypanina, K. et al. 2001 Proc Natl Acad Sci USA 98:10320-10325). Phase II results of two clinical trials using temsirolimus (CCI-779) were negative, with no improvement in response rates, progression-free survival or overall survival (Chang, S. M. et al. 2005 Invest New Drugs 23:357-361; Galanis, E. et al. 2005 J Clin Oncol 23:5294-5304). These data indicate that CCI-779 has limited potential as a single therapeutic agent to treat GBMs.

Prompted by in vitro evidence of synergism between inhibitors of mTOR and EGFR (Rao, R. D. et al. 2005 Neoplasia 7:921-929), current clinical trials focus on combinations, including temsirolimus, everolimus (RAD001), or sirolimus (rapamycin) in combination with gefitinib, erlotinib, or AEE788. A phase I study combining gefitinib and sirolimus in malignant gliomas found a partial response in 2 of 34 patients, and disease remained stable in 13 of 34 patients (Reardon, D. A. et al. 2006 Clin Cancer Res 12:860-868). Preliminary results of a study using gefitinib and everolimus in unselected recurrent GBM patients showed responses (partial and minor) in 31% of patients using modified radiographic criteria. However, overall median survival and progression-free survival were not different from historical controls (Lassman, A. B. et al. 2006 N Engl J Med 354:525-526). The present inventor has perceived the need for a priori molecular characterization, and an investigation to determine the nature of the mTOR complex that is active in GBMs and the circumstances of activation.

mTOR activity is found in two different multiprotein complexes, known as mTORC1 and mTORC2 (Guertin, D. A. et al. 2007 Cancer Cell 12:9-22). Each complex is capable of functioning in the various physiological roles that have been attributed to mTOR. Further, mTORC1 is Rapamycin sensitive whereas mTORC2 is insensitive to the drug.

Associated with these mutations are loss of function mutations of tumor suppressor gene Ink4a/Arf locus. The INK4a-ARF tumor suppressor locus encodes two proteins, p16INK4a and ARF (p14ARF in humans and p19ARF in mice), which modulate activity of two additional tumor suppressor genes, the RB and p53 proteins (Ohtani, N. et al. 2004 J Med Invest 51:1.46-153; Sharpless, N. E. 2004 Exp Gerontol 39:1751-1759; Sharpless, N. E. et al. 2004 J Clin Invest 113:160-168). This locus is frequently mutated in human GBMs with approximately 60% of GBMs harboring a deletion of this locus (Ushio, Y. et al. 2003 Front Biosci 8: 281-288). In the GBMs that preserve intact INK4a-ARF alleles, mutations in other components of the p53 and RB pathways have been observed (Ushio, Y. et al. 2003 Front Biosci 8: 281-288; Newcomb, E. W. et al. 1998 Brain Pathol 8:655-667; Nozaki, M. et al. 1999 Neuro-oncol 1:124-137). Data observed using primary mouse astrocytes lacking the Ink4a-Arf locus indicate that a role of INK4a-ARF deficiency is to immortalize cells by preventing entry into growth arrest and senescence (Holland, E. C. et al. 1998 Genes Dev 12:3644-3649; Uhrbom, L. et al. 1997 Oncogene 15:505-1435). Furthermore, the immortalized cells acquire features of undifferentiated glial cells such as progenitor-like morphology, expression of nestin (a CNS stem cell marker) and loss of expression of astrocyte-specific marker protein GFAP (glial fibrillary acidic protein) (Holland, E. C. et al. 1998 Genes Dev 12:3644-3649).

Phosphoproteome

Proteomics-based experiments have demonstrated correlative relationships between specific protein expression levels and histopathological classification and survival (Chumbalkar, V. C. et al. 2005 Proteomics 5:1167-1177; Iwadate, Y. et al. 2004 Cancer Res 64:2496-2501; Odreman, F. et al. 2005 J Proteome Res 4:698-708; Schwartz, S. A. et al. 2005 Cancer Res 65: 7674-7681). Proteomic-based prognosis of brain tumor patients has been approached using a variety of technologies, including direct-tissue matrix-assisted laser desorption ionization mass spectrometry, signaling pathway activation (Dasgupta, B. et al. 2005 Cancer Res 65:2755-27560; Hiratsuka, M. et al. 2003 Biochem Biophys Res Commun 309:558-566; Chakravarti, A. et al. 2001 Clin Cancer Res 7:2387-2395), glioma cell invasion (Goplen, D. et al. 2006 Cancer Res 66:9895-9902; Zhou, L. et al. 2006 Neurosci Lett 401:59-64), response to chemotherapeutic agents (Iwadate, Y. et al. 2005 Int J Oncol 26:993-998), and viewing different areas of a tumor radiographically (Hobbs, S. K. et al. 2003 J Magn Reson Imaging 18:530-536).

These technologies have led to global analyses of protein phosphorylation, and its dynamics under various stimuli, including various signaling cascades and their intricate organization (White, F. M. 2008 Curr Opin Biotechnol 19:404-409). Methods for enrichment of phosphoproteins in conjunction with improvements in mass spectrometry can characterize protein phosphorylation on a large scale, showing functional links between global protein phosphorylation patterns and tumor cell behavior as a function of receptor tyrosine kinase (RTK) activation, including EGFR (Huang, P. H. et al. 2007 Cell Cycle 6:2750-2754; Kumar, N. et al. 2007 PLoS Comput Biol 3:e4; Chen, W. G. et al. 2004 Expert Rev Proteomics 1:343-354; Rikova, K. et al. 2007 Cell 131:1190-1203). By global mapping of phosphorylation sites on nuclear proteins from HeLa cells using mass spectrometry, over 2000 sites of phosphorylation on 967 nuclear proteins were identified (Beausoleil, S. A. et al. 2004 Proc Natl Acad Sci USA 101:12130-12135). Similar efforts have been conducted in the developing mouse brain (Ballif, B. A. et al. 2004 Mol Cell Proteornies 3:1093-1101), in rat liver (Moser, K. et al. 2006 J Proteome Res 5:98-104), mouse post synaptic densities (Trinidad, J. C. et al. 2006 Mol Cell Proteomics 5:914-922) and forebrain synaptosomes (Collins, M. O. et al. 2005 J Biol Chem 280:5972-5982) in human cell lines under various treatments (Beausoleil, S. A. et al. 2004 Proc Natl Acad Sci USA 101:12130-12135; Brill, L. M. et al. 2004 Anal Chem 76:2763-2772; Cantin, G. T et al. 2006 J Proteome Res 5:127-134; Kim, S. et al. 2002 Mol Cancer Ther 1:1229-1236; Rush, J. et al. 2005 Nat Biotechnol 23:94-101; Tao, W. A. et al. 2005 Nat Methods 2:591-598; Zhang, Y. et al. 2005 Mol Cell Proteomics 4:1240-1250), and in *S. cerevisiae* (Ficarro, S. B. et al. 2002 Nat Biotechnol 20:301-305; Gruhler, A. et al. 2005 Mol Cell Proteomics 4:310-327; Peng, J. et al. 2003 Nat Biotechnol 21:921-926).

Phosphorylation is generally a sub-stoichiometric reaction, i.e., only a small fraction of a protein is phosphorylated and concomitant low abundance phosphoproteins are involved in regulatory processes such as signal transduction. Many proteins are phosphorylated on different sites, thus phosphoproteins exist in different forms, which can complicate analysis of dynamic phosphorylation events.

RNAi Library Screens

Global genome shRNA library RNAi screens have been performed to identify key genes driving various phenotypes (Kassner, P. D. 2008 Comb Chem High Throughput Screen 11:175-184; Micklem, D. R. et al. 2007 Curr Pharm Biotechnol 8:337-343; Paddison, P. J. 2008 Curr Top Microbiol Immunol 320:1-19; Guan, H. et al. 2008 Adv Biochem Eng Biotechnol 110:1-24; Wolters, N. M. et al. 2008 Cell Death Differ 15:809-819; Iorns, E. et al. 2007 Nat Rev Drug Discov 6:556-568; Chen, M. et al. 2007 Expert Rev Mal Diagn 7:281-291; Janitz, M. et al. 2006 Handb Exp Pharmacol 97-104; Ito, M. et al. 2005 FEBS Lett 579:5988-5995). Up to 50 to 100 individual genes can be targeted with a smaller custom or gene-restricted library (Tyner, S. W. et al. 2008 Blood 111:2238-2245; Morgan-Lappe, S. et al. 2006 Oncogene 25:1340-1348). For example, in a MYC driven lymphoma model, shRNA library screens have shown many molecular mediators of lymphomagenesis and resistance to therapeutic agents (Dickins, R. A. et al. 2005 Nat Genet 37:1289-1295; Hemann, M. T. et al. 2005 Nature 436:807-811; He, L. et al. 2005 Nature 435:828-833; Hemann, M. T. et al. 2004 Proc Natl Acad Sci USA 2004; 101:9333-9338; Hemann, M. T. et al. 2003 Nat Genet 33:396-400; Mavrakis, K. J. et al. 2008 Genes Dev 22:2178-2188). Similarly, an RNAi-mediated knockdown screen of the entire kinome showed potential therapeutic targets in leukemia and synthetic lethality of Akt-cooperating kinases (Tyner, J. W. et al. 2008 Blood 111:2238-2245; Morgan-Lappe, S. et al. 2006 Oncogene 25:1340-1348).

Targeted Therapy

A first step in the process of developing targeted therapy is identification of targets that constitute key master promoters of oncogenesis (Weinstein, I. B. et al. 2008 Cancer Res 68:3077-3080). In humans, clues for identifying potential targets in the highly complex genetic events are provided by the establishing an association between a molecular abnormality and its prognosis. Clinical trials based on this type of retrospective association approach have so far been disappointing, including in gliomas (Omura, A. M. et al. 2007 Mol Cancer Ther 6:1909-1919; Chakravarti, A. et al. 2007 Curr Oncol Rep 9:71-79; Gilbert, M. R. 2007 Curr Oncol Rep 9:49-54). There are more than 150 different clinical trials identified on the government clinical trials website, however, few are based on prior knowledge of specific molecular characteristics of the tumor.

Efforts aimed at linking EGFR expression patterns and differential prognosis in GBMs have given rise to conflicting results (Chakravarti, A. et al. 2005 Int J Radiat Oncol Biol Phys 62:318-327; Heimberger, A. B. et al. 2005 Clin Cancer Res 11:1462-1466; Quan, A. L. et al. 2005 Int J Radiat Oncol Biol Phys 63:695-703; Shinojima, N. et al. 2003 Cancer Res 63:6962-6970; Zhu, A. et al. 1996 Int J Radiat Oncol Biol Phys 34:809-815). Nevertheless, several strategies to target the EGF receptor include use of monoclonal antibodies against the wild type and mutated versions of the receptor, bispecific antibodies, toxin-linked conjugates, vaccine therapies, and small-molecule tyrosine kinase inhibitors (TKIs). Results of the first EGFR TKI phase II trials for two inhibitors, gefitinib (ZD-1839) and erlotinib (OSI-774), in recurrent and newly diagnosed GBMs demonstrated that although some responses were obtained, the overall efficacy of these compounds in unselected patients was minimal when compared with historical data (Cloughesy, T. F. et al. 2006 J Clin Oncol 24:3651-3656; Franceschi, E. et al. 2007 Br J Cancer 96:1047-1051; Rich, J. N. et al. 2004 J Clin Oncol 22:133-142; Wen, P. Y. et al. 2006 Clin Cancer Res 12:4899-4907; Wong, E. T. et al. 1999 J Clin Oncol 17:2572-2578; Yung, W. K. et al. 2000 Br Cancer 83:588-593). EGFR phosphorylation and downstream signaling were not markedly inhibited after treatment initiation (Lassman, A. B. et al. 2005 Clin Cancer Res 11:7841-7850). Pharmacokinetic analysis of tissue penetration demonstrated that, with some tumors, only minimal intratumoral drug concentrations were achieved (Lassman, A. B. et al. 2005 Clin Cancer Res 11:7841-7850).

Efficiency of receptor inhibition is context dependent and methods and receptors are provided herein for molecular characterization of tumors vis-à-vis drug response. The methods herein constitute a direct solution to malignant brain cancer and many other cancers given the high level of parallelism in the signaling pathways employed by various oncogenic cues to drive cancer cells forward.

Methods herein use clinically relevant protein targets that have a significant function for GBM tumor cell survival and resistance to therapy in a preclinical mouse model, to identify compounds that modulate the activity and/or expression levels of pertinent protein targets and their pathways in humans, Successful targeting of genes that have been shown to have function in survival of GBM cells will have a direct impact on cancer treatment.

Therapeutic RNA Interference (RNAi) Agents

Because cancer arises through an imbalance in regulation of essential genes involved in cell growth and cell death programs, in general, gene products regulating these phenomena are difficult to target with small molecules. Pharmaceutical companies commonly consider these genes to be nontargetable. The possibility of using RNAi, which specifically silences genes at the level of mRNA cleavage independent of protein structure and cellular location, is very promising (Novina, C. D. et al. 2004 Nature 430:161-164). RNAi is an evolutionarily conserved biological process for specific silencing of gene expression. Synthetic siRNAs are suitable for post-transcriptional gene silencing in cells and animals as they are characterized by robust potency and specificity and absence of interferon responses (McManus, M. T. et al. 2002 Rna 8:842-850). The activities of siRNAs could thus offer a general approach to the treatment of most cancers.

In mammals, siRNAs are likely recognized by the biochemical machinery responsible for the activities of microRNAs (miRNAs), which are encoded in genomic DNA (Bartel, D. P. 2004 Cell 116:281-297; Bartel, D. P. et al. 2004 Nat Rev Genet 5:396-400). Every cell expresses miRNAs and thus it is highly likely that every tumor cell will express the biochemical machinery necessary for siRNA processing and activities. In fact, the presence of specific miRNAs in various tumors strongly suggests that such biochemical machinery is available for siRNA function (for recent reviews on miRNA and cancer see (Calin, G. A et at 2006 Nat Rev Cancer 6:857-866; Xu, W. et al. 2007 Chin Med J (Engl) 120:996-999; Fabbri, M. et al. 2007 Expert Opin Biol Ther 7:1009-1019; Mathupala, S. P. et al. 2007 DNA Cell Biol 26:301-310). Unlike earlier antisense technologies for the treatment of cancers, siRNAs use endogenous catalytic machinery to efficiently silence genes. In fact, RISC complexes can target the cleavage of multiple mRNAs making the RNAi process catalytic rather than stoichiometric. This biochemical feature permits silencing of multiple and different genes at once within a given cell and also reduces the requirement for the presence of relatively high levels of siRNAs in a cell to elicit silencing. siRNAs have been transfected directly into cells to silence a gene using a variety of transfection reagents. Alternatively, siRNAs are introduced to cells through the use of gene vectors that have been designed to encode hairpins that are processed to siRNAs for silencing. Such studies have already identified a number of target genes which, when silenced in culture can induce the death of tumor cells relative to normal cells (Behlke, M. A. 2006 Mol Ther 13:644-670; Dykxhoorn, D. M. et al. 2003 Nat Rev Mol Cell Biol 4:457-467; Kuhn, R. et al. 2007 Handb Exp Pharmacol 178:149-176).

Delivery of siRNA molecules into various organs has demonstrated specific knockdown of artificially introduced reporter genes such as GFP or firefly luciferase (Bertrand, J. R. et al. 2002 Biochem Biophys Res Commun 296:1000-1004; Bollerot, K. et al. 2006 Dev Dyn 235:105-114; De Jonge, J. et al. 2006 Gene Ther 13:400-411; Golzio, M. et al. 2005 Gene Ther 12:246-251; Hassani, Z. et al. 2005 J Gene Med 7:198-207; Howard, K. A. et al. 2006 Mol Ther 14:476-484; Lewis, D. L. et al. 2002 Nat Genet 32:107-108; McCaffrey, A. P. et al. 2002 Nature 418:38-39; Sato, Y. et al. 2005 Transplantation 79:240-243; Takahashi, Y. et al. 2005 J Control Release 105:332-343), or endogenous target genes such as Fas, Ins2, mdr1a/1b, APOB, TRb1+2, and CD31 (Bradley, S. P. et al. 2005 Transplant Proc 37:233-236; Guissouma, H. et al. 2006 Neurosci Lett 406:240-243; Heidel, J. D. et al. 2004 Nat Biotechnol 22:1579-1582; Matsui, Y. et 1. 2005 Pharm Res 22:2091-2098; Santel, A. et al. 2006 Gene Ther 13:1360-1370; Santel, A. et al. 2006 Gene Ther 13:1222-1234; Zimmermann, T. S. et al. 2006 Nature 441:111-114).

siRNA-mediated RNAi is used herein for therapeutical purposes beyond the detection of the downregulation of an endogenous target gene. Examples herein show treatment of GBM cancer with siRNAs demonstrate inhibition of tumor growth.

Previously targeted cancers and the target genes include pancreatic adenocarcinoma with CEACAM6 (Duxbury, M. S. et al. 2004 Ann Surg 240:667-675), blc-2 (Ocker, M. et al. 2005 Gut 54:1298-308) and mutant k-ras (Sun, D. et al. 2006 Biotechniques 41:59-63); bladder cancer with Survivin (Beard, C. et al. 2006 Genesis 44:23-28) and PLK-1 (135. Nogawa, M. et al. 2005 J Clin Invest 115:978-985); prostate carcinoma with bcl-2 (Yano, J. et al. 2004 Clin Cancer Res 10:7721-7726), Raf-1 (Pal, A. et al. 2005 Int J Oncol 26:1087-1091), and VEGF (Takei, Y. et al 2004 Cancer Res 64:3365-3370); breast cancer with c-raf (Chien, P. Y. et al. 2005 Cancer Gene Ther 12:321-328), Raf-1 (Leng, Q. et al 2005 Cancer Gene Ther 12:682-690), and RhoA (Pille, J. Y. et al. 2006 Hum Gene Ther 17:1019-1026); melanoma with c-myc, MDM2 and VEGF (Song, E. et al. 2005 Nat Biotechnol 23:709-717); cervical cancer with HPV E6+E7 (Fujii, T. et al. 2006 Int J Oncol 29:541-548) and ovarian cancer with FAK (Halder, J. et al. 2006 Clin Cancer Res 12:4916-4924) and HER-2 (Urban-Klein, B. et al. 2005 Gene Ther 12:461-466); glioblastoma with Pleiotrophin (Grzelinski, M. et al. 2006 Hum Gene Ther 17:751-766). In these studies, siRNAs were dosed using various regimens either locally or systemically, and various levels of knock down of the target genes were achieved and a certain level of therapeutic efficacy was reported.

However, to date, siRNAs have not yet been shown to treat tumors that arise de novo in animals let alone in humans. Application of siRNAs in vivo requires careful development of formulations, dosages, and identification of optimal modes of administration. Systemic administration requires substantial quantities of materials and extensive chemical modifications of the RNA backbone to shield the siRNAs from the actions of circulating nucleases. Local administration of siRNAs, which overcomes stability issues to a certain extent, may not always be clinically feasible. For CNS delivery however, neurosurgical procedures are common practice and are not perceived as problematic. Promising technologies such as convection enhanced delivery and/or those associated with the uses and applications of multifunctional nanoparticles for efficient therapeutic siRNA-mediated gene silencing, are applied to these hurdles (Gilmore, I. R. et al. 2006 Curr Drug Deliv 3:147-145; Hall, W. A. et al. 2003 Neurosurg Focus 14:e2; Hall, W. A. et al. 2006 Neurosurg Focus 20:E10; Raghavan, R. et al. 2006 Neurosurg Focus 20:E12; Vandergrift, W. A. et al. 2006 Neurosurg Focus 20:E13; Sampson, J. H. et al. 2006 Neurosurg Focus 20:E14; Kunwar, S. et al. 2006 Neurosurg Focus 20:E15). In the CNS, the blood brain barrier represents a major problem for tissue dissemination of systemically administered therapeutics. In GBMs, it is known that intratumoral blood vessels are somewhat leaky thus facilitating drugs penetration. Further, GBM cells have high capacity to migrate distantly from the bulk tumor mass into healthy parenchyma having intact capillaries. Targeting siRNAs to transcapillary movement using peptide conjugation (sequence derived from rabies virus-(Kumar, P. et al. 2007 Nature 448:39-43) can deliver therapeutically active siRNAs through the healthy blood brain barrier.

Many genes that contribute to the biological programs in tumor cells are difficult to target with small molecules. Only a handful of well-characterized small chemical inhibitors of signaling proteins have been identified, most of which have failed in clinical trials. Many signaling molecules lack enzymatic activity, hence are poor targets for chemical therapeutic approaches. The challenges include pinpointing the appropriate target/gene using stringent validation parameters and techniques and developing techniques and methodologies to efficiently deliver chemically fortified potent siRNAs to tumor-bearing animals. The examples herein offer a direct attack on those challenges using siRNAs for therapeutic purposes.

Cancer Relevance

Cancer is for the most part remains incurable, and most treatments are merely palliative. Targeted therapy has recently proven to be very efficacious in certain cancers. The goals of examples herein are to determine genetic contributors (i.e. genes) to maintenance and growth of GBM and to inhibit these genes using a targeting methodology, and provide methods of delivering potent therapeutic agents to subjects having a pre-clinical mouse model of cancer with a focus on malignant brain tumors. The mouse models provided here are genetically engineered for accuracy and relevance to the human cancers. Data obtained herein show that these models lead to a better understanding of the disease at the molecular level and consequent clinical advancement.

Pharmaceutical Compositions

In one aspect of the present invention, pharmaceutical compositions are provided, that comprise at least one of a modulator of expression or activity of a protein kinase, for example, an shRNA, or a compound isolated from a chemical library using one of the screens herein, and optionally further comprise a pharmaceutically acceptable carrier. In certain embodiments, these compositions optionally further comprise one or more additional therapeutic agents. In certain embodiments, the additional therapeutic agent or agents are selected from the group consisting of anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, and hyaluronic acid.

As used herein, the feint "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Therapeutically Effective Dose

In yet another aspect, according to the methods of treatment of the present invention, the tumor formation is suppressed by contacting said cells with a pharmaceutical composition, as described herein. Thus, the invention provides methods for the treatment of a cancer associated with a particular growth factor receptor and/or variant and/or ligand comprising administering a therapeutically effective amount of a pharmaceutical composition comprising active agents that include at least one of a modulator of expression or activity of a growth factor receptor or ligand for such receptor to a subject in need thereof, in such amounts and for such time as is necessary to achieve the desired result. It will be appreciated that this encompasses administering an inventive pharmaceutical as a therapeutic measure to promote regression of a cancer or prevent further development or metastasis, or as a prophylactic measure to minimize complications associated with development of a tumor or cancer. In certain embodiments of the present invention a "therapeutically effective amount" of the pharmaceutical composition is that amount effective for preventing further development of a cancer or transformed growth. The compositions, according to the method of the present invention, may be administered using any amount and any route of administration effective for prevention of development of a cancer. Thus, the expression "amount effective for a modulator of expression or activity of a gene", as used herein, refers to a sufficient amount of composition to prevent or retard development of a cancer, and even cause regression of a cancer or solid tumor. The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., tumor size, member and location; age, weight and gender of the patient; diet, time and frequency of administration; drug combinations; reaction sensitivities; and tolerance/response to therapy. Long acting pharmaceutical compositions might be administered every 3 to 4 days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of active agent which ameliorates the symptoms or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it is expressed as the ratio, LD50/ED50. Pharmaceutical compositions which exhibit large therapeutic indices are preferred. The data obtained from cell culture assays and animal studies is used in formulating a range of dosage for human use.

Administration of Pharmaceutical Compositions

After formulation with an appropriate pharmaceutically acceptable carrier in a desired dosage, the pharmaceutical compositions of this invention can be administered to humans and other mammals topically (as by powders, ointments, or drops), orally, rectally, parenterally, intracisternally, intravaginally, intraperitoneally, bucally, ocularly, or nasally, depending on the severity and location of the wound being treated.

Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous infections may be treated with aqueous drops, a mist, an emulsion, or a cream. Administration may be therapeutic or it may be prophylactic. Prophylactic formulations may be present or applied to the site of tumors, or to sources of tumors. The invention includes surgical devices, audiological devices or products which contain disclosed compositions (e.g., gauze bandages or strips), and methods of making or using such devices or products. These devices may be coated with, impregnated with, bonded to or otherwise treated with a disclosed composition.

The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to the agents of this invention, excipients such as lactose, talc, silicic acid, aluminum hydroxide, calcium silicates, polyamide powder, or mixtures of these substances. Sprays can additionally contain customary propellants such as chlorofluorohydrocarbons.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Uses of Pharmaceutical Compositions

As discussed above and described in greater detail in the Examples herein, at least one of a modulator of expression or activity of a gene associated with tumor formation is useful to prevent development or metastasis of a cancer condition. In general, it is believed that these modulators of expression or activity of a gene will be clinically useful in preventing further growth of a particular cancer type, including but not limited to the skin cancer; the retinoblastoma; colon cancer and other such conditions arising from the lining of the gastrointestinal tract; lung cancer; renal carcinoma and other tumors arising from the inner surface of kidney tubules; leukemias and lymphomas and such disorder of blood; cervical cancer including those associated with various strains of papilloma virus; brain tumors; and cancers of the uterus, of the vagina, of the urethra, or of the respiratory tract.

It will be appreciated that the diagnostic, prognostic and therapeutic methods encompassed by the present invention are not limited to treating conditions in humans, but may be used to treat similar conditions in any mammal including but not limited to bovine, canine, feline, caprine, ovine, porcine, murine, and equine species. When treating tumors in a given species, it is preferred, but not required, that the shRNA have a nucleotide sequence that is substantially identical to that as it occurs naturally in the species, and that a modulator of expression or activity of a protein kinase be shown to function for the gene as it occurs naturally in the species.

Genes associated with tumor formation that encode kinases such as serine/threonine kinases or tyrosine kinases are not limited to association with particular cancers, but also are known with respect to etiology of such conditions as chronic and acute inflammation, arthritis, osteoarthritis, septicemia, autoimmune diseases (e.g., inflammatory bowel disease, psoriasis), transplant rejection, graft vs. host disease, infection, stroke, ischemia, acute respiratory disease syndrome, renal disorders, restenosis, brain injury, AIDS, metabolic and other bone diseases (e.g., osteoporosis), cancer (e.g., lymphoproliferative disorders), atherosclerosis, and Alzheimers disease, among others, and diagnostic assays for such conditions. Accordingly the methods herein are envisioned as applicable to these conditions also.

A portion of this work was published in papers entitled "Oncogenic EGFR signaling cooperates with loss of tumor supressor gene functions in gliomagenesis" by Haihao Zhu, Jaime Acquaviva, Pranatartiharan Ramachandran, Abraham Boskovitz, Steve Woolfenden, Rolf Pfannl, Roderick T. Bronson, John W. Chen, Ralph Weissleder, David E. Housman, and Al Charest, published Feb. 24, 2009 Proc Natl Acad Sci USA 106: 2712-2716, and "A Cre/LocP conditional luciferase reporter transgenic mouse for bioluminescence monitoring of tumorigenesis" by Steve Woolfenden, Haihao Zhu, and Al Charest published Jul. 14, 2009 Genesis 47:659-666, which are hereby incorporated herein by reference in its entirety.

The invention having been fully described, the following examples and claims are exemplary and are not intended to be further limiting. The contents of all references cited are hereby incorporated herein by reference.

EXAMPLES

Example 1

EGFR Conditional Transgenic Mice

Cre/Lox-mediated conditional expression of the human EGF receptors (wild type and vIII) was achieved by targeted knock in of CAGGS-floxed stop cassette EGFR cDNA mini genes into the mouse collagen 1α1 gene locus as described herein. Germ line transmitted EGFR$^{WT}$ and EGFR$^{vIII}$ founder males were mated to InkD2/3 (Serrano, M. et al. 1996 Cell 85:27-37) and conditional PTEN knock out strains (Lesche, R. et al. 2002 Genesis 32:148-149). The combinations of strain indicated in examples herein were produced by cross-breeding. Activation of EGFR expression in the brain was accomplished by stereotactic intracranial injections of an adenovirus expressing Cre recombinase under the CMV promoter. Mouse procedures were performed in accordance with Tufts University's recommendations for the care and use of animals and were maintained and handled under protocols approved by the Institutional Animal Care and Use Committee.

The strategy for the construction of the EGFR-based genetically engineered mouse strains was as follows: wild-type and vIII isoforms of human EGFR cDNAs were inserted in the CAGGS-Col1α1 vector plasmid. After DNA sequencing for integrity, plasmid DNAs were coelectroporated along with pCAGGS-Flpe plasmid into C2 ES cells. Clonal selection was achieved using hygromycin, and individual clones were screened by Southern blot hybridization (Ausubel, F. et al. 2001 in Current Protocols in Molecular Biology, Wiley, New York) using probes according to Beard, C. et al. 2006 Genesis 44:23-28. ES clones with properly locked-in transgenes in the Col1α1 locus were used to produce chimeric mice, which were mated to produce founder animals. Germline-transmitted EGFRWT and EGFRvIII founder males were mated to InkΔ2/3 (Serrano, M. et al. 1996 Cell 85:27-37) and conditional PTEN knockout strains (Lesche, R. et al. 2002 Genesis 32:148-149).

Homozygous null mice for the Ink4a/Arf locus were observed to develop lymphomas and subcutis sarcomas at a median age of 30 weeks (Serrano, M. et al. 1996 Cell 85:27-37); nonrecombined PTEN2lox mice were observed to be normal and viable; and CNS-specific deletion of PTEN alone was observed to be inconsequential. In addition, targeting into the 3' region of Col1α1 gene was not found to produce an observable phenotype. Several other minigenes to that locus were also knocked out without phenotypic consequences of integration. Compound EGFR transgenic control mice that were not exposed to Cre recombinase did not exhibit phenotypic features that are consistent with spontaneous tumor formation.

The EGFR transgenic strains were genotyped using the following primer set: Col frt A1 (5' GCA CAG CAT TGC GGA CAT GC3'; SEQ ID NO: 1), Col frt B (5'CCC TCC ATG TGT GAC CAA GG3'; SED ID NO: 2), and Col frt C (5'GCA GAA GCG CGG CCG TCT GG3': SEQ ID NO: 3) for the collagen 1α1 locus genotype. The EGFR alleles were genotyped as appropriate using Flp1N 4230-4250 (5'CCC CCT GAA CCT GAA ACA TAA3'; SEQ ID NO: 4) with hEGFR-390rev (5'ATG GGC AGC TCC TTC AGT CCG3'; SEQ ID NO: 5) or hEGFR-1110rev (5'TAA ATG CCA CCG GCA GGA TG3'; SEQ ID NO: 6) for the WT or vIII allele, respectively. The PCR cycling parameters for the genotypes are 94° 5 min, 35 cycles at 94° C. for 30 sec, 55° C. for 30 sec, and 72° C. for 30 sec followed by a 10-min extension at 72° C. Genotyping protocols for InkΔ2/3 knockout animals and conditional PTEN knockout strains were carried out according to Serrano, M. et al. 1996 Cell 85:27-37; Lesehe, R. et al. 2002 Genesis 32:148-149.

Homozygous mice with 2 copies of EGFR wild-type knockin alleles are indicated as EGFR$^{WT/WT}$ and hemizygous with one copy as EGFR$^{WT/+}$. Animals with one or both copies of the knockin allele of EGFRvIII are indicated as EGFR$^{vIII/+}$ and EGFR$^{vIII/vIII}$. Mice with one copy each of EGFR$^{WT}$ and vIII knockin alleles are indicated as EGFR$^{WT/vIII}$.

Example 2

Stereotactic Injections

Adult animals (3 months of age and older) of the indicated genotype were anesthetized with an IP injection of ketamine/ xylazine (ketamine 100-125 mg/kg, xylazine 10-12.5 mg/kg. The animals were mounted in a Stoelting stereotaxic frame (Harvard Apparatus Inc.) with nonpuncturing ear bars. The incision site was shaved and sterilized with betadine surgical scrub, and a single incision was made from the anterior pole of the skull to the posterior ridge. A 1-mm burr hole was drilled at the stereotactically defined location of the striatum (2.1 mm rostral to the bregma, 1.5 mm lateral to the midline, and at 2 mm depth to the pia surface) and either a HA Hamilton syringe or a pulled glass pipette mounted onto a Nanoject II injector (Drummond Scientific Company) was used to inject the adeno-CMV Cre virus (Gene Transfer Vector Core, University of Iowa, Iowa City, Iowa) at a rate of 0.1 µl/min. Following retraction of the syringe or pipette, the burr hole was filled with sterile bone wax, the skin drawn up and sutured, and the animal placed in a cage with a padded bottom atop a surgical heat pad until ambulatory.

Example 3

Primary Cultures

Primary cultures of tumors or newborn mice astrocytes were established as follows: tumors or P0 neonate cortices were excised and minced in 0.25% trypsin (wt/vol) 1 mM EDTA and allowed to disaggregate for 15 min at 37° C. The resulting cell suspension was then strained through a 70-µm cell strainer (Falcon). The single suspension of cells was washed in PBS twice and plated on 0.2% gelatin-coated tissue culture plates. Cells were fed every 24 hr with fresh medium that consisted of DMEM supplemented with 10% heat-inactivated FBS and antibiotics. The primary cultures of astrocytes were routinely stained for markers of astrocytic lineages by immunofluorescence.

Example 4

Immunoblotting

Protein extract were electrophoretically separated on SDS/polyacrylamide gels then transferred to Immobilon-P membranes (Millipore). Western blots were performed as follows: cell lysates were prepared using radioimmunoprecipitation (RIPA) buffer supplemented with 5 mM $Na_3VO_4$ (freshly made) and Complete™ protease inhibitor mixture (Roche). Total cell lysate (40 µg) was separated by SDS-PAGE and electrotransfered to polyvinylidene fluoride (PVDF) membrane (Immobilon P; Millipore). Blots were blocked in Tris-buffered saline 0.1% (vol/vol) Tween-20 (TBS-T), 1% (wt/v) BSA, and 5% (wt/v) nonfat dry milk (Bio-Rad) for 1 hr on a shaker. Primary antibodies were added to blocking solution at 1:1,000 dilution and incubated overnight at 4° C. on a shaker. Blots were washed several times with TBS-T BSA, and secondary antibodies were added at 1:10,000 dilution into TBS-T BSA and incubated for 1 hr at room temperature on a shaker. Enhanced chemiluminescence (ECL) reactions were performed as described by the manufacturer (Western Lightning Kit; Perkin-Elmer). Primary antibodies used in the examples herein were obtained from Cell Signaling Technology: p-Stat3 (Tyr-705; 9145S), Stat3 (9132S), p-S6 kinase Thr-42I/Ser-424 (9204S), p-c-Kit (Tyr-719; 3391S), p-p38 MAPK (Thr-180/Tyr182; 9211S), p-AKT (Thr-308; 9275S), p-AKT (Ser-473) (9271S), AKT (9272S), p-S6 ribosomal protein (Ser-235/236; 2211S), p-GSK-3β (Ser-9; 9336S), p-EGFR (Tyr-845; 2231S), p-EGFR (Tyr-1068; 2234S), p-EGFR (Tyr-1173; 4407S), p-EGFR (Tyr1148; 4404S), p-EGFR (Tyr-1045; 2237S), p-EGFR (Tyr-992; 2235S), EGFR (2232S), MEK1/2 (9122S), p-MEK1/2 (Ser-217/221; 9121S), p-p42/44 MAPK (Erk1/2; Thr-202/Tyr-204; 9101S), p-PDK1 (Ser-241; 3061S), PDK1 (3062S), S6 ribosomal protein (2217S), antiphosphotyrosine 4G10 (Millipore, 05-1050), anti α-tubulin (DM1A; T9026-Sigma), and antidynamin (6C9; Sigma).

Example 5

Histology and Immunohistochemistry (IHC)

Deeply anesthetized tumor-bearing animals were transcardially perfused with cold PBS, brains were excised, rinsed in PBS, and serial coronal sections were cut using a brain mold. Half of the sections were used to isolate primary cultures of tumor cells as described herein and the other half were postfixed in 4% paraformaldehyde, embedded in paraffin, sectioned (5-10 mM) and stained with hematoxylin and eosin (H&E; Sigma). For IHC, sections were deparaffinized and rehydrated followed by antigen target retrieval and processing as described below. Antibodies were diluted in blocking solution and immunobinding of primary antibodies was detected by biotin-conjugated secondary antibodies and Vectastain ABC kit (Vector lab, Inc) using DAB (Vector lab, Inc) as a substrate for peroxidase activity and counterstained with haematoxylin as described in the manufacturer's protocol.

For immunohistochemistry (IHC), cut sections were deparaffinized and rehydrated through xylenes and graded alcohol series and rinsed for 5 min under tap water. Antigen target retrieval solution (Dako, S1699) was used to unmask the antigen (microwaved for 10 mM at low power then cooled for 30 min) followed by 3 washes with PBS for 5 min each. Quenching of endogenous peroxidase activity was performed by incubating the sections for 30 min in 0.3% $H_2O_2$ in methanol followed by PBS washes. Slides were preincubated in blocking solution [5% (vol/vol) goat serum (Sigma) in PBS 0.3% (vol/vol) Triton-X100] for 1 hr at room temperature, followed by mouse-on-mouse blocking reagent (Vector Labs, Inc.; MKB-2213) incubation for 1 hr. Primary antibody for the EGFR (mouse mAb anti-EGFR, 31G7, 1:100, Zymed, Lab, Inc.) was incubated for 24 hr. Secondary antibodies for IHC were biotinylated anti-rabbit or anti-mouse (Vector Labs, Inc.; 1:500). The following primary antibodies were used: anti-GFAP (Dako), anti-S100 (Dako), anti-EGFR (31G7; Zymed), and anti-NeuN (MAB377; Chemicon).

Example 6

Magnetic Resonance Imaging

MR imaging was performed on a 4.7 T Bruker Pharmascan MRI scanner. T2-weighted images (TR=3,500 ms, TE=75 ms, 12 signals acquired, acquisition time 11 min and 12 see, matrix size 256×256, field of view 2.5×2.5 cm, slice thickness 1.0 mm, 16 sections acquired) as well as pre- and postcontrast T1-weighted images (TR=800, TE=13; 4 signals acquired, acquisition time of 6 min 57 sec, matrix size 256×192, field of view 2.5×2.5 cm, slice thickness 1.0 mm, and 18 sections were acquired) were obtained after the i.v. administration of 0.3 mmol/kg of DTPA-Gd (Magnevist).

Example 7

Conditional Transgene Construction and Generation of Luciferase Reporter Strains The strategy for construction of the firefly luciferase genetically engineered reporter mouse strains is as follows: to construct the pCAGGS-LSL-Luciferase transgene, the CAGGS promoter, which is composed of a CMV immediate early enhancer, a chicken β-actin promoter and an SV40-derived intron (Miyazaki et al. 1989 Gene 79:269-277) was inserted adjacent to a firefly luciferase SV40 poly(A) tail cDNA. The activity of this promoter is abrogated by the presence of a potent foxed modified transcriptional/translational stop cassette (pBS302-PGK-Puro plasmid; Charest et al. 2006 Cancer Res 66:7473-7481) inserted between the CAGGS promoter and the luciferase cDNA. The resulting plasmid was linearized and electroporated in J1 129/S4 embryonic stem (ES) cells (Charest et al. 2006 Cancer Res 66:7473-7481). After selection with puromycin, resistant clones were screened for single integration events by Southern blot hybridization as follows: genomic DNA from individual ES clones was isolated according to Ausubel, F. 200 Current Protocols in Molecular Biology, Willey, New York, and was digested with 20 U of Bam HI and resolved by electrophoresis in 1% agarose gels containing TAE buffer (40 mM Tris-acetate, 20 mM sodium acetate, 20 mM EDTA, pH 7.6), and transferred onto nylon membranes (Hybond-N+; Amersham Biosciences) by capillary blotting in 20×SSC (1×SSC is 0.15 M NaCl, 0.015 M sodium citrate). Southern blots were prehybridized and hybridized at 42° C. in ULTRAhyb buffer (Ambion). The luciferase hybridization probe was labeled to high specific activity ($1\times10^9$ cpm/mg DNA) by random priming with a-$^{32}$P dATP (specific activity 3,000 Ci/mmole), and used at $1\times10^6$ cpm/ml of hybridization solution. The membranes were washed to a final stringency of 0.5×SSC, 0.1% SDS at 65° C. for 30 min, exposed to phosphoimaging plates and imaged. Individual clones with single integration events were selected for further use in examples herein.

Three ES cell clones, C6, F3 and E2 were selected for blastocyst injections and chimera production. Blastocysts were obtained 3.5 d after coitus from pregnant 6-wk-old BALB/c females obtained by natural mating with syngeneic males. ES cells (10-15) from each clone were microinjected into the blastocoel cavity. The blastocysts were then reimplanted into the uterine horn of pseudopregnant outbred mice. Chimeric offspring were identified by the agouti contribution of the ES cells to the coat color, and chimeric males were crossed with C57BL/6J females for germline transmission, which was determined by the presence of agouti offspring. ES clones C6 and F3 contributed to germ cell lineage and produced founder transgenic lines. Tail DNA samples from agouti offspring were genotyped for the presence of the luciferase transgene by PCR. Conditions for genotyping were 94° C. for 5 min followed by 35 cycles of 94° C. for 30 sec, 55° C. for 30 sec and 72° C. for 30 sec and ended with an extension of 10 min at 72° C. using primers LUC FA 5' CTGCATAAGGCTATGAAGAG 3' (SEQ ID NO: 7) and LUC RC 5' GAGGAGTTCATGATCAGTGC 3' (SEQ ID NO: 8).

Example 8

Mouse Crosses for Bioimaging and Induction of Gliomas

Female mice carrying the luciferase transgene Tg(CAG-luc)C6Char and Tg(CAG-luc)F3Char were crossed to males TgN(Lck-Cre)548Jxm (Rennet et al. 1995 Proc Natl Sci USA 92:12070-12074). Tail DNA from offspring were genotyped for Cre by PCR using cycling conditions described above and CRE 1F 5' CCGTACACCAAAATTTGCCTG 3' (SEQ ID NO: 9) and CRE 3R 5' CCCTGATCCTGGCAATTTCGG 3' (SEQ ID NO: 10) and for luciferase transgene as above.

Double transgenic animals were chosen for luciferase assays examples herein. For de novo malignant brain tumor imaging, Tg(CAG-luc)C6Char mice were crossed to Tg(CAG-FIGROS)Puro5Char; Cdkn2a$^{tm1Rdp/tm1Rdp}$ mice (Charest et al. 2006 Cancer Res 66:7473-7481; Serrano et al. 1996) and backcrossed to Cdkn2a$^{tm1Rdp/tm1Rdp}$ (Serrano et al. 1996) to obtain a p16$^{Ink4a}$ and p19$^{Arf}$ null background; and were further crossed to Tg(CAG-FIGROS)Puro5Char; Cdkn2a$^{tm1Rdp/tm1Rdp}$; Pten$^{tm1Hwu/tm1Hwu}$ mice and backcrossed to Cdkn2a$^{tm1Rdp/tm1Rdp}$; Pten$^{tm1Hwu/tm1Hwu}$ (Lesche et al. 2002 Genesis 32:148-149; Serrano et al. 1996 Cell 85:27-37) to obtain a p16$^{Ink4a}$ and p19$^{Arf}$ null; PTEN$^{lox/lox}$ background. A cohort of twelve Tg(CAG-FIGROS)Puro5Char;Cdkn2a$^{tm1Rdp/tm1Rdp}$;Pten$^{tm1Hwu/tm1Hwu}$ animals was used to establish penetrance and latency of GBM tumor formation and survival. Three cohorts of animals were established: experimental Tg(CAG-luc)C6Char;Tg(CAG-FIGROS)Puro5Char; Cdkn2a$^{tm1Rdp/tm1Rdp}$, Tg(CAG-luc)C6Char;Tg(CAG-FIGROS)Puro5Char; Cdkn2a$^{tm1Rdp/tm1Rdp}$; Pten$^{tm1Hwu/tm1Hwu}$ and control Tg(CAG-luc)C6Char;Cdkn2a$^{tm1Rdp/tm1Rdp}$; Pten$^{tm1Hwu/tm1Hwu}$.

For induction of gliomas, adult animals (older than 3 months) of the indicated genotypes were anesthetized with an IP injection of ketamine (100-125 mg/kg) and xylazine (10-12.5 mg/kg) and were mounted in a Stoelting stereotaxic frame (Harvard Apparatus Inc.) with non-puncturing ear bars. The incision site was shaved and sterilized (betadine surgical scrub). A 1 mm burr hole was drilled at the stereotactically defined location of the striatum (2.1 mm rostral to the bregma, 1.5 mm lateral to the midline and at 2 mm depth to the pia surface) and a 1 μL syringe (Hamilton) was used to inject $1\times10^8$ Adeno CMV-Cre viral particles (Gene Transfer Vector Core, University of Iowa, Iowa City, Iowa) at a rate of 0.1 μL per minute. Post injection, the burr hole was sealed with sterile bone wax and the skin sutured.

Example 9

Luciferase Assays

Each of 12 single-transgene integration ES cell clones were transfected transiently by electroporation in triplicate with a Cre expression plasmid (pCAG-Cre) and control empty vector plasmid using conditions described elsewhere (Charest et al. 2006 Cancer Res 66:7473-7481). Electroporated ES cells were lysed 48 hours later and luciferase assays were performed using Promega's Luciferase Assay System according to the manufacturer's instructions. In vivo assessment of recombination potential was performed as follows: the Tg(CAG-luc)C6Char and Tg(CAG-luc)F3Char reporter lines were each crossed to a line that expresses Cre in thymocytes (TgN(Lck-Cre)548Jxm; Hennet, R. et al. Proc Natl Acad Sci USA 92:12070-12074). Results from these crosses generated the expected Mendelian ratio of double and single hemizygous animals showing that transmission of the luciferase reporter transgenes does not affect viability.

Thymocytes from TgN(Lck-Cre)548Jxm;Tg(CAG-luc)C6Char, TgN(Lck-Cre)548Jxm;Tg(CAG-luc)F3Char and Tg(CAG-luc)C6Char and Tg(CAG-luc)F3Char control mice were harvested as follows: three mice of each genotype were dissected and individual thymi were removed and placed in 60 mm petri dishes filled with DMEM (Invitrogen) and pulled apart using sterile forceps. Released thymocytes were transferred to 15 mL conical centrifuge tubes, spun at room temperature for 10 min. at 1-1.5×1000 rpm and washed 2-3× in DMEM. Thymocytes ($1\times10^5$) were lysed and luciferase assays were performed as indicated above.

Data showed that both Tg(CAG-luc)C6Char and Tg(CAG-luc)F3Char reporter strains displayed strong thymocytes luciferase activity in the presence of Cre recombinase and virtually no activity in the absence of Cre, showing that the transcriptional and translational stop cassette were recombined in vivo and that both transgenic strains display minimal background and potent luciferase activity when activated by a tissue-specific Cre recombinase.

Example 10

Induction of Lung Tumors

Approximately $10^7$ particles of Ad-CMV-Cre were instillated directly into the lungs of compound Tg(CAG-luc) C6Char; Kras$^{tm4Tyj/+}$ mice via intranasal inhalation according to Jackson et al. 2001 Genes Dev 15:3243-3248.

Example 11

Bioimaging

Bioluminescence was measured noninvasively using the IVIS 200 imaging system (Xenogen). For live imaging, the surface areas of focus for imaging were depilated using commercial depilatory creams. Images were taken 10 min after IP injection of luciferin (225 mg/kg, Xenogen) to allow sufficient time for distribution of luciferin, with a 60 second photon acquisition during which mice were sedated via continuous inhalation of 3% isoflurane. For organ imaging post luciferin injection, animals were incubated for 10 min and perfused transcardially with saline. Bioluminescence imaging was then performed on individually dissected organs. Signal intensity was quantified for defined regions of interest as photon count rate per unit body area per unit solid angle subtended by the detector (units of photons/s/cm$^2$/steradian). All image analyses and bioluminescent quantification were performed using Living Image software v. 2.50 (Xenogen).

Example 12

EGFR Mouse Model

In human GBMs, overexpression of EGFR resulting from either increased transcriptional activity or gene amplification events, results in overexpression of the receptor. In 50% of the gene amplification cases, a concomitant rearrangement of the gene occurs, deleting exons 2-7. This in frame, intragenic deletion produces a ligand-independent, constitutively activated receptor (EGFRvIII) which is highly oncogenic.

GBMs have been observed to express EGFRWT alone, coexpress EGFRWT and EGFRvIII or express EGFRvIII solely (Sarkaria, J. N. et al. 2007 Mal Cancer Ther 6:1167-1174; Sarkaria, J. N. et al. 2006 Clin Cancer Res 12:2264-2271; Challa, P. et al. 2005 Mol Vis 11:425-430; Giannini, C. et al. 2005 Neuro Oncol 7:164-176). In the latter case, loss of EGFR WT expression is most likely the result of a clonal expansion of cells that have undergone loss of heterozygosity at the EGFR gene locus, duplicating the EGFRvIII carrying chromosomal region.

Figure 2A:
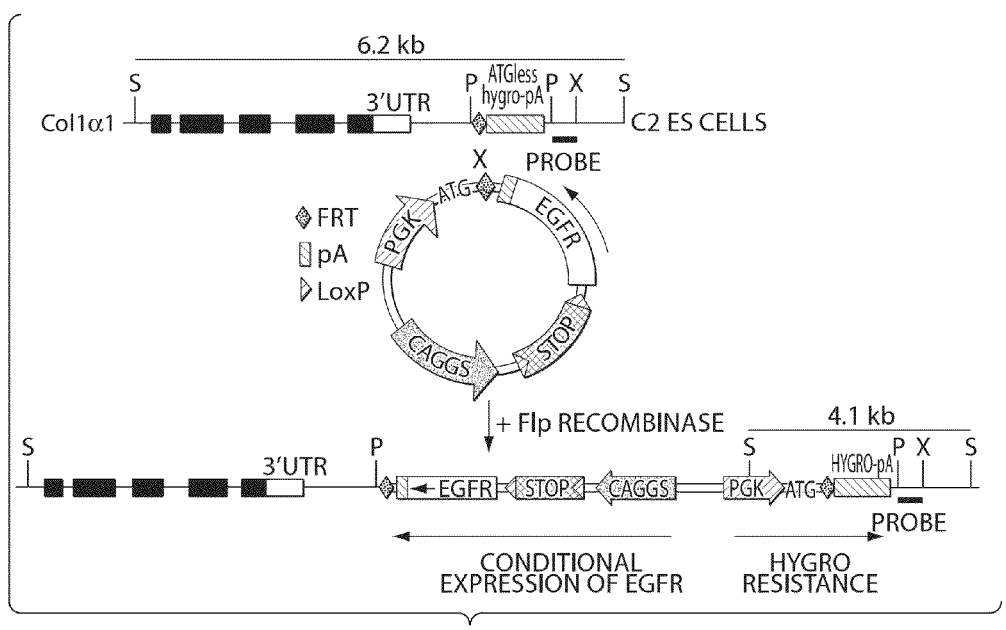
FIG. 2 is a drawing and a photograph showing the "knock in" strategy to produce conditional EGFR transgenic mice.
Figure 2B:
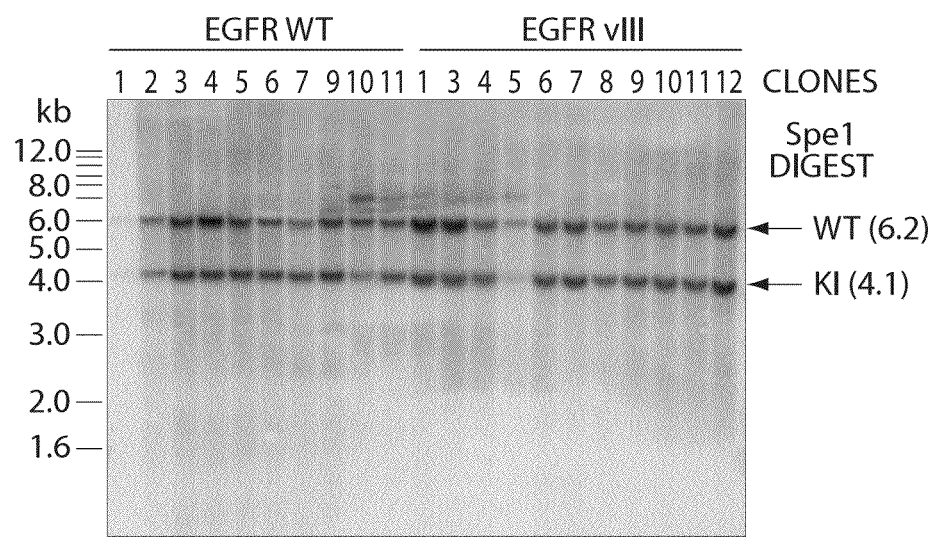

To model overexpression of wild type and vIII EGFR, two Cre-Lox based conditional transgenic mice capable of robust expression of human EGFR$^{WT}$ and EGFR$^{vIII}$ cDNAs were generated in examples herein. These strains were engineered using a modification of a Flp recombinase-based knockin methodology (Beard, C. et al. 2006 Genesis 44:23-28). The EGFR transgenes were targeted (knocked-in) to the Colagen1α1 gene locus (FIG. 2). The conditional EGFR transgene were constructed as follows: a loxP site flanked transcriptional/translational stop cassette was inserted between a ubiquitous promoter (the pCAGGS promoter, composed of a CMV immediate early enhancer and a chicken β-actin promoter) and the human EGFR wild type or vIII cDNAs flanked at the 3' and 5' ends with Col1α1 genomic sequences (FIG. 2). Col1α1-EGFR plasmid DNA was electroporated into engineered embryonic stem cells (C2 cells) along with a plasmid coding for the Flp recombinase, drug selected and screened for successful knock in events by Southern blot analysis of ES cells genomic DNA. Selected ES cell clones were injected into blastocysts and ensuing germ line-transmitted transgenic founders were generated. To generate EGFRWT and EGFRvIII expressing mice, the two transgenic knockin strains were crossed together. Molecular characterization of human GBMs reveals that overexpression of EGFR is almost always accompanied with the loss of the tumor suppressor gene locus p16Ink4a/p19ARF and PTEN (McLendon, R. 2008 Nature 455:1061-1068). Therefore, conditional EGFR transgenic lines were crossed to a strain of mice that carried a germ line dually disrupted p16Ink4a and p19Arf genes (referred herein after as InkΔ2/3; Serrano, M. et al. 1995 Cell 85:27-37). A resulting animal was further crossed to a strain carrying a floxed conditional allele of PTEN (Groszer, M. et al. 2001 Science 294:2186-2189) thus engineering a triple transgenic mice.

Figure 3A:
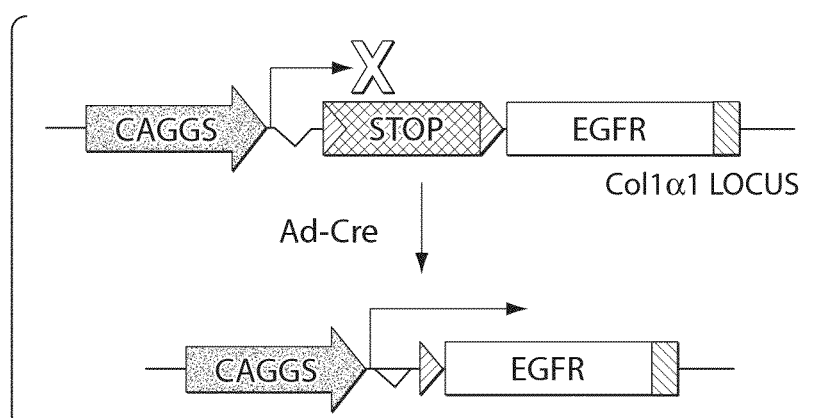
FIG. 3 is a drawing and a graph (Kaplan-Meier) showing that localized somatic expression of EGFR in adult mouse brains resulted in formation of tumors.
Figure 3B:
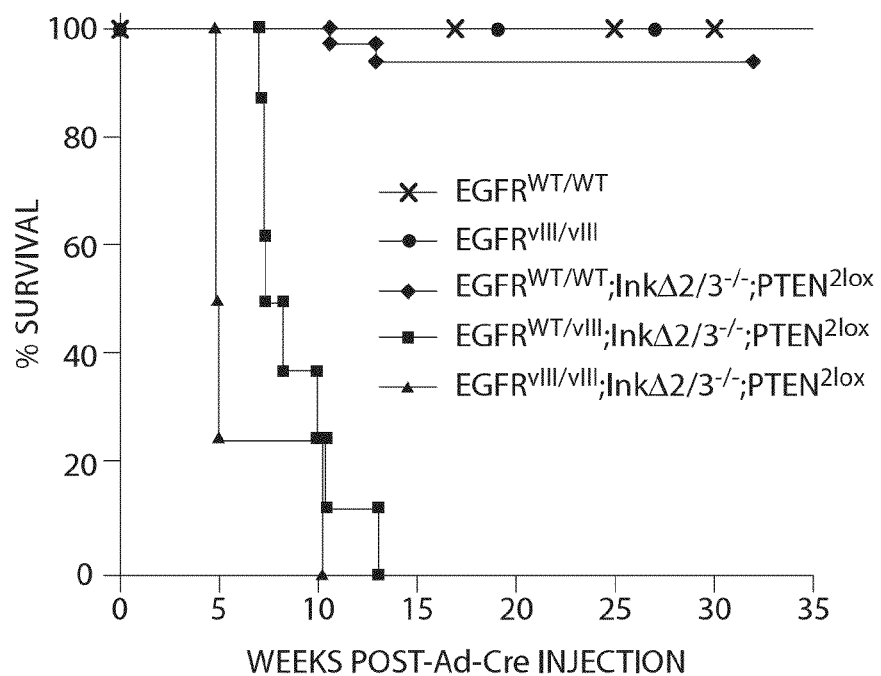
Figure 4A:
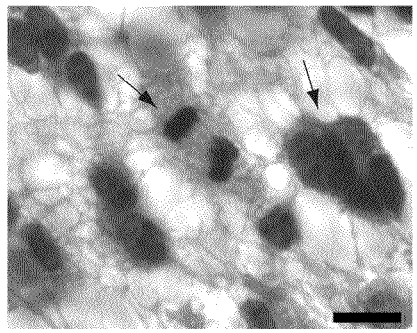
FIG. 4 a set of photomicrographs showing neuropathological analysis of EGFR tumors. Representative photomicrographs were taken of cells of each of Col1α1-EGFR; InkΔ2/3$^{-/-}$; PTEN$^{-/-}$ tumor sections stained with H&E. Expression of both WT and vIII EGFR resulted in similar tumor phenotypes.
Figure 4B:
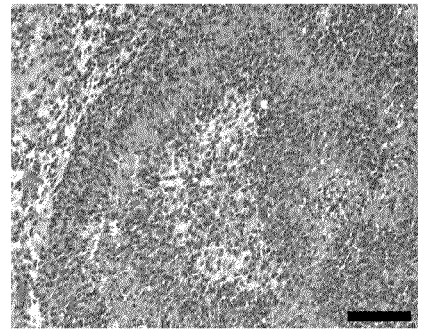
Figure 4C:
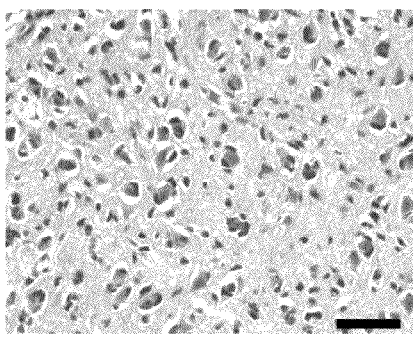
Figure 4D:
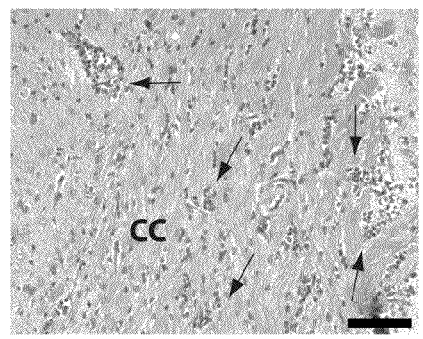
Figure 4E:
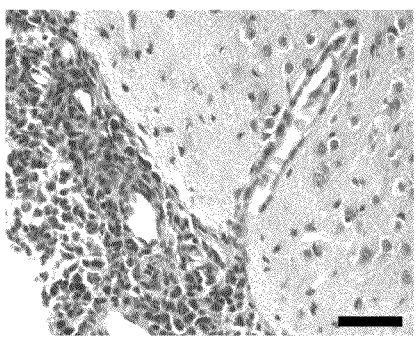
Figure 4F:
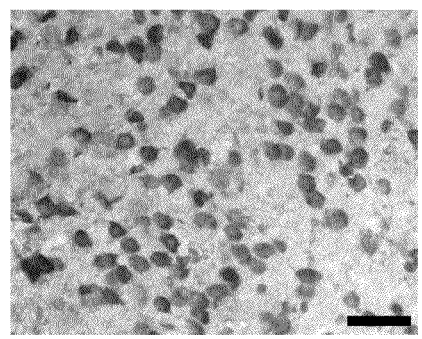

In these conditional EGFR transgenic animals, expression of the receptor is dependent on a Cre recombinase-mediated deletion of the foxed transcriptional/translational stop cassette (FIG. 3). To obtain spatio-temporal control of transgene expression and to model adult onset of GBM, stereotactic intracranial injections of adenovirus transducing Cre recombinase (Ad-CMVCre) were performed in transgenic animals. Because most, if not all, CNS specific Cre transgenic lines are leaky (i.e. express Cre recombinase ectopically at one point or another during development or are not cell lineage restricted), Cre was delivered through this more direct methodology. Examples herein demonstrated successful GBM initiation in a similar (FIG-ROS) genetically engineered model of GBM (Charest, A. et al. 2006 Cancer Res 66:7473-7481). Adenoviruses remain episomal following infection of host cells, resulting in a transient expression of Cre recombinase with no potential for insertional mutagenesis.

Example 13

Expression of EGFR in Adult Brain Tissues is not a Transforming Event

To evaluate the capacity of EGFR to induce adult onset primary brain cancer de novo, Cre-Lox conditional transgenic strains of mice capable of expressing WT and/or vIII human EGF receptors were created. This was achieved by targeting the insertion of EGFR mini genes into the mouse collagen 1α1 gene locus. The basis of these mini genes consist of a floxed transcriptional/translational stop cassette inserted between a strong ubiquitous promoter (CAGGS) and the EGFR cDNAs (either WT or vIII; FIG. 2 panel A). Two EGFR strains were produced, one expressing the wild type receptor (referred as EGFR$^{WT}$) and another expressing the oncogenic variant vIII (EGFR$^{vIII}$). To obtain a strict spatio-temporal control over EGFR expression, the removal of the foxed stop cassette was somatically induced by stereotactic intracranial injections of an adenovirus transducing Cre recombinase (Ad-Cre). Recombinant adenoviruses are episomal following infection of host cells and capable of efficient expression, resulting in a transient expression of Cre with no potential for insertional mutagenesis. Ad-Cre was injected in the basal ganglia (striatum) of homozygous Col1α1-EGFR$^{WT/WT}$ and Col1α1-EGFR$^{vIII/vIII}$ mice and monitored tumor formation and survival over time. After 35 weeks post injection, none of the injected animals developed tumors as measured by survival and histological means (FIG. 3 panel B). These data shows that expression of EGFR in adult brain tissue did not initiate tumors during a period of observation corresponding to a significant portion of a rodent life span (1.5-2 years).

Example 14

Loss of p16Ink4a, p19Arf and Pten Cooperates with EGFR in Gliomagenesis

Intracranial Ad-CMVCre stereotactic injections were performed on established cohorts of mice with EGFR transgene combinations that recapitulate the human disease, and injected animals were monitored for tumor formation and survival (FIG. 3). Kaplan-Meier survival curves demonstrate that the EGFR$^{vIII}$ allele is a potent oncogene capable of forming aggressive tumors within a few weeks post activation when present on an InkΔ2/3 null and PTEN null background. Surprisingly, overexpression of the EGFR$^{WT}$ allele was observed to be relatively inefficient at forming intracranial tumors even though robust expression of the receptor from the Col1α1 locus is observed. It was hypothesized that the effect was due to the absence of expression of a ligand, which is necessary to activate the receptor. Nevertheless, a few GBM tumors forming in this strain were observed. Genomic analysis of these tumor cells by array comparative genomic hybridization (aCGH) revealed amplification events at the loci encompassing the genes for the EGFR ligands epiregulin, betacellulin and HB-EGF (Table 1). For the EGFRWT tumors produced in model herein, tumor cells that express EGFR ligands (through gene amplification for example) were selected and that EGFR ligands drive tumor formation. Homozygous null mice for the Ink4a/Arf locus develop lymphomas and subcutis sarcomas at a median age of 30 weeks and have never been reported to develop glioma in their lifespan (Serrano, M. et al. 1995 Cell 85:27-37). Non-recombined PTENlox/lox mice are normal and viable and CNS-specific deletion of PTEN alone does not form GBM tumors (Xiao, A. et al. 2005 Cancer Res 65:5172-5180).

An extensive molecular characterization of human GBMs revealed a number of genetic aberrations in which RTKs were activated concomitantly with the loss of tumor suppressor gene function such as those encoded by the Ink4a/Arf and PTEN loci (Consortium TCGA 2008 NAture 455:1061-1068). Conditional EGFR transgenic lines were crossed to strains of mice that carried dually disrupted p16Ink4a and p19Arf genes (referred to thereafter as InkΔ2/3; Serrano, M. et al. 1996 Cell 85:27-37) and a conditional knock out PTEN gene (Lesche, R. et al. 2002 Genesis 32:148-149).

Cohorts of Col1α1-EGFR$^{WT/WT}$, Col1α1-EGFR$^{WT/vIII}$ and Col1α1-EGFR$^{vIII/vIII}$ animals all on an InkΔ2/3 null and conditional PTEN$^{2lox}$ knock out background animals were subjected to stereotactic Ad-Cre injections and monitored for tumor formation and survival (FIG. 3 panel B). When combined with InkΔ2/3 and PTEN deficiency, expression of EGFR resulted in the formation of highly aggressive tumors. Surprisingly, expression of EGFR$^{WT}$ was rather inefficient at creating tumors whereas the addition of a single copy of the EGFR$^{vIII}$ variant allele significantly increased the penetrance and reduced the latency of tumor formation leading to death in 100% of the animals within 13 weeks after Ad-Cre injection (FIG. 3 panel B). Homozygous EGFR$^{vIII/vIII}$-expressing animals exhibited a slightly more aggressive tumor formation phenotype with a shorter latency as compared to EGFR$^{WT/vIII}$-expressing mice (FIG. 3 panel B). The different potency in tumor formation between EGFR WT and vIII is not due to initial weaker expression of EGFRWT versus vIII receptors, thus demonstrating that injection of Ad-Cre in the striatum of our EGFR$^{WT}$ conditional transgenic line result in expression of the receptor and that this expression, in most cases, seems insufficient to form cancerous lesions. Expression of EGF receptors in vivo post Ad-Cre injection was shown herein. Col1α1-EGFR$^{WT/WT}$ and Col1α1-EGFR$^{vIII/vIII}$ mice on InkΔ2/3 and PTEN null backgrounds were injected with Ad-Cre virus and EGFR expression detected by immunohistochemistry (DAB stain) 5, 11, 16 and 21 days after injections. Sections were counterstained with hematoxylin. Cells expressing EGFR were identified. By day 21 post Ad-Cre administration, EGFR$^{WT/WT}$-expressing cells were observed to be rare or non-existent whereas EGFR$^{vIII/vIII}$ cells were observed in huge numbers.

Example 15

Col1α1-EGFR; InkΔ2/3$^{-/-}$; PTEN$^{-/-}$ Tumors are Highly Infiltrative GBMs

The histopathologic features of EGFR tumors share a high degree of similarity with human GBMs. All Col1α1-EGFR; InkΔ2/3$^{-/-}$; PTEN$^{-/-}$ tumors are highly cellular and are composed of cells containing pleomorphic nuclei (FIG. 4 panel A-white arrow) set in a fibrillary background. Tumor cells typically have a gemistocytic appearance with eccentrically placed nucleus and abundant cytoplasm. The tumors also contain a high number of proliferating cells as detected by the presence of mitoses (FIG. 4 panel A-black arrows). In addition, these tumors include large areas of necrosis and demonstrate profound perineuronal satellitosis, two salient features of GBMs (FIG. 4 panels B and C).

The high degree of lethality associated with GBMs stem from their ability for recurrence following debulking surgical interventions (Demuth, T. et al. 2004 J Neurooncol 70:217-228). A hallmark of human GBMs is the heighten infiltration capacities of tumor cells. GBM cells typically invade the surrounding parenchyma and appear to follow distinct anatomical structures within the central nervous system often egressing along white matter tracts, the basement membranes of blood vessels or beneath the subdural sheets. In our models, we consistently observe tumor cells that have migrated away from the main tumor mass. In all tumors, a population of astrocytoma cells infiltrated the brain by migrating along the white matter tracts and the sub-arachnoid and perivascular Virchow-Robin spaces, features almost always associated with GBMs. The extracellular milieu of anatomical structures such as blood vessel basement membranes or between myelinated axons is profoundly different. This suggests a pleotropic fashion by which glioma cells are able to use a variety of matrix ligands, possibly activating distinct mechanisms for invasion. Taken together, these results demonstrate that expression of EGFR wild type along with its vIII variant in CNS glia cooperates with loss of the tumor suppressor locus Ink4a; Arf and PTEN gene products to form GBM brain tumors.

One of the hallmarks of human GBMs is the heightened infiltration capacity of the tumor cells. GBM cells typically invade the surrounding parenchyma and appear to follow distinct anatomical structures within the CNS, often egressing along white matter tracts, the basement membranes of blood vessels or beneath the subdural sheets. In all tumors observed, a population of GBM cells infiltrated the brain by migrating along the white matter tracts (FIG. 4 panel D) and the sub-arachnoid (FIG. 4 panel E) and perivascular Virchow-Robin spaces (FIG. 4 panel D). Using immunohistochemistry (IHC) staining for EGFR, we were able to observe single EGFR-expressing tumor cells situated away from the bulk tumor masses (FIG. 4 panel F). The extent of this migration is widespread and can reach far distant regions of the brain since EGFR tumors are highly infiltrative Tumors resulting from Ad-Cre-triggered expression of EGFR$^{vIII}$ in the striatum of mice with p16Ink4a;p19Arf and PTEN deletion typically appear as masses with variable amounts of hemorrhage and compression of adjacent brain structures as shown by histopathology of EGFR GBM tumors. Sections of representative EGFR$^{vIII/+}$; InkΔ2/3$^{-/-}$; PTEN$^{-/-}$ GBM tumors were H&E stained. Data show that tumors contained area of varying degree of hemorrhaging and that a GBM tumor exerted pressure on the lateral ventricle.

Figure 5:
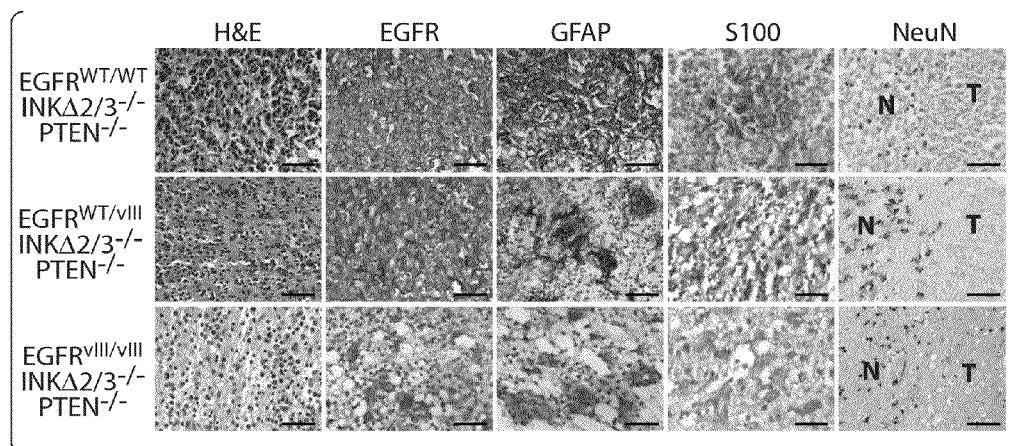
FIG. 5 is a set of photomicrographs showing EGFR GBM tumors that had expressed markers of astrocytic differentiation in each of three different sets of mice. Representative photomicrographs of GBM tumors of the indicated genotypes were stained with each of H&E expression of EGFR, the astrocytic markers glial fibrillary acidic protein (GFAP), S100 and neuronal marker NeuN by IHC. N, normal brain; T, tumor. Scale bars 62.5 μM.
Figure 6A:
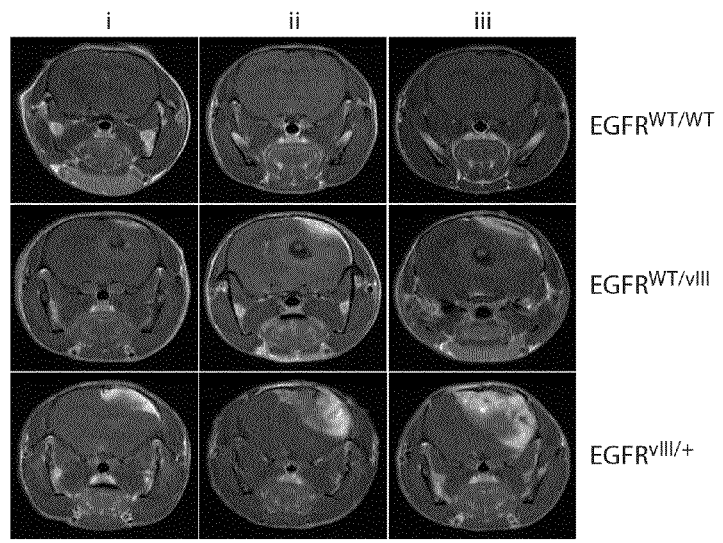
FIG. 6 is a set of magnetic resonance (MR) images, a line graph and a set of photomicrographs showing growth rate of GBM tumors.
Figure 6B:
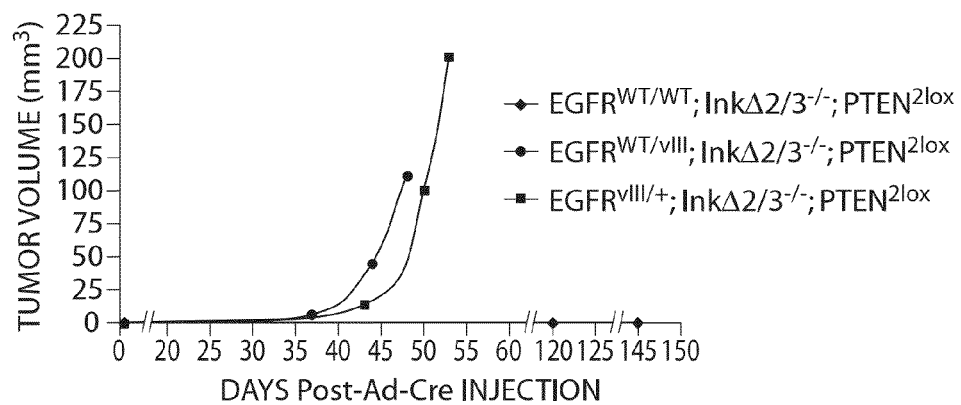
Figure 6C:
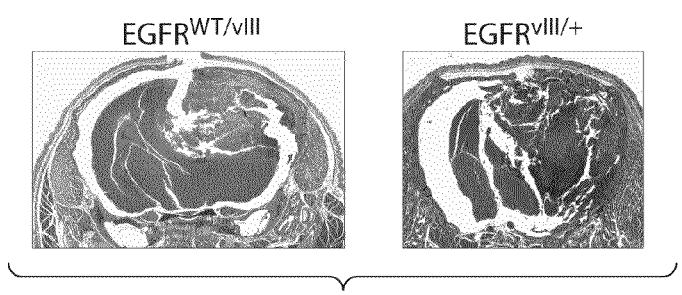

At 2 weeks post Ad-Cre injection, EGFR$^{vIII}$-expressing tumors often consisted of a few clusters of neoplastic cells. Characteristics of mutant EGFR GBM tumor growth over time were investigated herein. GBM tumor sections were H&E-stained and examined at 2, 4, 6 and 8 weeks post injection of Ad-Cre into the CNS of EGFR$^{WT/vIII}$; InkΔ2/3$^{-/-}$; PTEN$^{-/-}$ and EGFR$^{vIII/+}$; InkΔ2/3$^{-/-}$; PTEN$^{-/-}$ mice. Over a period of an additional two weeks, the tumor masses increased in size and often demonstrate perivascular infiltration. At six and eight weeks post administration of Ad-Cre, tumor cells typically infiltrate the meninges, at which point tumor growth increases dramatically. This explosive growth is highly reminiscent of that observed in human GBMs where tumors often remain clinically undetected until they enter a massively expansive growth rate at which point detection typically results from neurological deficits (Kleihues, P. et al. 2000 IARC Press, Lyon, France). Using magnetic resonance imaging (MRI), the growth rates of EGFR$^{vIII}$-expressing GBMs was measured, and data show that the tumors expand swiftly and sharply (FIG. 6), ultimately reaching sizes that are incompatible with basic brain functions. EGFR$^{vIII}$-expressing GBM tumors typically had irregular, thick, nodular, peripherally enhancing masses with areas of central necrosis (FIG. 6) with meningeal infiltrates appearing as hyperintense signals on T1-weighted contrast-enhanced images. IHC staining of these tumors for EGFR demonstrates robust membrane expression and staining for markers associated with astrocytic (GFAP and S100) and neuronal (NeuN) differentiation revealed that the neoplastic cells only express markers of astrocytic lineage (FIG. 5). Taken together, these results demonstrate that expression of mutant EGFR, and to a lesser extent WT EGFR, in CNS glia cooperates with loss of the tumor suppressor loci Ink4a;Arf and PTEN gene products to form GBM tumors.

Example 16

Signaling Pathways Initiated by EGFR in GBM Tumor Cells

Figure 7A:
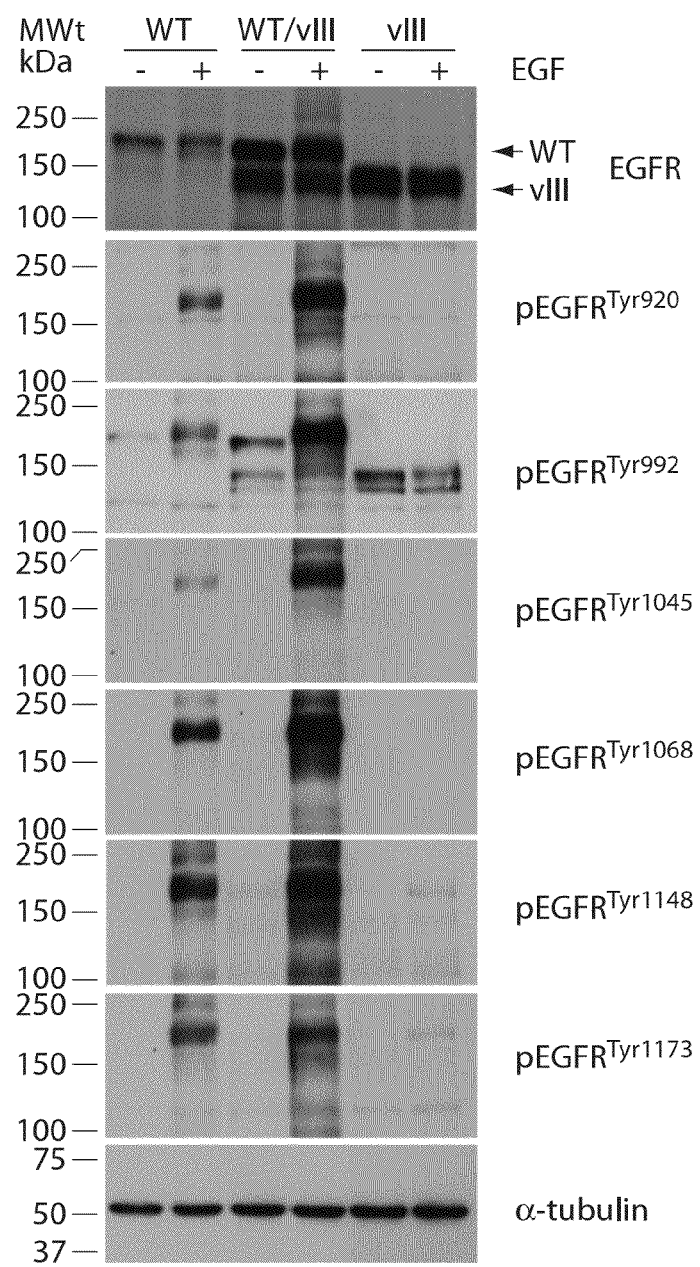
FIG. 7 a drawing and a photograph showing EGFR autophosphorylation site preferences in GBM tumor cells.
Figure 7B:
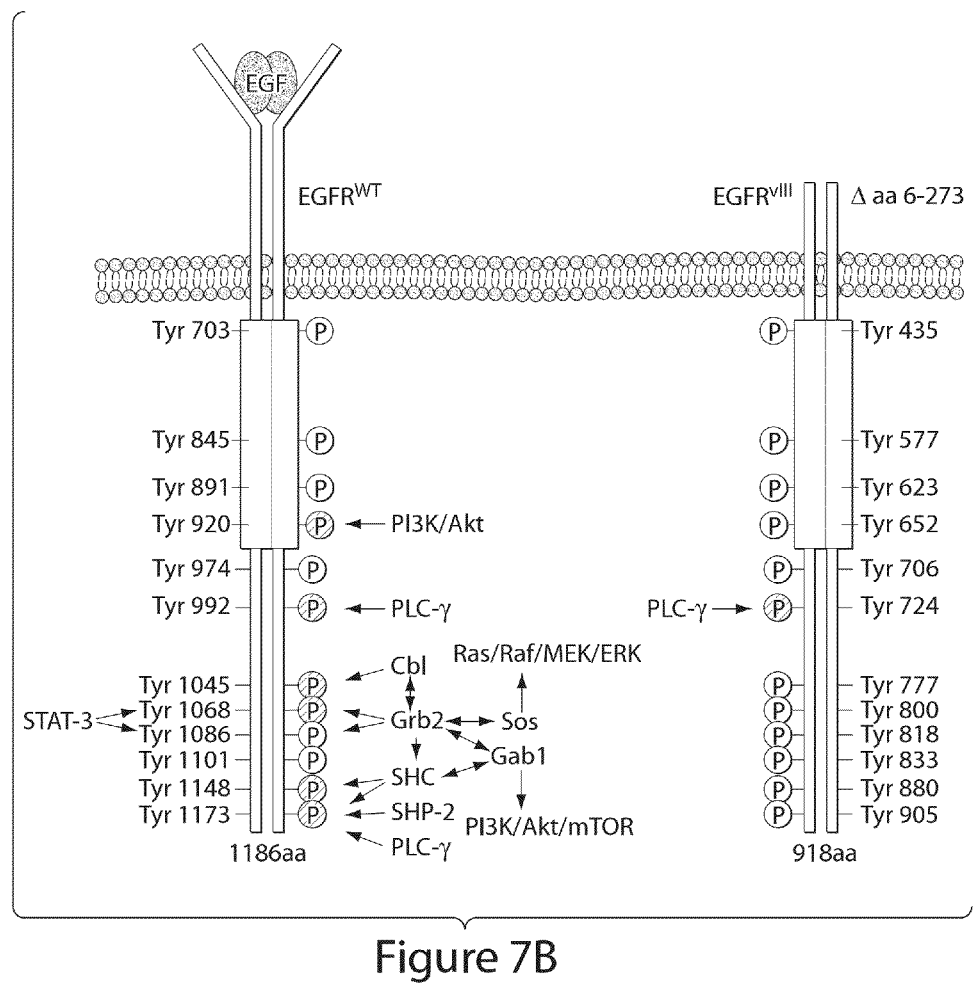

RTKs relay signals through the phosphorylation of substrate molecules and via the interaction of signaling molecules with autophosphorylation sites (Pawson, T. 2007 Curr Opin Cell Biol 19:112-116). The extent of phosphorylation events on the receptor itself was characterized by immunoblot analysis of cultured cells from different tumors using anti phospho site-specific EGFR antibodies (FIG. 7). These data indicated that in GBM tumor cells, many signaling pathways are emanating from EGFR as observed by the specific pTyr sites that are phosphorylated. Surprisingly, the EGFR$^{vIII}$ receptor is virtually devoided of phosphorylation when compared to EGF stimulated EGFR$^{WT}$, except for pTyr992 site (FIG. 7), which appear to be constitutively phosphorylated. A priori, this would suggest that EGFR$^{vIII}$ would preferentially signal through the activation of PLCγ. Another remarkable feature of these cells is the heighten levels of specific site phosphorylation in cells expressing both EGFR$^{WT}$ and EGFR$^{vIII}$ when compared to cells expressing EGFR$^{WT}$ only. It is conceivable that the presence of a vIII allele prolongs the resident time of individual phosphorylation events on a per receptor basis or allows for more WT receptors to be activated by EGF ligand.

Figure 10:
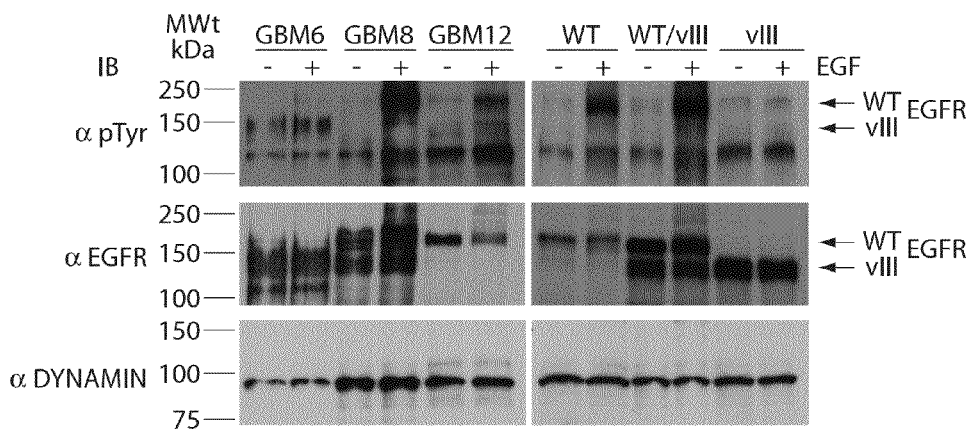
FIG. 10 is a set of photographs showing immunoblot analyses of levels of expression of the EGF receptors in cells derived from each of: representative EGFR$^{WT/WT}$; InkΔ2/3$^{-/-}$; PTEN$^{-/-}$, EGFR$^{WT/vIII}$; InkΔ2/3$^{-/-}$; PTEN$^{-/-}$, and EGFR$^{vIII/+}$; InkΔ2/3$^{-/-}$; PTEN$^{-/-}$ GBM tumors and those of human GBM ex vivo cultures (Sakaria, J. N. et al. 2006 Clin Cancer Res 65:5172-5180). Human GBM6 expresses EGF$^{vIII}$ only, GBM8 expresses EGFR$^{WT}$ and EGFR$^{vIII}$ and GBM12 expresses EGFR$^{WT}$ only. Cells were starved in 0.1% FBS media for 24 hours and treated for 5 minutes with 50 ng/mL EGF. Cell lysates were immunoblotted using anti phosphotyrosine (α pTyr), membranes were stripped and reprobed for total EGFR protein (αEGFR) and for dynamin (loading control).

To better understand the mechanisms by which EGFR exerts its oncogenic potential, tumors of the genotypes EGFR$^{WT/WT}$, EGFR$^{WT/vIII}$, and EGFR$^{vIII/+}$, all on an InkΔ2/3$^{-/-}$ and PTEN$^{-/-}$ background, were cultured ex vivo. The suitability of these cells to study signal transduction events was confirmed by comparing the levels of EGFR expression in representative samples of each genotype to human primary cultures of GBMs (Sarkaria, J. N. et al. 2006 Clin Cancer Res 12:2264-2271) by immunoblot analysis (FIG. 10). Immunoblot analysis of the levels of expression of the EGF receptors in cells derived from representative EGFR$^{WT/WT}$; InkΔ2/3$^{-/-}$; PTEN$^{-/-}$ and EGFR$^{WT/vIII}$; InkΔ2/3$^{-/-}$; PTEN$^{-/-}$ and EGFR$^{vIII/+}$; InkΔ2/3$^{-/-}$; PTEN$^{-/-}$ GBM tumors and those of human GBM ex vivo cultures was performed (Sarkaria, J. N. et al. 2006 Clin Cancer Res 12:2264-2271). Human GBM6 expresses EGFR$^{vIII}$ only, GBM8 expresses EGFR wild type and EGFR$^{vIII}$ and GBM12 expresses EGFR wild type only. Cells were starved in 0.1% FBS media for 24 hours and treated for 5 minutes with 50 ng/mL of EGF. Cell lysates were immunoblotted against anti phosphotyrosine (αpTyr), membranes were stripped and reprobed for total EGFR protein (αEGFR) and dynamin as loading control.

Figure 8:
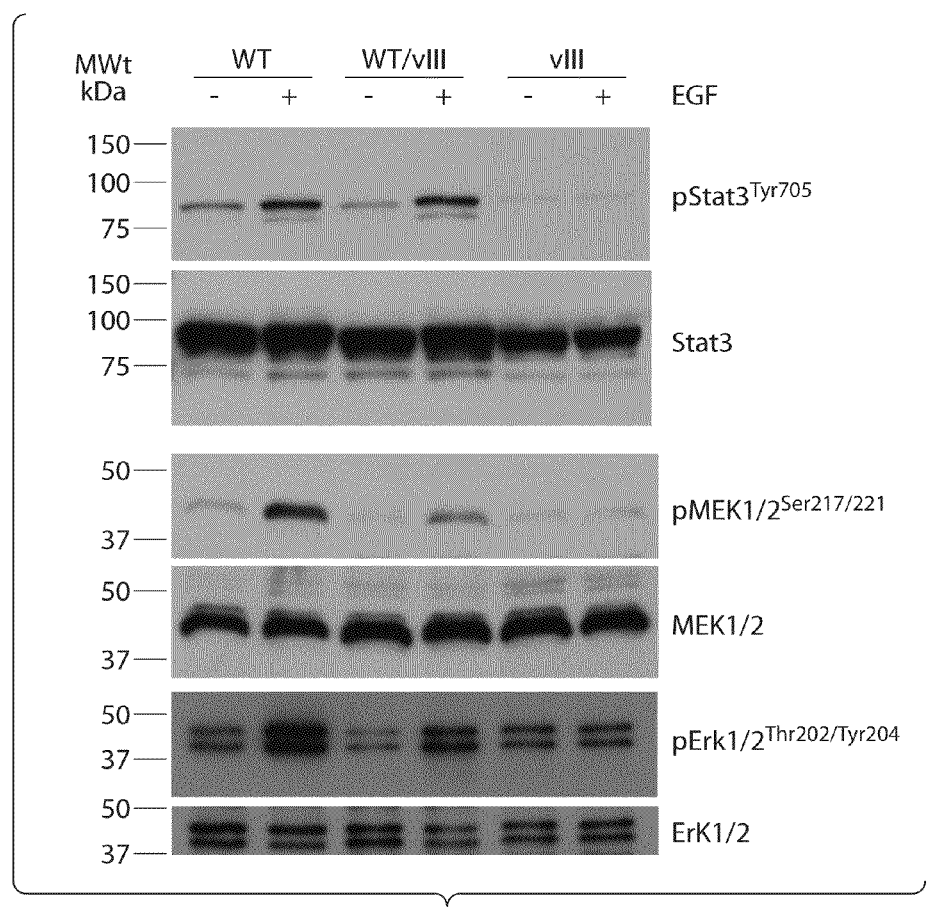
FIG. 8 is a set of photographs of immunoblots with each of several phospho specific antibodies showing activation of Stat3 and MEK/ERK by EGFR$^{WT}$ and not by EGFR$^{vIII}$. Ex vivo cultures of cells from each of the indicated tumor genotypes were starved for 24 hours and were stimulated with 50 ng/mL of EGF for 5 minutes. Immunoblots of total cell lysates were probed with the indicated antibodies.
Figure 9:
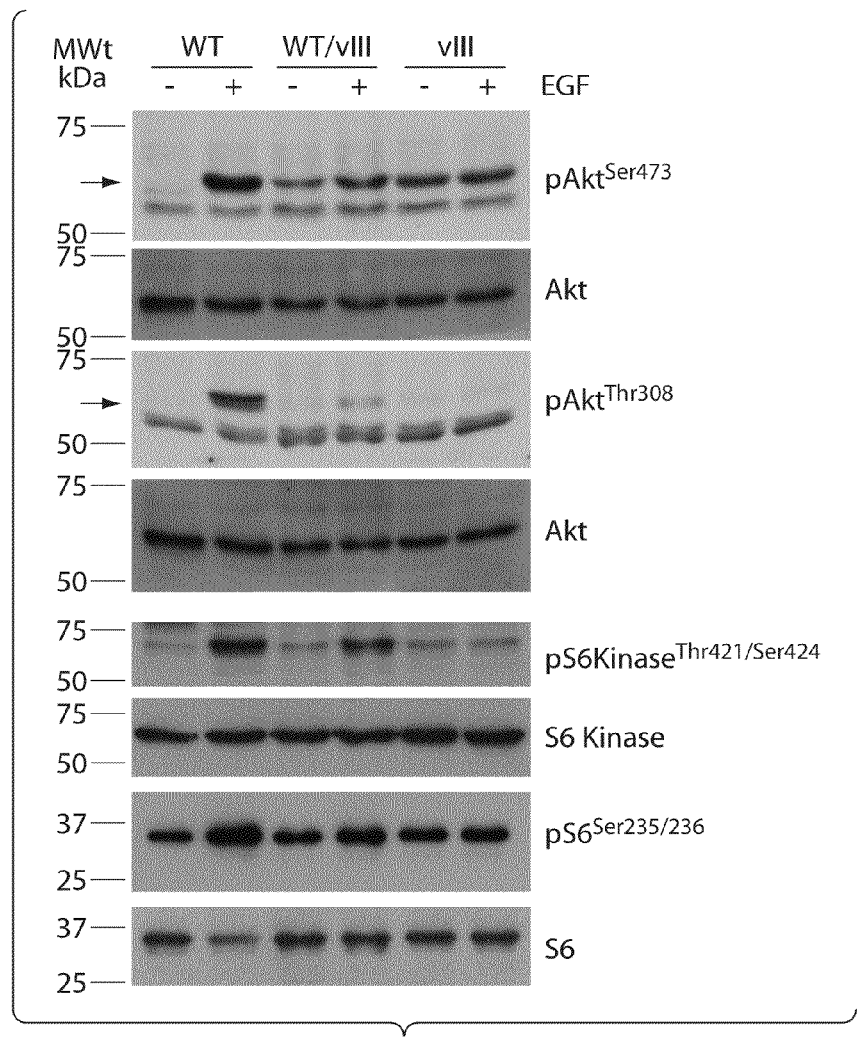
FIG. 9 is a set photograph of immunoblots with each of several phospho specific antibodies showing constitutive activation of mTORC2 in EGFR$^{vIII}$, and that EGFR$^{vIII}$ signals differently than EGFR$^{WT}$. Western blot analysis of total cell extracts from GBM tumor cells shows that the cells expressed the indicated receptors. Cells were serum starved and stimulated as above. Immunoblots were probed with antibodies as indicated. EGF ligand stimulation of EGFR$^{WT}$-expressing cells stimulated activation of mTORC1 whereas mTORC2 was constitutively activated in EGFR$^{vIII}$-expressing GBM tumor cells.
Figure 11:
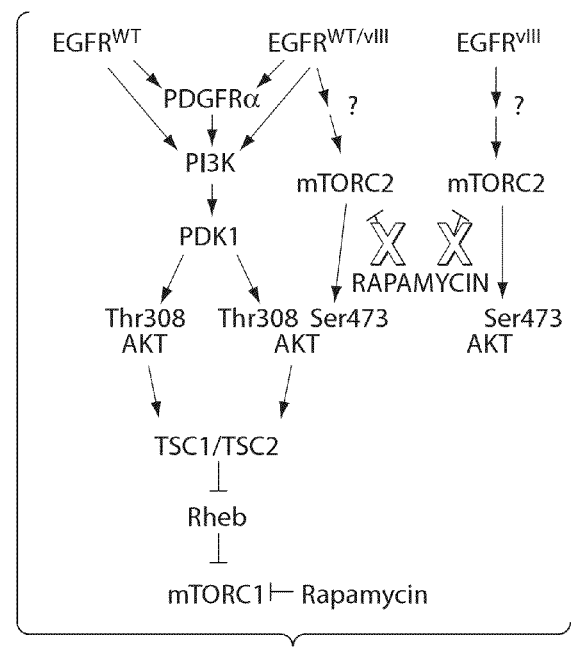
FIG. 11 is a drawing showing a switch in mTORC in EGFR$^{vIII}$ expressing GBM tumor cells. Expression of EGFR$^{vIII}$ led to activation of mTORC2 as observed by persistent pSer473 AKT event. EGFR$^{WT}$ expressing cells activated AKT through the canonical PI3K/PDK1 pathway.

Using primary cultures of GBM cells, EGFR autophosphorylation sites were identified using phospho-specific anti-EGFR antibodies in immunoblot assays (FIG. 7 panel A). Phosphorylation on tyrosine residues 920, 992, 1045, 1068, 1148 and 1173 upon EGF stimulation of cells expressing EGFR$^{WT}$ was detected. Surprisingly, the only autophosphorylation detected in EGFR$^{vIII}$-expressing cells was the constitutive phosphorylation of tyrosine residue 992 (FIG. 7 panel A). Phosphorylation on these 6 tyrosine residues has been shown to be linked to activation of the phosphatidylinositol 3-kinase (PI3K)/Akt, ras/raf/MEK/ERK, phospholipase C gamma (PLCg), and signal transducer and activator of transcription (STAT3) signaling pathways (for a review of EGFR signaling see Sebastian, S. et al. 2006 Biochim Biophys Acta 1766:120-139). Activation of these signaling pathways was confirmed in ex vivo cultures herein by immunoblot analysis with phospho-specific antibodies against these proteins. Phosphorylation of STAT3 at tyrosine 705 is induced by stimulation of GBM tumor cells with EGF ligand in EGFR$^{WT}$-expressing cells but not in constitutively activated EGFR$^{vIII}$-expressing cells (FIG. 8). A similar pattern is observed for the formation of phospho-MEK1/2 (Ser217/221) and phospho-Erk1/2 (Thr202/Tyr204) sites (FIG. 8). A principal consequence of PI3K activation is the activation of the protein kinase Akt, which can be monitored by detection of its phosphorylation status. Akt phosphorylation on Ser 473 and Thr 308 was observed as a result of EGF stimulation of EGFR$^{WT}$-expressing GBM cells and to a lesser extent in EGFR$^{WT/vIII}$-expressing cells (FIG. 9). In contrast, EGFR$^{vIII}$ cells did not display EGF-induced phospho-Akt but instead contain constitutively phosphorylated Akt on Ser 473 (FIG. 9). Phosphorylation of Akt on Thr308 is a PDK1-mediated event. Activation of PDK1 results from a PI3K activity. Thr308 phosphorylated and activated Akt in turn activates mTORC1 (Rapamycin sensitive complex) through a TSC1/2/Rheb cascade (FIG. 11). Amazingly, EGFR$^{vIII}$ expressing cells have constitutively high levels of pSer473 Akt proteins, the result of mTORC2 kinase activity. Similarly, phosphorylation on S6 kinase protein, an mTORC1 event, is only seen in EGFR$^{WT}$ activated cells. The same goes for phosphorylated S6 ribosomal protein.

Finally, an important outcome of Akt activation is the stimulation of the mammalian target of rapamycin complex 1 (mTORC1). One of the many functions of mTORC1 is to maintain homeostatic protein synthesis through, among other proteins, the activation of ribosomal protein S6 kinases (S6Ks; Hay, N. et al. 2004 Genes DEv 18:1926-1945). To evaluate if ligand-stimulated and constitutively activated Akt signals through mTORC1, the phosphorylation status of surrogate markers of mTORC1 activation, S6K and S6 ribosomal protein was investigated. Both S6K and S6 ribosomal protein were phosphorylated upon EGF stimulation of EGFR$^{WT}$-expressing cells and are not present in EGFR$^{vIII}$-expressing cells as shown in FIG. 9.

These observations together allow to establish a model that suggests that the expression of EGFR$^{vIII}$ promotes a switch in the usage of mTOR complexes from mTORC1 (rapamycin sensitive) to mTORC2 (rapamycin insensitive; FIG. 11). It is known that growth factors stimulate mTORC2 activity and some mTORC2 subunits are phosphorylated upon growth factor stimulation, but the responsible kinases remain unknown (Sarbassov, D. D. et al. 2005 Science 307:1098-101; Sarbassov, D. D. et al. 2004 Curr Biol 14:1296-1302; Frias, M. A. et al. 2006 Curr Biol 16:1865-1870). Data herein have significant clinical implications suggesting that a gain of EGFR$^{vIII}$ expression would promote a switch from a Rapamycin sensitive status to an insensitive one. This hypothesis was tested by treating our GBM tumor cells with Rapamycin for 96 hours and measuring the inhibition of cell growth by XTT assays. A dose response growth inhibition effect by rapamycin is observed in cells expressing EGFR$^{WT}$ but not in cells expressing EGFR$^{vIII}$ as shown in FIG. 9. This result is in agreement with the molecular events demonstrated in FIG. 9 and model herein (FIG. 11).

Figure 12:
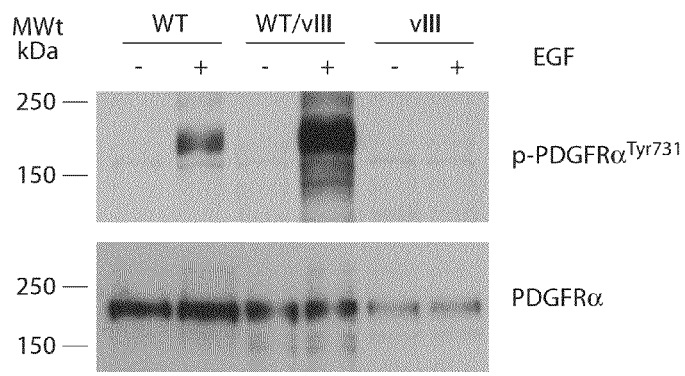
FIG. 12 is a set of photographs of Western blot analyses showing EGF dependent phosphorylation of the PDGF receptor alpha in EGFR$^{wt}$ expressing GBM cells. Western blot analysis of total cell extracts from GBM tumor cells showed that the indicated receptors were expressed. Cells were serum starved and were stimulated as above. Immunoblots were probed with pTyr731 phospho specific anti PDGFRα antibody.

Activation of PI3K by EGF is not through a direct molecular interaction with EGFR but rather through EGFR heterodimers. This is because the SH2 domain of the p85 subunit of PI3K has poor binding affinity for phosphorylated EGFR. PI3K is known to be activated upon EGF stimulation in our EGFR$^{WT}$ expressing GBM cells given the observed activity of Akt. How does then, is PI3K activated in these cells? One possibility is through the surrogate usage of other RTKs by EGFR. In EGFR$^{WT}$ expressing GBM tumor cells, we observed that the PDGFRα is phosphorylated on pTyr731 upon EGF stimulation (FIG. 12). PDGFRα pTyr731 is a potent p85 binding site (Fantl, W. J. et al. 1992 Cell 69:413-423; Kazlauskas, A. et al. 1992 Mol Cell Biol 12:2534-2544; Kashishian, A. et al. 1992 EMBO J 11:1373-1382). Cross receptor heterodimerization of EGFR with other RTK family members have been reported (Saito, Y. et al. 2001 Mol Cell Biol 21:6387-6394; Saito, Y. et al. 2001 J Mal Cell Cardiol 33:3-7; O'Rourke, D. M. et al. 1997 Proc Natl Acad Sci USA 94:3250-3255). It has been postulated that coactivation of receptor tyrosine kinases can affect the response of tumor cells to targeted therapy (Huang, P. H. et al. 2007 Cell Cycle 6:2750-2754; Stommel, J. M. et al. 2007 Science 318:287-290; Engelman, J. A. et al. 2007 Science 316:1039-1043).

Example 17

EGFR Model to Analyze Tumor Biology

Somatic expression of mutant EGFRvIII in the CNS of adult mice, in the context of loss of key tumor suppressor genes, was very efficient at de novo transformation and the formation of GBM tumors in vivo. GBM's most impenetrable attribute to therapeutic intervention is its extreme invasive nature, which makes complete surgical resection virtually unachievable. Invading GBM cells tend to follow distinct anatomical structures within the central nervous system often egressing along white matter tracts, the basement membranes of blood vessels or beneath the subdural sheets. In model herein, migration of EGFR GBM cells within all three spaces was consistently observed (FIG. 4). This reflects the ability of EGFR to activate signaling mechanisms inherent to invasive behaviors, thus making this model an accurate system to study modalities of astrocytoma cell invasion with respect to the tumor microenvironment in a de novo fashion and offer a conduit for testing anti-invasion therapeutic interventions.

Ectopic expression of oncogenes in somatic cells can lead to apoptosis or senescence. Senescence is known to be triggered by the activation of a series of molecular events that involve key cancer proteins such as p53 or p19Arf (Sharpless, N. E. et al. 2007 Nature 436:636-637). The expression of EGFR$^{vIII}$ may induce senescence in normal cells, a hypothesis consistent with the absence of tumor formation in Col1α1-EGFR$^{vIII}$ mice alone (FIG. 2 panel B). In fact, activation of EGFR is rarely seen in the absence of loss of p16INK4a/p14ARF function in GBMs (Consortium TCGA 2008 Nature 455:1061-1068). Therefore, deleting the integral senescence protein p19Arf in InkΔ2/3 null animals likely short-circuits an oncogene-induced senescence and allows for EGFR$^{vIII}$-mediated transformation to take place in these cells.

Expression of wild type EGF receptors under the same circumstances was rather inefficient at tumor formation. This is an unexpected result given the high rate of wild type EGFR overexpression in human GBMs. This discrepancy was not due to differences in EGFR expression levels observed between system herein and human GBM tumors or through a lack of EGFR expression post induction in vivo. It is possible that the EGF receptors herein were not activated to the same level as in human tumors. It is known that human GBMs express high concentrations of EGFR ligands that form autocrine and paracrine loops with the receptors (Ramnaraian, D. B. et al. 2006 Cancer Res. 66:867-874), events that may be absent in animals herein.

Ex vivo cultures of GBM tumors and of primary astrocytes derived from transgenic models herein demonstrate a requirement for additional growth factors for these cells to thrive in vitro. This suggests that in this context, active EGFR is rather inefficient to sustain growth by itself but rather acts in concert with other growth factor inputs to maintain growth of tumor cells. This reflects recent observations in human GBMs describing the importance of understanding integrative RTK signaling complexes to properly devise efficient therapeutic interventions (Stommel, J. M. et al. 2007 Science 318: 287-290; Huang, P. H et al. 2007 Proc Natl Acad Sci USA 104: 12867-12872).

Ascertaining of which signaling pathways emanate from activated EGF receptors was performed by characterizing the extent of phosphorylation events on the receptors (FIG. 7). Indeed, many of the canonical EGFR signaling events are activated in a ligand-dependent manner in the EGFR$^{WT}$ model (FIGS. 8 and 9). Model herein offers a unique opportunity to study the consequences of EGFR$^{vIII}$ expression on GBM tumor biology. For example, constitutive phosphorylation of EGFR$^{vIII}$ receptor on Tyr992 would result in a persistent activation of PLCg signaling pathways, yet the MAPK pathway remains silent in these cells. Activation of PLCg in GBM may signal through a novel mechanism. Given EGFR$^{vIII}$'s potent oncogenecity, this observation underlines a role for PLCg in GBM biology. Using phosphospecific antibodies, the extent of this signaling axis in EGFR$^{WT}$ and EGFR$^{vIII}$-expressing cells was assessed and Akt phosphorylation on Thr308 was only observed in response to EGF activation of EGFR$^{WT}$, whereas expression of EGFR$^{vIII}$ leads to a constitutive phosphorylation of Akt on Ser473. Phosphorylation of Akt on Thr308 is a PDK1-mediated event, the result of PI3K activity. Thr308 phosphorylated Akt in turn activates mTORC1 (a Rapamycin sensitive complex) through a TSC1/2/Rheb cascade (Guertin, D. A. et al. 2007 Cancer Cell 12:9-22). EGFR$^{vIII}$-expressing cells have constitutively high levels of pSer473 Akt proteins, which has been reported to result from an mTORC2 kinase activity (Guertin, D. A. et al. 2007 Cancer Cell 12:9-22). Similarly, phosphorylation on S6 kinase protein, an mTORC1 event, is only seen in EGFR$^{WT}$ activated cells, and the same is true for phosphorylated S6 ribosomal protein. It is possible that the expression of EGFR$^{vIII}$ promotes a switch in the usage of mTOR complexes from mTORC1 (rapamycin sensitive) to mTORC2 (rapamycin insensitive). A gain of EGFR$^{vIII}$ expression may render GBMs insensitive to treatment with Rapamycin and its analogues.

Example 18

Primary Cell Cultures from EGFR GBM Tumors

A series of primary cell cultures from our EGFR; InkΔ2/3$^{-/-}$; PTEN$^{-/-}$ GBM tumors were established. These cells were cultured for more than six months without observable changes in growth behavior, and was found to be capable of reconstituting the histological features observed in the original GBM when orthotopically grafted into the brains of immunocompromised mice. To analyze functional differences between EGFR$^{WT}$ and EGFR$^{vIII}$ signaling processes, cultures were derived from EGFRWT; InkΔ2/3$^{-/-}$; PTEN$^{-/-}$, EGFR$^{WT/vIII}$; InkΔ2/3$^{-/-}$; PTEN$^{-/-}$ and EGFR$^{vIII}$; InkΔ2/3$^{-/-}$; PTEN$^{-/-}$ tumors and were examined. These cultured tumor cells were found to be suitable to assess effects of elimination of gene expression on growth and resistance to drug treatment parameters.

Example 19

Genomic Events in EGFR GBM Tumors

Figure 13A:
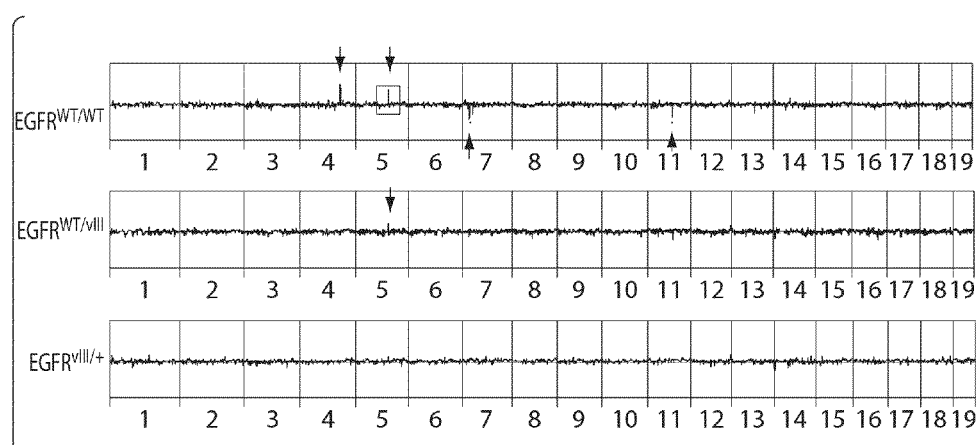
FIG. 13 is a set of data showing focal amplification and deletion of genomic regions in EGFR GBM tumor cells.
Figure 13B:
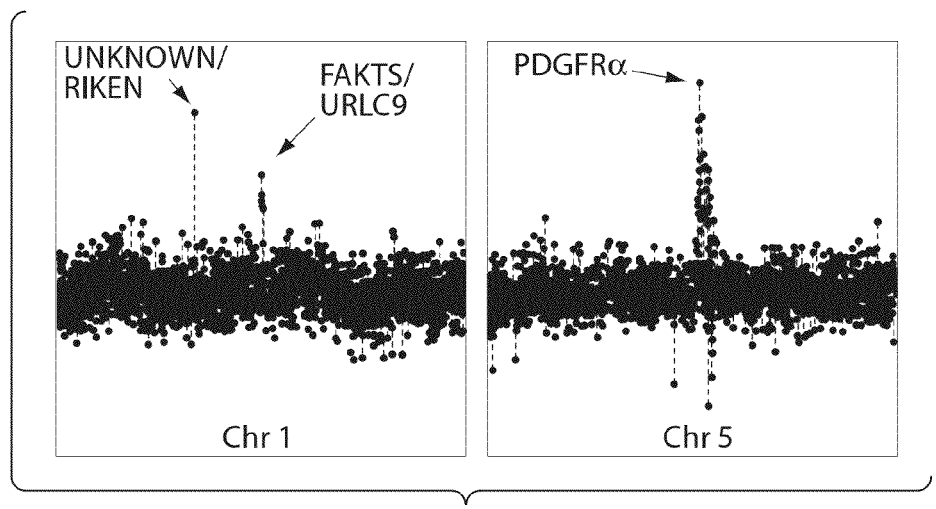
Figure 13C:
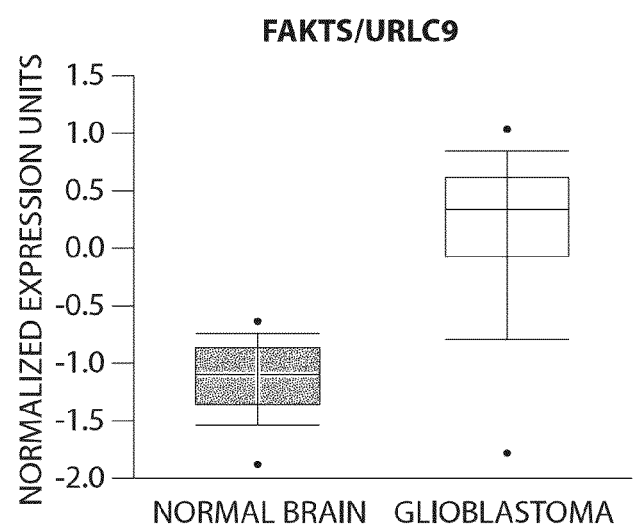
Figure 14A:
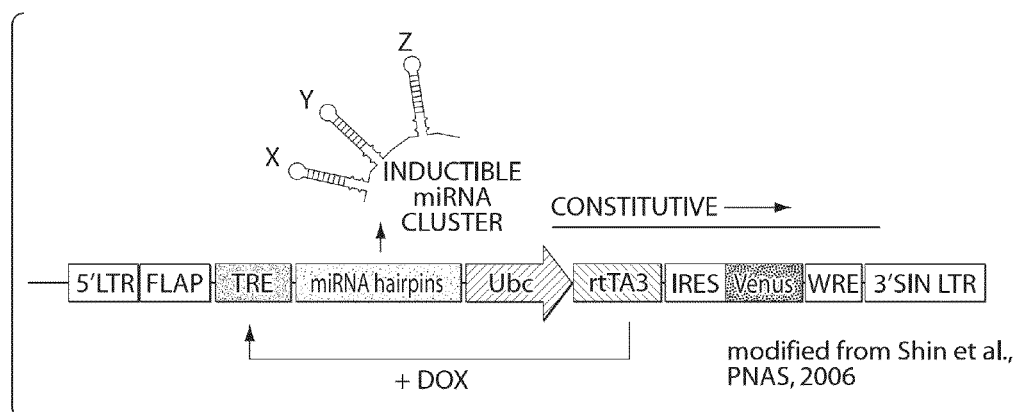
FIG. 14 is a drawing, a set of photographs, and a bar graph showing inducible knockdown in vivo.
Figure 14B:
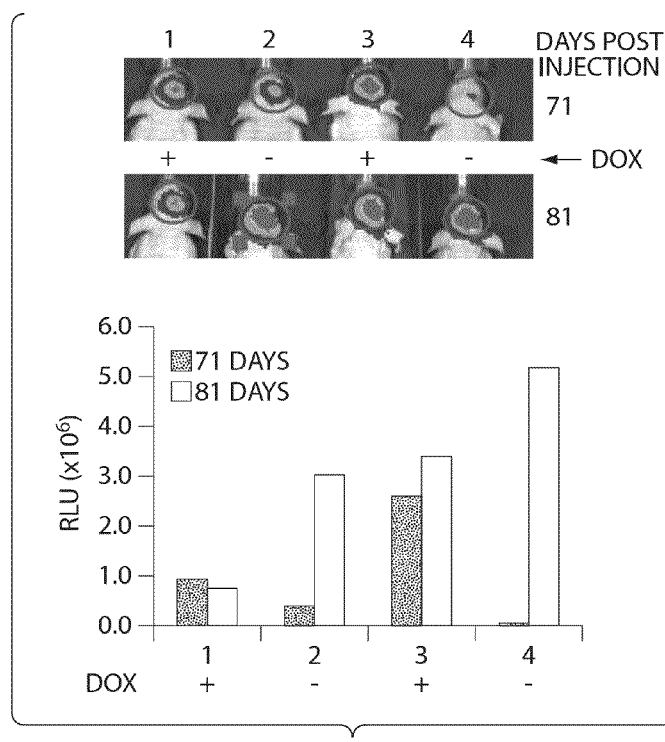
Figure 14C:
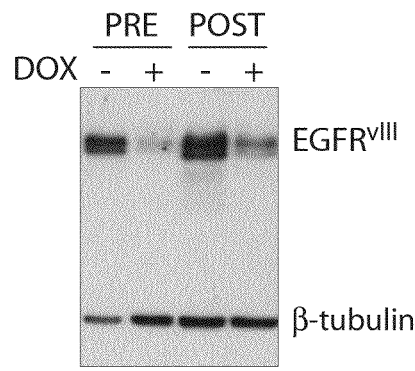
Figure 14D:
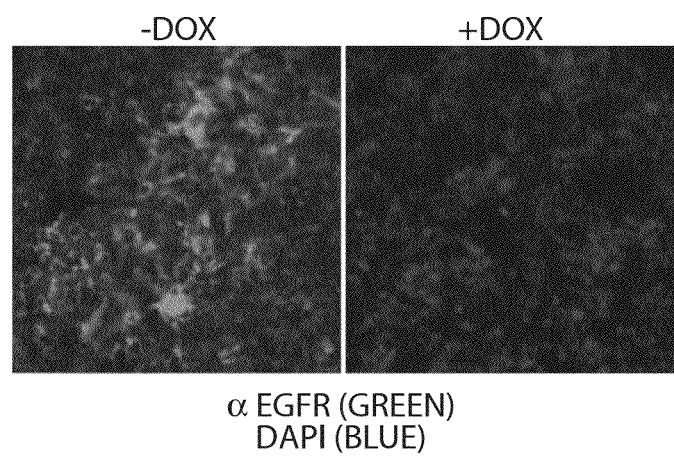

To analyze the mechanism of tumorigenesis in the animal model herein, a copy number aberration analysis was performed on tumor cells expressing each of EGFR$^{WT}$ alone, coexpressing EGFR$^{WT}$ and EGFR$^{vIII}$, and expressing EGFR$^{vIII}$ alone. Array comparative genomic hybridization (CGH) was performed on an Agilent platform and the highest 38 gene loci amplified observed are shown in Table 1. The amplification of the EGFR ligands epiregulin, betacellulin and HB-EGF in the EGFR$^{WT}$ tumor cells was notable. Also, the focal amplification of the PDGFRα gene locus in the EGFR$^{WT}$ tumor cells was observed (FIG. 13). The CGH analysis showed focal deletion and amplicons, for example, on chromosome 1, two focal amplicons were observed, one of which is the FAKTS/URLC9 gene (156. Luhn, P. et al. 2007 Proteins 67:479-489; Kato, T. et al. 2007 Cancer Res 67:8544-8553; FIG. 13 and Table 1). The other, like many hits observed, corresponds to an uncharacterized putative cDNA. Expression of FAKTS/URLC9 gene was observed in human GBM tumors, making FAKTS a suitable target. These data demonstrate validity of mouse models as a tool for discovery of signaling proteins as suitable targets for drug development. This demonstrates the validity of mouse models as a tool for discovery of signaling proteins.

Example 20 pTyr Phosphoproteomic Screen

The GBM tumor cells for selected known phospho-signaling pathways proteins were characterized and a signaling picture developed. These cells were used as a source for a pTyr phospho-proteomic screen. Phosphorylation events (66) were identified on 57 distinct proteins (Table 2). These data shows new targets for therapeutic discovery.

Example 21

Inducible RNAi Knockdown In Vivo

An inducible shRNA system for gene knock down based on the pSLIK vector system was established (Shin, K. J. et al. 2006 Proc Natl Acad Sci USA 103:13759-13764; FIG. 14). Synthetic mir30-driven shRNAs against various genes (represented as X, Y and Z in FIG. 14 panel A) were induced by doxycycline. To test the system, one of EGFR GBM cell lines were infected with a pSLIK virus that expresses a shRNA targeting the EGFR$^{vIII}$ mRNA along with a virus that expresses the firefly luciferase gene to monitor tumor growth using bioluminescence imaging (BLI). Cells (105 total) were injected intracranially in immunocompromized mice and tumors were allowed to develop and were assessed by serial BLI readings. After implantation (71 days) animals were treated with and without doxycycline (FIG. 14 panel B) for 10 days and measure tumor growth using BLI. Tumors from mice treated with doxycycline (1 and 3) did not grow during treatment whereas those from mice not treated with doxycycline (2 and 4) demonstrated an explosive growth rate (FIG. 14 panel B). To corroborate these observations, a western blot analysis was performed using antibodies specific for EGFR$^{vIII}$ from cells extracted from tumor number 3 to demonstrate the retention of EGFR$^{vIII}$ knock down. These data demonstrate that knock down of EGFR$^{vIII}$ in an in vivo setting results in a cytostatic effect.

Example 22

Co-Expression of EGFR$^{WT}$ and TGFα

Ectopic expression of mutant version III (vIII) EGF receptor along with loss of specific tumor suppressor genes in the central nervous system of adult mice result in the formation of malignant gliomas (glioblastoma multiforme) with full penetrance and short latency was previously demonstrated (Zhu, H. et al. 2009 Prac Natl Acad Sci USA 106:2712-2716, hereby incorporated herein by reference in its entirety). EGFR$^{vIII}$ is a potent oncogene capable of readily transforming normal cells into tumor cells.

Figure 15A:
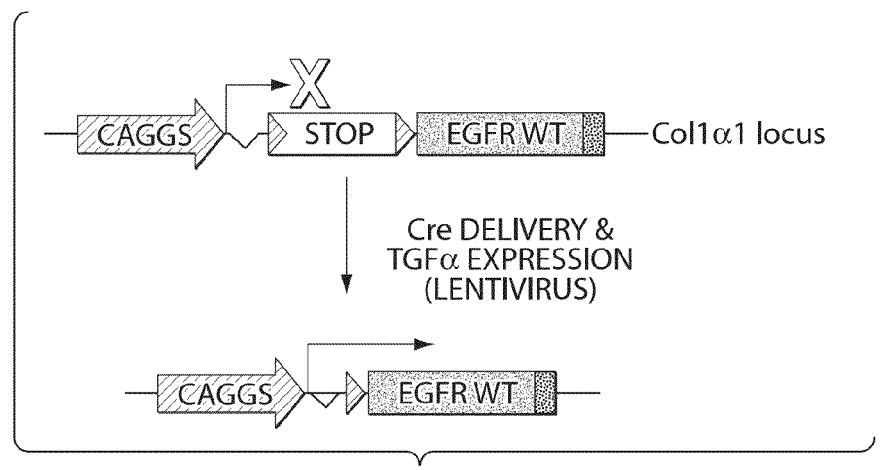
FIG. 15 is a set of drawings showing a schematic representation of the EGFR WT glioma system.
Figure 15B:
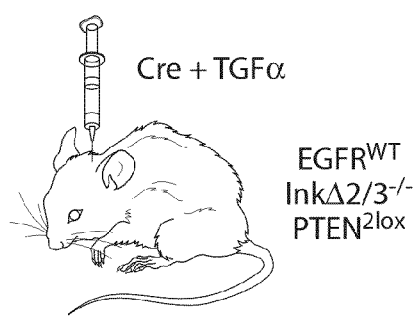
Figure 15C:
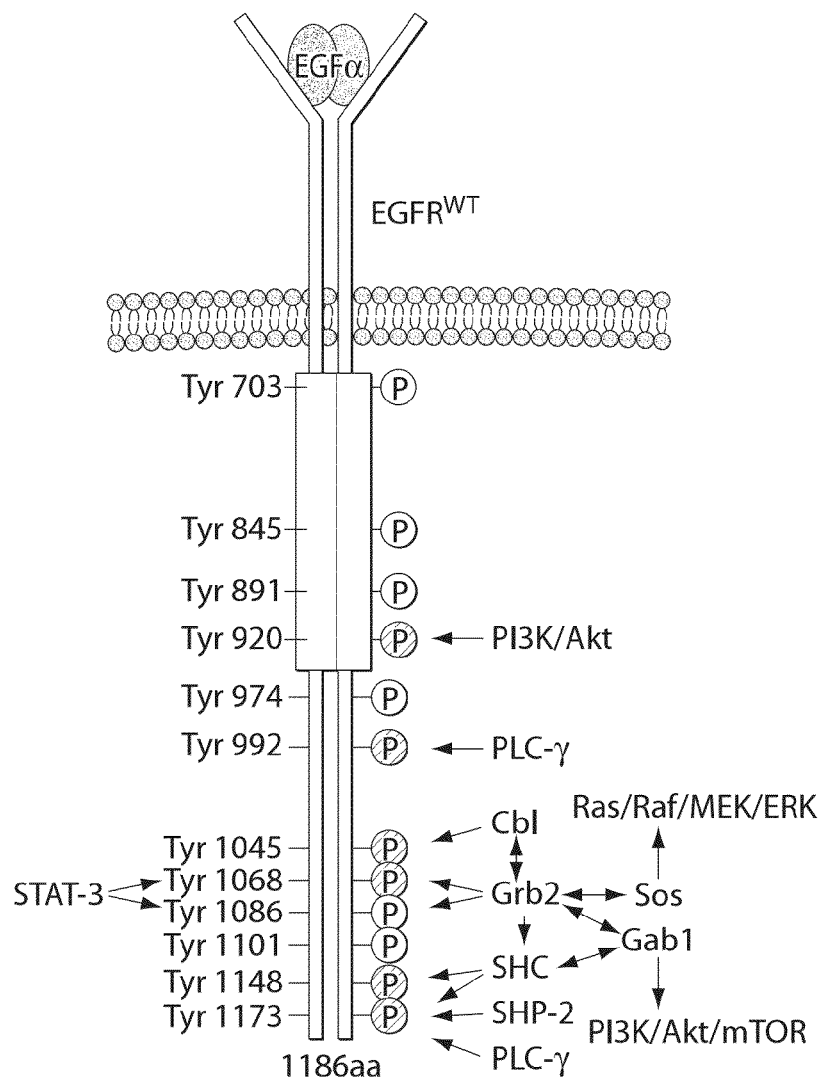

In the same examples and contrary to the EGFR$^{vIII}$ model, the ectopic expression of the wild type EGF receptor (EGFR$^{WT}$) was shown in the context of loss of tumor suppressor genes Ink/Arf and/or PTEN is inefficient at producing glioma tumors in adult mice (Zhu et al. 2009 Proc Natl Acad Sci USA 106:2712-2716, hereby incorporated herein by reference in its entirety). To test whether this might be due to insufficient concentrations of EGFR ligand(s) in the adult mouse brain parenchyma necessary to activate the receptor, a method to co-express an EGFR ligand (for example Transforming Growth Factor Alpha, TGFα) with Cre recombinase from the same virus genome was designed. In doing so, Cre expression leads to expression of the EGFR$^{WT}$, which becomes activated upon TGFα ligand binding (FIG. 15).

TABLE 1

Top 38 genes focally amplified in EGFR GBM tumor cells

| GeneName | Location | EGFR$^{WT/WT}$ | EGFR$^{WT/VIII}$ | EGFR$^{VIII/+}$ | Description |
|---|---|---|---|---|---|
| Sntg1 | chr1:008535403-009268967 | X | X | X | syntrophin, gamma 1 |
| Erbb4 | chr1:068179516-068839298 | X | X | X | v-erb-a erythroblastic leukemia viral oncogene homolog 4 (avian) |
| Fakts/URLC9 | chr1:090159684-090174095 | X | | | 14-3-3 Akt substrate, upregulated in lung cancer 9 |
| Tspan18 | chr2:093011000-093089640 | X | | | tetraspanin 18 |
| Cacna2d1 | chr5:015470676-015852609 | X | X | | calcium channel, voltage-dependent, alpha2/delta subunit 1 |
| Pdgfra | chr5:075458202-075458261 | X | | | platelet derived growth factor receptor, alpha polypeptide |
| Ereg | chr5:092150302-092150361 | X | | | epiregulin |
| Btc | chr5:092465954-092473521 | X | X | | betacellulin, epidermal growth factor family member |
| Tmem132d | chr5:128138502-128654324 | X | X | X | transmembrane protein 132D |
| Pde1c | chr6:056033417-056274770 | X | X | X | phosphodiesterase 1C |
| V2r1b | chr6:123992012-123992071 | | X | | vomeronasal 2, receptor, 1b |
| Nlrp4e | chr7:023061201-023061260 | | | X | NLR family, pyrin domain containing 4E |
| Nlrp5 | chr7:023095989-023096047 | | | X | NLR family, pyrin domain containing 5 |
| Cyp2b9 | chr7:025914425-025914484 | | X | X | cytochrome P450, family 2, subfamily b, polypeptide 9 |
| Cpeb1 | chr7:081221544-081277561 | | X | X | cytoplasmic polyadenylation element binding protein 1 |
| Trim34 | chr7:104152806-104180287 | X | | X | tripartite motif protein 34 |
| Rfx1 | chr8:086968244-086986924 | X | | X | regulatory factor X, 1 |
| Sipa1l2 | chr8:128319359-128343348 | X | X | X | signal-induced proliferation-associated 1 like 2 |
| Olfm2 | chr9:020445803-020470444 | X | X | X | olfactomedin 2 |
| Ecsit | chr9:021830204-021835277 | | X | | ECSIT homolog (*Drosophila*) |
| Ireb2 | chr9:054703687-054728304 | | | X | iron responsive element binding protein 2 |
| Rab6b | chr9:102987674-103019486 | | X | X | RAB6B, member RAS oncogene family |
| Dock3 | chr9:106804718-107039436 | X | X | X | dedicator of cyto-kinesis 3 |
| Erbb3 | chr10:127989095-127997341 | | X | | v-erb-b2 erythroblastic leukemia viral oncogene homolog 3 (avian) |
| Ksr1 | chr11:078885972-078938348 | X | X | X | kinase suppressor of ras 1 |
| Grb7 | chr11:098263216-098263275 | | | X | growth factor receptor bound protein 7 |
| Ccdc46 | chr11:108265512-108660630 | | X | | coiled-coil domain containing 46 |
| AJ409491 | chr12:028384795-028428041 | | X | | RNA binding site for Dazl protein, clone bd3 |
| Ntrk2 | chr13:058835071-059073434 | X | X | | neurotrophic tyrosine kinase, receptor, type 2 |
| Fbp2 | chr13:062855844-062863628 | X | X | X | fructose bisphosphatase 2 |
| Mef2c | chr13:084002364-084106380 | X | X | X | myocyte enhancer factor 2C |
| Gucy1b2 | chr14:061346816-061407336 | X | | | guanylate cyclase 1, soluble, beta 2 |
| Npal2 | chr15:034518404-034518463 | X | X | X | NIPA-like domain containing 2 |
| Rims2 | chr15:039175413-039366091 | X | X | | regulating synaptic membrane exocytosis 2 |
| Polq | chr16:036970888-036979801 | | X | | polymerase (DNA directed), theta |
| Hbegf | chr18:036630906-036641046 | X | | | heparin-binding EGF-like growth factor |
| AF408394 | chr19:008319112-008514037 | X | X | X | putative integral membrane transport protein UST1R |
| Sorcs1 | chr19:050328542-050682163 | X | X | | VPS10 domain receptor protein |

TABLE 2 pTyr events on 57 EGFR GBM tumor cells.

Name

EGFR
SHP-2
Annexin A1
p34 cdc2 homolog A (CDK1)
Gab1
p190RhoGAP
Calmodulin 2
MAPK14
Paxillin
Tensin 1
GSK3a
GSK3b
MAPK1
JAK2
STAM2
Tensin 2
HIPK2
ERK1
AHNAK
odd Oz/ten-m homolog 4
Pyk2
SAP102

TABLE 2-continued pTyr events on 57 EGFR GBM tumor cells.

Name

Stat3
SHANK1
Erbin Dyrk1a
PLCgamma1
Annexin A5
PTK2
Sorting Nexin 9
Stat5a
cdc2-like 5
Stat5b
Caldesmon 1
Adenylate cyclase 7
Stat1
phosphorylase kinase alpha 1
ring finger protein 167
zinc finger protein 294
Interleukin 27 receptor alpha
Annexin A2
Tubulin alpha 1a (alpha 7, 1B, 3, 2)
Shc
Talin 1
PRP4
diazepam binding inhibitor
actin filament associated protein 1-like 2
eEf 1 alpha 1
Septin 2
solute carrier 38, member 2
fyn related kinase (FRK)
CrkL
Crk
splicing factor, arginines/serine rich 9
all-trans-13,14-dihydroretinol saturase
transmembrane protein 106B
Sgk269 (Tyrosine-protein kinase)

Figure 16A:
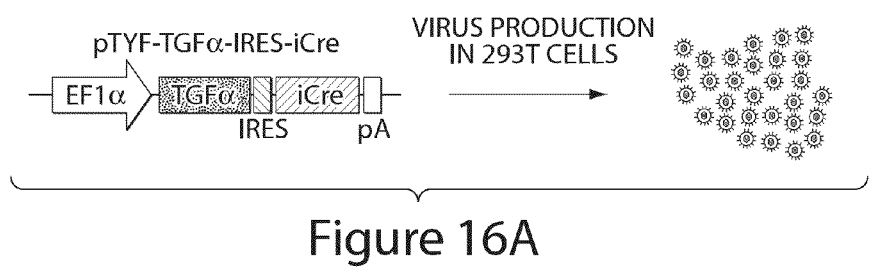
FIG. 16 is a drawing, a photomicrograph and a photograph showing delivery of Cre recombinase and TGFα from the same viral vector.
Figure 16B:
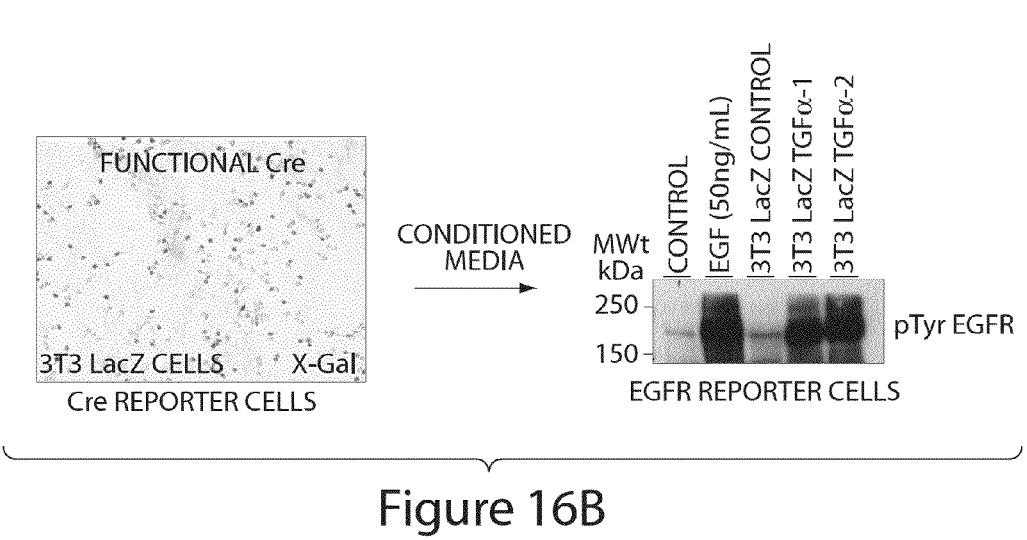

A lentivirus (pTYF-TGFα-IRES-iCre) composed of the Elongation Factor 1α (EF1α) promoter driving the expression of a bicistronic mini gene composed of the human TGFα cDNA, a poliovirus internal ribosomal entry site sequence, followed by the cDNA for improved Cre (iCre) recombinase was constructed. This lentivirus was tested for its capacity to produce functional TGFα and iCre recombinase in cell culture systems (FIG. 16). pTYF-TGFα-IRES-iCre viral particles were produced and concentrated according to published protocols. Once purified, pTYF-TGFα-IRES-iCre virus were used to infect a Cre reporter cell line (3T3 LacZ). In this line, expression of a Cre/loxP conditional β-galactosidase gene is turned on upon Cre activity. One day post infection, cells were extensively washed and fresh media replenished. Two days post infections, the conditioned cell culture media was harvested and the cells were fixed and incubated with the chromogenic substrate X-Gal (blue color) to stain cells that demonstrate Cre activity. Cre recombinase activity is produced from the pTYF-TGFα-IRES-iCre as shown in FIG. 9. To test whether TGFα is produced from these same infected cells, the condition media from these 3T3 LacZ was used to treat an EGFR expressing reporter cell line. In these cells, activation of EGFR (as determined by autophosphorylation events that are visualized by western blot using an anti phosphotyrosine antibody) is dependent on the presence of a ligand. These cells, when treated with 50 ng/mL of purified EGF, undergo rapid receptor phosphorylation (FIG. 16). Upon treatment of these cells with conditioned media expressing TGFα, receptor autophosphorylation is readily detected (FIG. 17) demonstrating that the pTYF-TGFα-IRES-iCre virus is capable of expressing TGFα and iCre upon infection of a target cell.

Figure 17A:
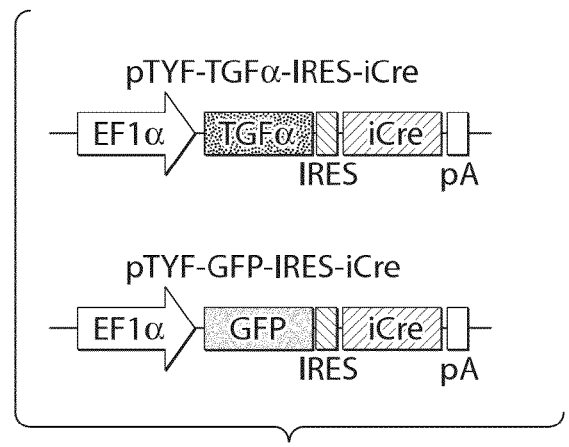
FIG. 17 is a drawing and a Kaplan-Meier graph showing that co-delivery of Cre and TGFα to conditional EGFR WT transgenic mice results in formation of glioblastoma multiforme tumors in vivo.
Figure 17B:
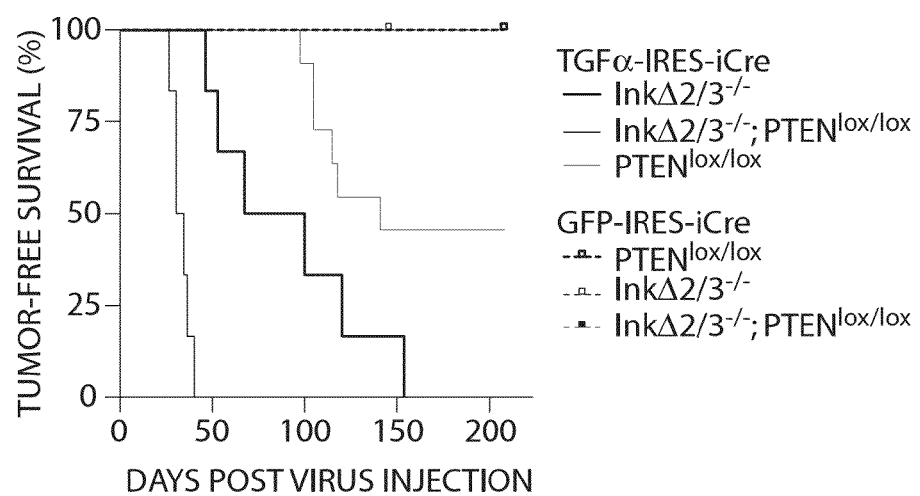

This virus was tested along with a control virus expressing GFP instead of TGFα (FIG. 17 panel A) in conditional EGFR WT transgenic mice in the context of Ink4a/Arf and/or PTEN loss. Cohorts of adult mice were injected intracranially with either pTYF-TGFα-IRES-iCre or pTYF-GFP-IRES-iCre control viruses and monitored for tumor formation to establish Kaplan-Meier survival curves (FIG. 17 panel B). Only mice expressing EGFR WT and TGFα fowled glioblastoma tumors whereas none of the control mice expressing EGFR and GFP developed tumors. The tumors formed contain features that are consistent with human glioblastoma multiforme.

Example 23

Non-Invasive Bioimaging to Monitor Tumor Growth

Figure 18:
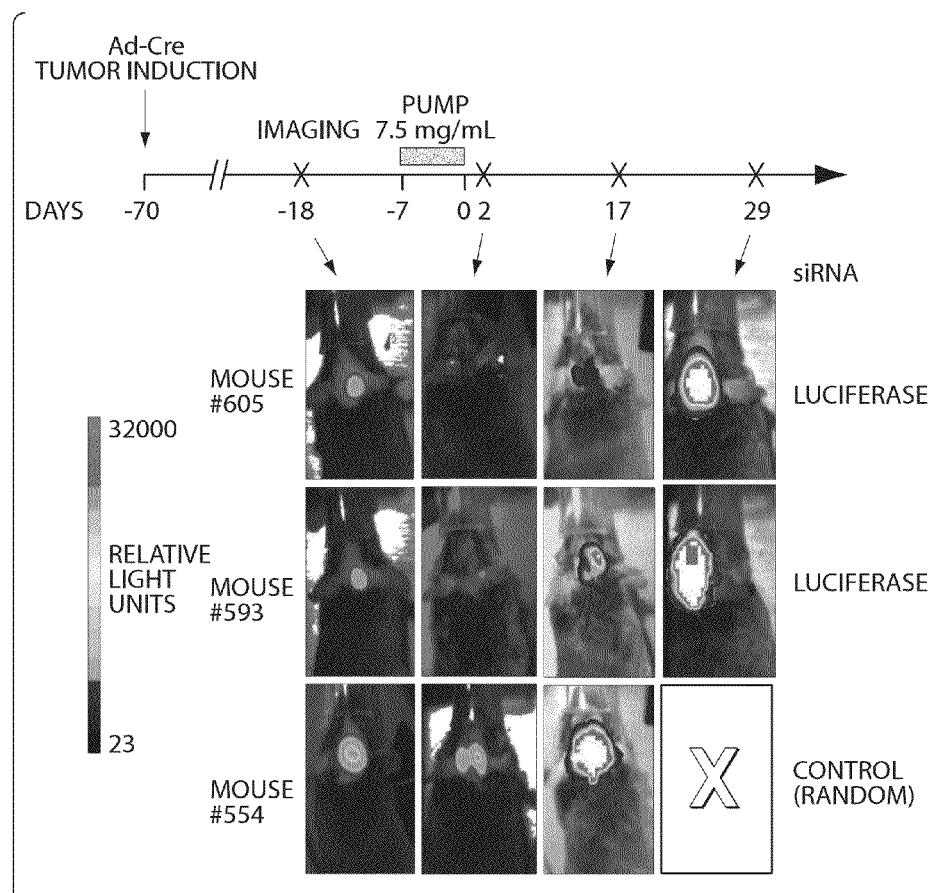
FIG. 18 is a set of serial bioluminescence images of a GBM tumor bearing variant receptor tyrosine kinase encoding FIG-ROS. Luciferase mice were injected with either an siRNA specific for luciferase, or with a random control siRNA. The X denotes that an animal that died prior to imaging day. FIG-ROS is a glioblastoma-associated, ligand-independent rearrangement product of ROS that cooperates with loss of the tumor suppressor gene locus Ink4a;Arf to produce glioblastoma in mouse (Charest, A. et al. 2006 Cancer Res 66:7473-7481).
Figure 19A:
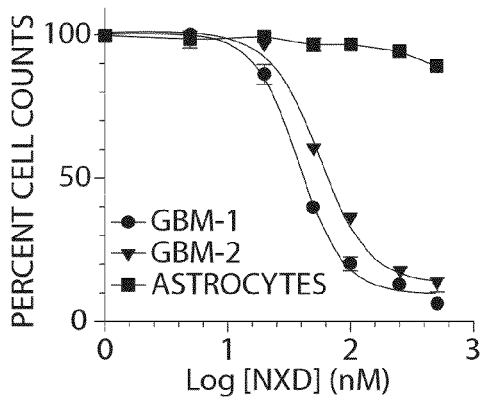
FIG. 19 is a set of line graphs, a bar graph and a photograph of immunoblot analyses showing efficacy of NXD30001 in vitro.
Figure 19B:
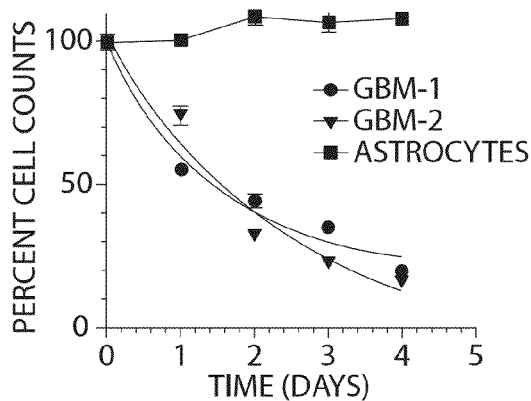
Figure 19C:
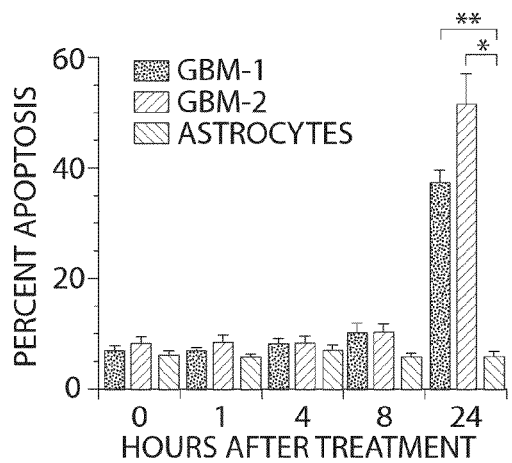
Figure 19D:
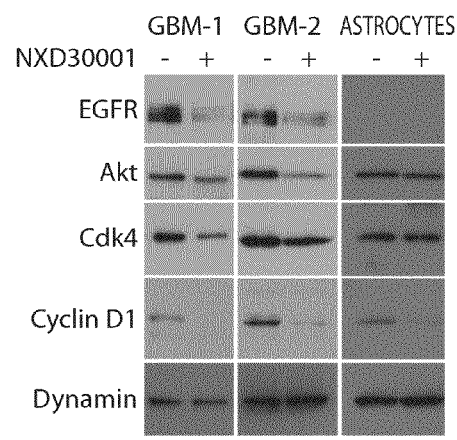

System described herein utilizes viruses to deliver shRNAs against genes involved in GBM tumor maintenance and resistance to therapeutic agents in vivo. This will require a monitoring paradigm. In fact, a major challenge to the analysis of a mouse model of intracranial cancer is the monitoring aspect of disease progression and eventually, of disease treatment. Ideally, one would like to follow tumor formation and growth characteristics under different circumstances in a non-invasive fashion. The current standard procedures are terminal and require the establishment of rather large numbers of animals in order to obtain tumor samples of various stages under different treatments. Non-invasive bioluminescence imaging (BLI) techniques have emerged as a powerful strategy to circumvent these disadvantages. It allows for repetitive and exceptionally sensitive real-time monitoring of disease course and most importantly, for tumor response to therapeutic interventions in individual animals. Being able to visualize tumors in vivo without sacrificing the animals leads to a tremendous reduction in the number of animals used. A firefly (*Photinus pyralis*) luciferase-based bioluminescent reporter strain monitoring system was established to monitor tumor growth parameters over time within the same animal (Woolfenden, S et al 2009 Genesis 47:659-666, hereby incorporated herein by reference in its entirety). Reporter construct herein consists of the firefly luciferase gene driven by a strong, ubiquitous promoter, which is conditionally repressed by the presence of a foxed stop cassette. The rational behind this design is that only cells that are exposed to Cre recombinase, and therefore giving rise to tumor masses in our models of GBM, will express the bioluminescent marker luciferase. This approach provides a high signal to noise ratio, which is one of the major requirements of quantitative bioimaging. This luciferase construct has been inserted randomly in ES cells, several single integrant clones have been tested for inducibility in vitro and three were chosen for the production of chimeric animals. Two independent lines of luciferase reporter transgenics were established. Here, one of two lines was crossed to GBM model mice. AdCre injections performed to monitor the ability to detect tumor growth characteristics in vivo by bioluminescence (FIG. 18). An increase in BLI output was observed to correspond to an increase in tumor volume by serial BLI and MRI imaging.

One of the main objectives of studying human cancers in genetically engineered mouse models (GEMMs) is to recapitulate histopathophysiolocial features of the human disease in a context of tissue microenvironment accuracy. This allows for the identification and characterization of complex molecular mechanisms that are fundamental to cancer. GEMMs are also well suited for examples in the development and testing of new treatment strategies. Since initiation, growth and progression of tumors vary widely on an individual basis, treatment testing of therapeutic agents typically requires large cohorts of animals in order to derive statistically meaningful data. The advent of non invasive molecular imaging for small animals, based on optical, magnetic resonance imaging (MRI), and nuclear medicine modalities has made it possible to study tumor progression longitudinally in individual animals (Kang, J. H. et al. 2008 J Nucl Med 49 (Suppl 2): 164S-179S). MicroCT scans and MRI techniques offer unsurpassed qualities in imaging. However, their use is somewhat dampened by prohibitive costs and intrinsic technological know how required for routine equipment usage, data processing, and analysis. In vivo bioluminescence (BL) techniques have been developed and offer a more amenable modality for quantitative imaging.

Many specific gene promoter-driven BLI reporter strains have been generated (Contag, C. H. et al. 2002 Ann Rev Biomed Eng 4:235-260). These strains can be informative in defined contexts but generally suffer from a lack of versatility. To exploit the cornucopia of Cre/LoxP conditional mouse strains that already exists, two Cre-dependent conditional BLI reporter strains were created and characterized (Lyons, S. K. et al. 2003 Cancer Res 63:7042-7046; Safran et al. 2003 Mol Imaging 2:279-302). These strains, when combined with Cre/LoxP dependent models of cancer, allow for imaging of tumorigenesis. In both reporter strains however, a low level of background BLI prior to Cre expression has been observed (Liao et al. 2007 Cancer Res 67:7525-7533; Svensson et al. 2008 Mol Ther 16:1995-2001) and a small but significant percentage of tumors did not expressed luciferase (Lyons et al. 2003 Cancer Res 63:7042-7046). Cre/LoxP conditional reporter luciferase strain was generated with no detectable background luminescence emission and capable of robust, Cre-mediated bioluminescence. The creation of two reporter strains that can be seamlessly integrated into established mouse models of cancers for BLI monitoring of tumorigenesis is described herein.

Conditional transgenesis necessitates single copy integration and therefore precludes the use of pronuclear injections of fertilized oocytes. Transgenic animals were derived using ES cells, which allowed for screening of insertion copy number and in vitro testing of Cre-mediated luciferase expression prior to chimera production. Firefly luciferase transgene is composed of a ubiquitous promoter whose activity is neutralized by the presence of a foxed transcriptional and translational stop cassette. This transgene was electroporated in ES cells and 46 clones were screened for single integration events by Southern blot analysis. Clones carrying single integrants were subsequently used in a transient, ectopic Cre expression screen for luciferase activity as described in Examples herein. Of the twelve clones tested, three clones demonstrated robust Cre-mediated expression of luciferase activity. These were used to create chimeric animals, of which, clones C6 and F3 transmitted the transgene to the germline and established the founder strains Tg(CAG-luc)C6Char and Tg(CAG-luc)F3Char respectively. The potential for these two strains to express luciferase was ascertained in a tissue-specific manner by crossing them to a transgenic mouse that expresses Cre in thymocytes (Hennet et al. 1995 Proc Natl Acad Sci USA 92:12070-12074). Thymocytes were harvested from double hemizygous TgN(Lck-Cre)548Jxm; Tg(CAG-luc)C6Char and TgN(Lck-Cre)548Jxm;Tg(CAG-luc)F3Char mice and control Tg(CAG-luc)C6Char and Tg(CAG-luc)F3Char animals and assayed for luciferase activity. The data herein demonstrate that the stop cassette recombines in vivo and that both reporters display minimal background and potent luciferase activity when activated by a tissue-specific Cre recombinase.

The strength of a reporter strain relates in part to the extent of background output. To determine the background levels of luciferase activity, multiple organs from both reporter strain were imaged. Conditional luciferase reporter strains Tg(CAG-luc)C6Char and Tg(CAG-luc)F3Char have no background BLI output. Images of multiple organs from control wild type, Tg(CAG-luc)F3Char and Tg(CAG-luc)C6Char mice imaged 20 minutes after luciferin injections were produced. Data herein demonstrates that none of the organs surveyed displayed BL except for Tg(CAG-luc)C6Char's testes. This intriguing observation remains uncharacterized. However, given the extensive epigenetic reprogramming of the male genome during gametogenesis (Rousseaux et al. 2008 Reproduct Biomed Online 16:492-503), it is possible that the strength of the Tg(CAG-luc)C6Char stop cassette is substantially attenuated in the testes due to epigenetic events. Nevertheless, these results demonstrate that the background BL in both Tg(CAG-luc)F3Char and Tg(CAG-luc)C6Char strains is undetectable. Because of its robust in vivo activity and absent BL background, Tg(CAG-luc)C6Char was utilized for further examples.

These reporter strains were designed to be used in well-established Cre/LoxP-dependent cancer models. To determine the ability of the Tg(CAG-luc)C6Char line to accurately monitor tumor development, we retrogressed the transgene into the conditional Tg(CAG-FIGROS)Puro5Char; Cdkn2a$^{tm1Rdp/tm1Rdp}$ malignant glioma model that we developed and characterized (Charest et al. 2006 Cancer Res 66:7473-7481) and into a more aggressive Tg(CAG-FIGROS)Puro5Char;Cdkn2a$^{tm1Rdp/tm1Rdp}$;Pten$^{tm1Hwu/tm1Hwu}$ glioma model that we recently developed.

Longitudinal measurement of GBM tumor growth from individual mice were performed. Tg(CAG-luc)C6Char reporter strain was retrogressed in Tg(CAG-FIGROS)Puro5Char; Cdkn2a$^{tm1Rdp/tm1Rdp}$;Pten$^{tm1Hwu/tm1Hwu}$ mice (#1319, 1349 and 1394) or Tg(CAG-FIGROS)Puro5Char; Cdkn2a$^{tm1Rdp/tm1Rdp}$ mice (#16476, 16477 and 1397) and GBM tumors initiated as described in Examples herein. Sequential images were taken at the indicated times after Ad-Cre intracranial injections except for animals #1394 and #1397 where images were taken 18, 32, 38 and 45, 71, 100 days post Ad-Cre injections respectively. Kaplan-Meier survival curves of mice were created. Expression of the FIGROS oncogene on a compound p16$^{Ink4a}$, p19$^{Arf}$ and PTEN null backgrounds demonstrated a shorter survival latency when compared to mice nullizygous for the p16$^{Ink4a}$, p19$^{Arf}$ locus only. In these mice, GBM tumors developed on an p16$^{Ink4a}$, p19$^{Arf}$ null background with a longer latency than on an p16$^{Ink4a}$, p19$^{Arf}$ and PTEN null background, which translated into a longer survival. Control animals null for p16$^{Ink4a}$, p19$^{Arf}$ and PTEN do not develop tumors within this period. Tg(CAG-FIGROS)Puro5 Char;Cdkn2a$^{tm1Rdp/tm1Rdp}$; Pten$^{tm1Hwu/tm1Hwu}$ n=12, Tg(CAG-FIGROS)Puro5Char; Cdkn2a$^{tm1Rdp/tm1Rdp}$ n=14 and Cdkn2a$^{tm1Rdp/tm1Rdp}$; Pten$^{tm1Hwu/tm1Hwu}$ n=6. In both models, intracranial injections of an adenovirus transducing Cre recombinase (Ad-Cre) initiates expression of the FIGROS oncogene and the production of fully penetrant glioblastoma (GBM) tumors. Cohorts of Tg(CAG-luc)C6Char;Tg(CAG-FIGROS)Puro5Char; Cdkn2a$^{tm1Rdp/tm1Rdp}$, and Tg(CAG-luc)C6Char;Tg(CAG-FIGROS)Puro5Char;Cdkn2a$^{tm1Rdp/tm1Rdp}$Pten$^{tm1Hwu/tm1Hwu}$ compound transgenic mice were longitudinally imaged over time. Data herein demonstrate that Tg(CAG-luc)C6Char-produced BL accurately monitor tumor growth in these mice.

Next the background BL output was determined from mice that have undergone recombination of the luciferase transgene stop element but that are not developing gliomas. Ad-Cre was injected in a cohort of Tg(CAG-luc)C6Char; Cdkn2a$^{tm1Rdp/tm1Rdp}$;Pten$^{tm1Hwu/tm1Hwu}$ controls animals and periodically imaged. Animals of this genotype do not develop glioma.

Longitudinal measurement of background levels of the luciferase reporter Tg(CAG-luc)C6Char strain when activated intracranially were performed. Sequential IVIS images of Tg(CAG-luc)C6Char;Cdkn2a$^{tm1Rdp/tm1Rdp}$ Pten$^{tm1Hwu/tm1Hwu}$ animal #1540 that has been intracranially injected with $1\times10^8$ Ad-Cre viral particles were obtained at the indicated times. Data herein demonstrates that the injection of Ad-Cre intracranially resulted in the basal expression of the luciferase transgene and emissions of less than $10^6$ photons/sec/cm$^2$/sr. Importantly, these emission levels remain constant over a considerable length, which likely represents cells within the CNS with minimal turnover rates. An additional strength of bioimaging lies in its ability to correlate tumor volumes to output light emission. From the cohorts mice displaying various BLI outputs were sacrificed immediately after imaging and processed for histological analysis of tumor volumes.

A strong relationship exists between output light emission and tumor volume (regression analysis $R^2=0.983$). This result demonstrates that Tg(CAG-luc)C6Char reporter strain is capable of volumetric tumor growth detection in vivo.

Having demonstrated that the Tg(CAG-luc)C6Char strain is capable of accurately monitoring GBM growth, we tested its capacity to image mice developing non-small-cell lung cancer (NSCLC). To this end, we crossed the Tg(CAG-luc) C6Char stain to the conditional oncogenic K-ras$^{G12D}$ allele mouse Kras$^{tm4tyj/+}$ (Jackson et al. 2001 Genes Dev 15:3243-3248) and compound hemizygous offsprings were subjected to NSCLC initiation (Jackson et al. 2001 Genes Dev 15:3243-3248). Serial imaging of the same animal demonstrates that development and growth of NSCLC can be readily monitored over time. The data highlights the versatility of our reporter strains to image tumor growth in diverse cancer models.

Conditional cancer models are such that the initial recombination that result in the oncogenic activation is entirely dependent on Cre expression. By integrating a similarly Cre-dependent reporter gene into those strains, the recombined loci in the targeted cells as well as in their progenies will continue to express the oncogene and the reporter. This allows for a stoichiometric relationship between tumor cell number and reporter detection, which makes it ideal for surveying dynamic parameters of cancer growth The extent of background BLI output may be significant if our reporter luciferase strains are used in conjunction with Cre/LoxP conditional tumor models that have an intrinsically low tumor penetrance. In these situations, the signal to noise ratio may be lower due to a higher proportion of cells that have switched on the expression of both oncogene and reporter luciferase and that failed to develop tumors. In this context, monitoring of early stages of tumorigenesis may be more difficult. In both models of GBM and NSCLC described above, the penetrance of tumor formation is 100%. This increases the signal to noise ratio such that accurate measurement of early tumor growth is possible. We believe that the study of conditional mouse models of cancer that are characterized by a fully penetrant tumor phenotype will greatly benefit from the reporter strains described herein.

Example 24

Convection Enhanced Delivery of siRNAs in Brain Tumor Bearing Mice

The data herein demonstrates the feasibility of delivery siRNAs intracranially to GBM tumor-bearing mice. Injection was performed by convection-enhanced delivery (CED) through the use of an osmotic pump (Alzet, Durect Corp.), a BrdU-labeled inert siRNA intracranially for a period of 7 days to GBM tumor bearing mice and assess the local biodistribution of the agent. IF against the BrdU tag demonstrates a potent penetration of the siRNA molecules within the growing tumor bed. This indicates that there is very little, if any, physical barrier to the administration of siRNAs to tumor bearing animals.

Next, the functionality of CED-mediated injection of an siRNA in luciferase expressing GBM tumor-bearing animals was demonstrated (FIG. 18). GBM tumors were initiated and their development monitored by BLI. A chemically fortified siRNA against luciferase was delivered through CED for 7 days. An inert siRNA was used as a control. FIG. 18 demonstrates functional silencing of the luciferase reporter in mice administered with an siRNA against luciferase but not in control mice. The observed silencing was transient. This experiment demonstrates the feasibility of direct delivery of siRNA to GBM tumor-bearing mice and underscore the potential of the technology to mediate potent and effective silencing of genes in vivo.

Example 25

Effect of NXD30001 Treatment of GBM Cell Cultures

Mouse primary cultures of astrocytes and GBM cell cultures from the animal model herein were grown in the presence of HSP90 inhibitor (NXD30001; Nexgenix Pharmaceuticals). As shown herein, GBM-1 cells co-express wild type and vIII EGFR and GBM-2 cells express EGFRvIII alone. Effective concentration of the compound was determined using a cell count assay in which cells were treated with increasing concentrations if NXD30001 for 36 hours. The plotted data shows that cell counts in both GBM-1 and GBM-2 tumor cell lines decreased to a survival of less than 10% after treatment with 2.8 nM NXD30001 (FIG. 19 panel A). Another cell count assay was performed to assess cell survival as a function of time after cells were treated with 250 nM NXD30001. Survival of GBM-1 and GBM-2 cells were observed to decrease to less than 20% relative to total cell number four days post treatment with NDX30001 (FIG. 19 panel B). Further, apoptosis rate was determined in cells exposed to the compound, which were fixed and stained at different time periods after treatment. Apoptosis rate in GBM-1 and GBM-2 cells was 40% and 50%, respectively, relative to total number of cells 24 hours after NDX30001 treatment (FIG. 19 panel C).

Efficacy of treatment was further assessed by immunoblot analyses of lysates of GBM cells and astrocytes using antobodies specific to each of EGFR, Akt4, Cdk4 and CyclinD1 (FIG. 19 panel D). Data showed significant depletion of EGFR proteins resulted from administering to cells NXD30001 compared to control cells not administered the compound. Akt 4, Cdk4 and Cyclin D1 proteins in treated with NXD30001 GBM-1 and GBM-2 cells were also depleted.

Example 26

Effect of NXD30001 Treatment in Live Animal Models

Figure 20A:
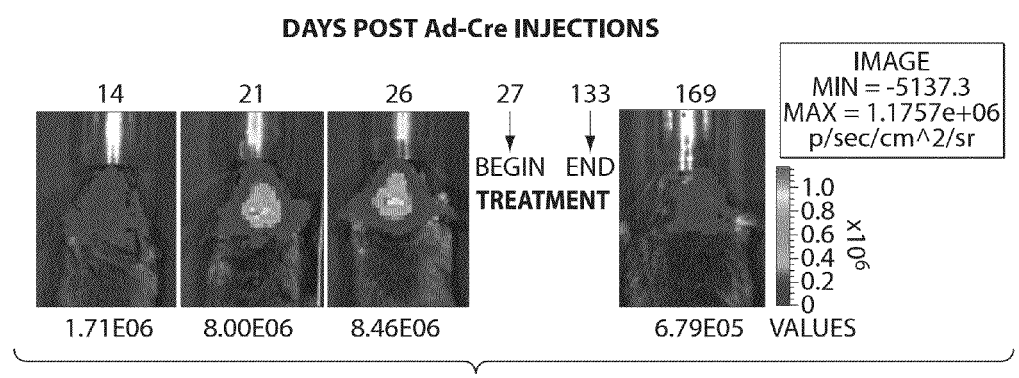
FIG. 20 is a set of photographs and a Kaplan-Meier graph showing NXD30001 treatment of GBM tumor model mice described herein.
Figure 20B:
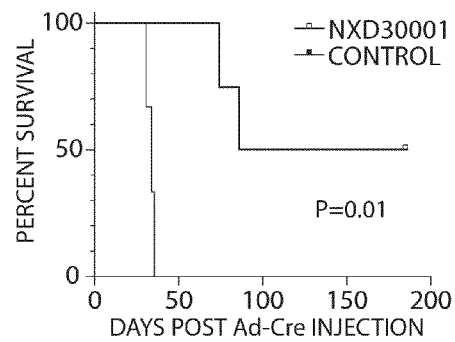
Figure 20C:
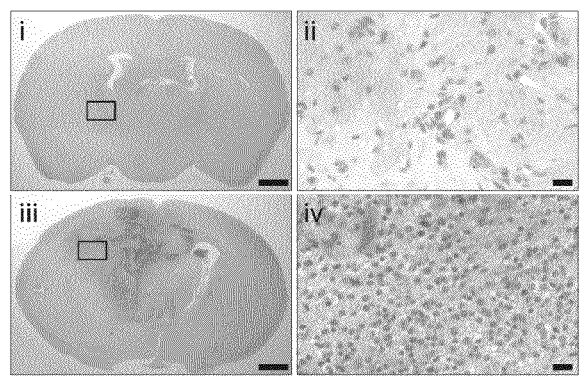

NXD30001 was tested in conditional EGFR mice using BLI imaging to monitor survival rate of treated animals as a function of time (FIG. 20). Mice were examined at each of 14, 21 and 26 days post tumor induction to determine the time for treatment initiation. The data showed that mice were ready to be treated with NXD30001 at 27 days after tumor induction. Imaging during the treatment was not performed since luciferase is a client protein of HSP90. However, imaging of mice was resumed 36 days pots treatment (FIG. 20 panel A).

Kaplan-Meier analysis of survival rate of conditional EGFR mice treated with NXD30001 showed that one hundred days post Ad-Cre injection, survival rate was 50% in animals treated with NXD30001 compared to control untreated mice all of which died by 40 days post tumor induction (FIG. 20 panel B).

The histopathological analysis of H&E stained paraffin embedded brain sections of NXD30001 treated animals and controls showed proliferation of tumor cells in controls, and absence of such proliferation as a result of NXD30001 treatment (FIG. 20 panel C).

Figure 21:
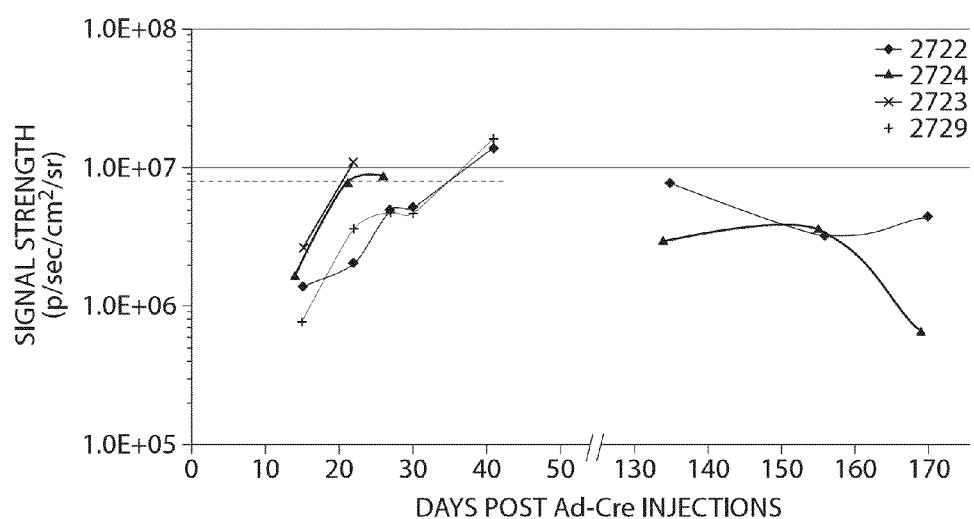
FIG. 21 is a line graph showing use of bioluminescence to monitor tumor growth development and response to treatment. Four brain tumor-bearing mice were monitored using luciferase bioluminescence and data is amount of reported signal strength as a function of time post tumor induction. Once the animals reached a threshold of $8 \times 10^6$ p/sec/cm$^2$/sr, treatment with NXD30001 was initiated. Two surviving animals (2722 and 2724) were serially imaged post treatment over 30 days, and absence of tumor growth post cessation of treatment was observed in those animals.

Further, two animals surviving treatment with NXD30001 were monitored for 30 days post cessation of treatment, and lack of tumor growth was observed (FIG. 21).

Example 27

Cytotoxicity study of NXD30001

Cytotoxicity of NXD30001 was assessed in GMB cell proliferating cultures obtained from clinical mouse subjects and was compared to that of 17-(Allylamino)-17-demethoxygeldanamycin (17-AAG), an ansamycin antibiotic which binds to HSP90. Data obtained was analyzed as half maximum inhibitory concentration (1050) values (Table 3). Data show effectiveness of NXD30001 in inhibiting cell proliferation in comparison to treatment with 17-AAG. On average, NXD30001 was found to be a much more potent inhibitor of cell proliferation than 17-AAG, as proliferation rate of GBM-2 cells treated with NXD30001 was about ten fold lower than cells treated with 17-AAG.

TABLE 3

Cytotoxicity of NXD30001 and 17-AAG in GBM cultures

| GBM | NXD30002 $IC_{50}(nM)$* | 17-AAG $IC_{50}(nM)$* |
|---|---|---|
| 2414 | 31.7 ± 4.9 | 205.1 ± 13.1 |
| 46 | 54.3 ± 12.5 | 91.9 ± 1.4 |
| 69 | 73.4 ± 2.5 | 91 ± 4.3 |
| 42 | 73.8 ± 0.7 | 165.5 ± 24.9 |
| 2734 | 77.6 ± 2.8 | 381 ± 24.1 |
| GBM-1 | 78.3 ± 8.3 | 207.5 ± 9.6 |
| 41 | 80.2 ± 5.9 | 100.2 ± 5.0 |
| GBM-2 | 110.8 ± 9.4 | 1096.4 ± 118.6 |
| 2000 | 115.4 ± 9.4 | 344.8 ± 75.5 |
| 2227 | 134.3 ± 7.7 | 712 ± 54.4 |
| 2231 | 146.1 ± 3.7 | 737.3 ± 72.0 |
| 2415 | 251.1 ± 57.7 | 328.8 ± 50.1 |
| 102 | 360.5 ± 21.6 | 626.2 ± 6.0 |
| 103 | 575.6 ± 14.8 | 793.5 ± 28.7 |

*Results are presented as the mean of three independent experiments ± standard deviation.

Example 28

Depletion of HSP90-Regulated Proteins by NXD30001 Treatment

Figure 22:
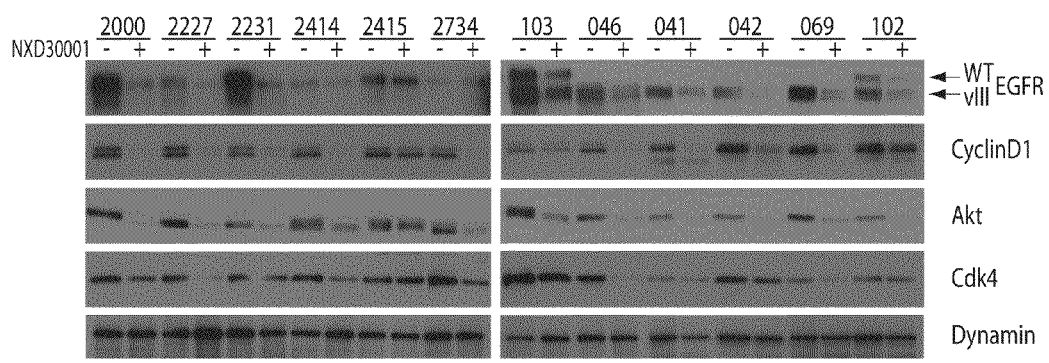
FIG. 22 is a set of photographs of immunoblots showing depletion of HSP90 client proteins EGFR, Akt, Cyclin D1 and Cdk4 in the mouse GBM cell strains as indicated. Cells (+) were treated with 250 nM of NXD30001 for 24 hours. Treated cells show much less of the client proteins than untreated (−) controls.

Western blot analysis was performed on cell lysates obtained from twelve GMB cell cultures treated with NXD30001, using antibodies specific for each of EGFR WT and vIII, CyclinD1, Akt and CDK4. These proteins were depleted in most of the cell cultures (FIG. 22). Almost complete depletion of EGFR proteins resulting from NXD30001 treatment was observed in GBM lines 2000, 2231, 103 and 069. Depletion of CyclinD1 and Akt proteins after NXD30001 treatment was also observed. Cdk4 protein levels were somewhat affected by NXD3001 treatment but not so substantially as EGFR WT and vIII.

These data show that NXD30001 efficiently suppresses activation of EGFR, PI3K/Akt and ras/raf/MEK/ERK pathways and that these pathways participate in GBM tumor formation, shown in examples supra.

Example 29

Effect of Erlotinib Treatment in GBM Live Animal Models

Figure 23A:
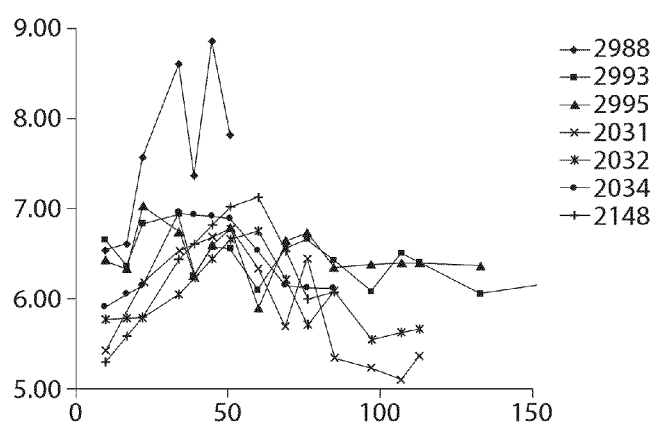
FIG. 23 is a line graph and photographs showing effect of erlotinib (Tarceva) on live tumor-bearing animals.
Figure 23B:
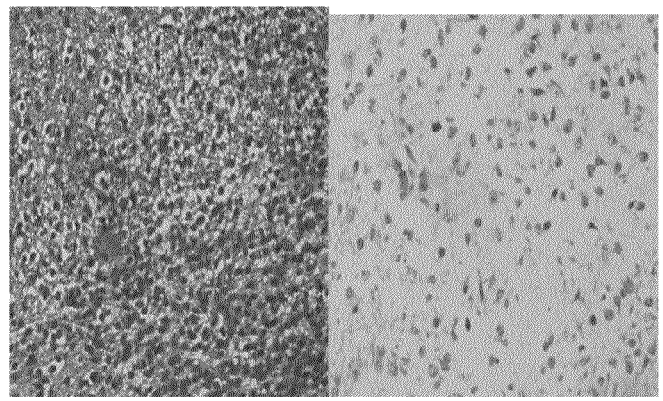

Sensitivity to additional compounds of subject animals in the GBM model described herein was further tested using tyrosine kinase inhibitor Tarceva (erlotinib; Genentech Inc., San Francisco, Calif.). Conditional EGFR animals were examined using bioluminescence imaging at different periods of time after tumor induction with Ad-Cre-recombinase by the methods above. At a time point after bioluminescence output reached $8 \times 10^6$ p/sec/cm$^2$/sr, animals were administered with Tarceva. Animal number 2148 was observed to have essentially been cured of cancer at 80 days after Tarceva treatment (FIG. 23 panel A). Histopathological analysis of H&E stained sections of mouse number 2148 treated with Tarceva, and a control untreated mouse revealed absence of proliferating tumor cells in the treated animal (FIG. 23 panel 13).

Example 30

Antisense Oligonucleotide Technology (ASO) in GBM Live Animal Models

Figure 24A:
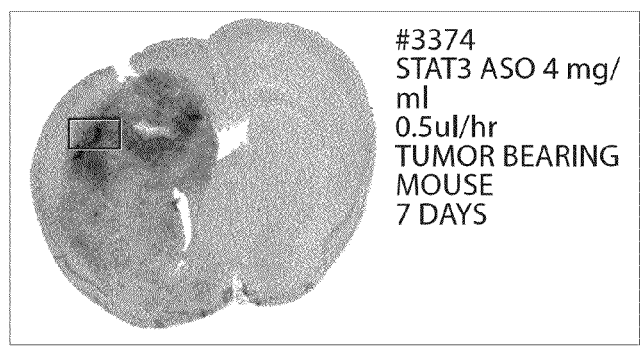
FIG. 24 is a set of photographs showing antisense oligonucleotide (ASO) delivery into tumor-bearing animals.
Figure 24B:
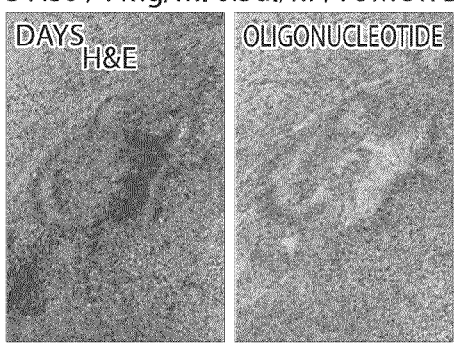
Figure 24C:
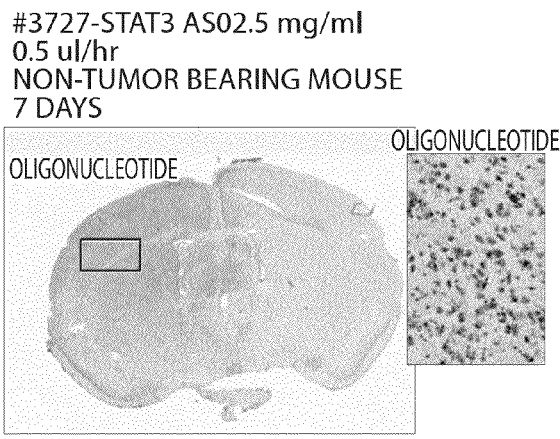

As was described in Examples herein, activation of signal transducer and activator of transcription (STAT3) pathway was found to be causally involved in GBM tumors. To assess ASO technology for reducing or even eliminating specific gene function within tumors formed in conditional EGFR animals, an ASO against STAT3 was injected through convection enhanced delivery. Histopathological analyses of H&E stained section of GBM-bearing animal showed the ASO penetration in tumor cells in comparison with control, normal brain of non tumor-bearing animal (FIG. 24).

Figure 25A:
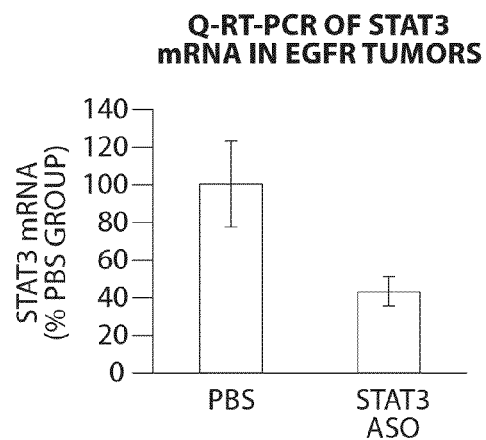
FIG. 25 is a set of bar graphs showing data on the levels of STAT3 mRNA obtained from quantitative reverse transcriptase PCR of mRNA isolated from control PBS-treated mice and STAT3 ASO-treated model animals.
Figure 25B:
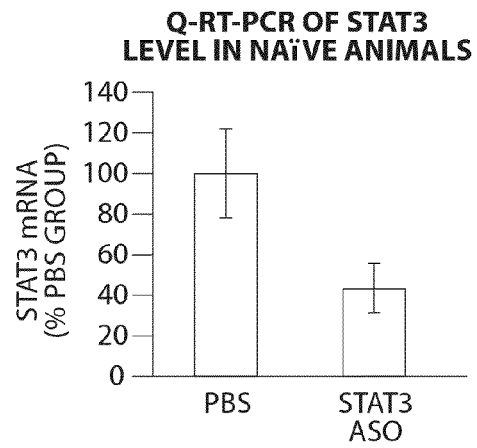

Data from quantitative reverse transcriptase PCR analysis from mRNA isolated from PBS treated and STAT 3ASO treated tumor-bearing animals compared to that of non-tumor bearing control animals showed that STAT3 ASO mRNA level in the treated both tumor-bearing animals was similar to that of the control mice (FIG. 25 panels A and B). These data shows efficiency of ASO technology in eliminating functional expression of specific genes within a tumor microenvironment and potential use of efficient molecular therapeutic agents to treat brain tumors.

What is claimed is:

1. A method for screening at least one compound to determine ability to treat an oncological disorder regulated through a tumor-inducing pathway, the method comprising:

administering the compound to transgenic mice as an animal disease model, wherein the transgenic mice display pathology symptoms that correspond to the oncological disorder Glioblastoma multiforme in a human, wherein the genome of the transgenic mice comprises a regulatable transgene of human origin of a wild type epidermal growth factor receptor ($EGFR^{WT}$) and a mutant form vIII ($EGFR^{vIII}$) associated with tumor formation ($EGFR^{WT}$/ $EGFR^{vIII}$) or two copies of transgene $EGFR^{vIII}$ ($EGFR^{vIII}$/$EGFR^{vIII}$), wherein expression of the transgene is associated with tumor formation, and the genome of the transgenic mice further comprises mutations in genes encoding Phosphatase and Tensin homolog detected on chromosome Ten (PTEN), p16Ink4a, and p19Arf as regulatable genes, wherein the disease pathology symptoms are induced using a-site-specific recombination system to induce expression of the transgene associated with tumor formation and negatively regulate or eliminate the gene expression of pTEN, p16Ink4a and p19Arf genes;

analyzing tumors appearing in the transgenic mice administered the compound; and, comparing appearance and amount of tumors in the transgenic mice administered the compound and in control transgenic mice not administered the compound, wherein a decrease in tumors in the transgenic mice administered the compound compared to control transgenic mice is an indication that the compound treats the oncological disorder.

2. The method according to claim 1, wherein the transgene which encodes $EGFR^{vIII}$ is under control of a cytomegalovirus (CMV) promoter immediate early enhancer and a chicken β-actin promoter sequence (pCAGGS), wherein the promoter is conditionally repressed by presence of a foxed stop cassette wherein the $EGFR^{vIII}$ encoding region is flanked at 3' and 5' ends by collagen1α1 genomic sequences, and wherein the transgene is expressed in cells contacted with Cre recombinase.

3. The method according to claim 2 further comprising performing stereotactic intracranial injection of adenovirus transducing Cre recombinase (Ad-CMVCre), wherein cre-lox function overproduces EGFR$^{VIII}$ and EGFR$^{WT}$ and down regulates Phosphatase and Tensin homolog detected on chromosome Ten (PTEN).

4. The method according to claim 2, further comprising observing an amount of expression of a bioluminescent marker under the control of a strong ubiquitous promoter, wherein the promoter is conditionally repressed by presence of the floxed stop cassette, wherein the marker is expressed in cells contacted with Cre recombinase, wherein the cells produce tumors and express the marker.

5. The method according to claim 1, wherein comparing appearance and the amount of the tumors is performed in live mice.

6. The method according to claim 1, wherein comparing the amount of the tumors further comprises observing by immunohistochemical staining of tumor sections from sacrificed mice or ex vivo mouse cell cultures at least one of: extent of cellularity as a measure of proliferation; presence of pleomorphic nuclei; presence of a fibrillary background; extent of membrane expression of EGFR; presence of astrocytic markers glial fibrillary acidic protein (GFAP) or S100β or both; extent of proliferating cells by presence of mitoses; extent of areas of necrosis; presence of perineuronal satellitosis;

and presence of tumor cells migrated distal to main tumor mass.

7. The method according to claim 1, further comprising after comparing, analyzing an amount of mammalian target of rapamycin complex (mTORC) protein in the tumors in the transgenic mice administered the compound and in the control transgenic mice, wherein analyzing comprises determining at least one of: expression of mTORC per total protein; activation of mTORC activity; extent and pattern of mTORC phosphorylation; and relative usage of mTORC1 and mTORC2.

8. A method for screening at least one compound to determine ability to treat an oncological disorder regulated through a tumor-inducing pathway, the method comprising:
administering the compound to transgenic mice as an animal disease model, wherein the transgenic mice display pathology symptoms that correspond to the oncological disorder Glioblastoma multiforme in a human; wherein the genome of the transgenic mice comprises a regulatable wild type EGFR (EGFR$^{WT}$) transgene of human origin and a transgene encoding human transforming growth factor-α(TGFα), wherein expression of the transgene EGFR$^{WT}$ and the transgene TGFα are associated with tumor formation, and the genome of the transgenic mice further comprises mutations in genes encoding Phosphatase and Tensin homolog detected on chromosome Ten (PTEN), p16Ink4a, and p19Arf as regulatable genes, wherein the disease pathology symptoms are induced using a site-specific recombination system to induce expression of the transgene associated with tumor formation and negatively regulate or eliminate the gene expression of pTEN, p16Ink4a and p19Arf genes;
analyzing tumors appearing in the transgenic mice administered the compound; and,
comparing appearance and amount of tumors in the subjects administered the compound to that in control transgenic mice not administered the compound, wherein a decrease in tumors in the transgenic mice administered the compound compared to the control transgenic mice is an indication that the compound treats the oncological disorder.

9. The method according to claim 8 further comprising regulating the tumor formation transgene with a cytomegalovirus (CMV) promoter immediate early enhancer and a chicken β-actin promoter sequence (pCAGGS), wherein the promoter is conditionally repressed by the presence of a floxed stop cassette, and wherein the transgene is flanked at 3' and 5' ends by collagen1α1 genomic sequences wherein the transgene is expressed in cells contacted with Cre recombinase.

10. The method according to claim 8 further comprising performing stereotactic intracranial injection of adenovirus transducing Cre recombinase (Ad-CMVCre), wherein cre-lox function overproduces EGFR$^{WT}$ and down regulates Phosphatase and Tensin homolog detected on chromosome Ten (PTEN).

11. The method according to claim 8, wherein comparing the appearance and the amount of the tumors in transgenic mice further comprises bioimaging to monitor tumor growth non-invasively.

12. The method according to claim 11, wherein non-invasive bioimaging comprises observing an amount of expression of a bioluminescent marker under the control of a strong ubiquitous promoter, wherein the promoter is conditionally repressed by presence of a floxed stop cassette, wherein the marker is expressed in cells contacted with Cre recombinase, wherein the cells produce tumors and express the marker.

13. The method according to claim 12, wherein comparing appearance and amount of tumors is performed in live mice.

14. The method according to claim 8, wherein comparing the amount of the tumors further comprises observing by immunohistochemical staining of tumor sections from sacrificed mice or ex vivo mouse cell cultures at least one of: extent of cellularity as a measure of proliferation; presence of pleomorphic nuclei; presence of a fibrillary background; extent of membrane expression of EGFR; presence of astrocytic markers glial fibrillary acidic protein (GFAP) or S100 β or both; extent of proliferating cells by presence of mitoses; extent of areas of necrosis; presence of perineuronal satellitosis; and presence of tumor cells migrated distal to main tumor mass.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 1
gcacagcatt gcggacatgc                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 2
ccctccatgt gtgaccaagg                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 3
gcagaagcgc ggccgtctgg                                                   20

<210> SEQ ID NO 4
<211> LENGTH: 21
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 4
ccccctgaac ctgaaacata a                                                 21

<210> SEQ ID NO 5
<211> LENGTH: 21
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 5
atgggcagct ccttcagtcc g                                                 21

<210> SEQ ID NO 6
<211> LENGTH: 20
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 6

-continued

```
taaatgccac cggcaggatg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 7
ctgcataagg ctatgaagag                                              20

<210> SEQ ID NO 8
<211> LENGTH: 20
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 8
gaggagttca tgatcagtgc                                              20

<210> SEQ ID NO 9
<211> LENGTH: 21
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 9
ccgtacacca aaatttgcct g                                            21

<210> SEQ ID NO 10
<211> LENGTH: 21
<212> TYPE: DNA
<213> ORGANISM: Artificial Sequence
<220> FEATURE:
<223> OTHER INFORMATION: Synthesized nucleotide sequence for polymerase
      chain reaction

<400> SEQUENCE: 10
ccctgatcct ggcaatttcg g                                            21
```